US008778307B2

(12) United States Patent
Galindo et al.

(10) Patent No.: US 8,778,307 B2
(45) Date of Patent: *Jul. 15, 2014

(54) TARGETED CARRIERS FOR DRUG DELIVERY ACROSS THE GASTROINTESTINAL EPITHELIUM

(75) Inventors: Silvia Muro Galindo, Silver Spring, MD (US); Rasa Ghaffarian, Columbia, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/463,796

(22) Filed: May 3, 2012

(65) Prior Publication Data

US 2012/0263652 A1 Oct. 18, 2012

Related U.S. Application Data

(63) Continuation-in-part of application No. 13/376,362, filed as application No. PCT/US2010/037490 on Jun. 4, 2010.

(60) Provisional application No. 61/481,779, filed on May 3, 2011, provisional application No. 61/220,404, filed on Jun. 25, 2009, provisional application No. 61/184,657, filed on Jun. 5, 2009.

(51) Int. Cl.
*A61K 39/395* (2006.01)
*A61K 49/00* (2006.01)

(52) U.S. Cl.
USPC .................................. 424/9.1; 424/172.1

(58) Field of Classification Search
None
See application file for complete search history.

(56) References Cited

U.S. PATENT DOCUMENTS

| 5,599,790 | A | 2/1997 | Altieri et al. | |
| 6,737,058 | B2 * | 5/2004 | Altieri et al. | 424/139.1 |
| 2009/0202511 | A1 | 8/2009 | Galindo et al. | |
| 2010/0151005 | A1 | 6/2010 | Muro-Galindo et al. | |

FOREIGN PATENT DOCUMENTS

| WO | 9913918 A2 | 3/1999 | |
| WO | WO 2006/007560 A2 * | 1/2006 | 424/94.6 |
| WO | 2007024817 A2 | 3/2007 | |
| WO | 2007072070 A1 | 6/2007 | |
| WO | 2008147526 A1 | 12/2008 | |
| WO | 2010141879 A2 | 12/2010 | |

OTHER PUBLICATIONS

Muro et al. Molecular Therapy. 13(1);135-141:2006.*
Kvale et al. Scan J Immunol. 35;669-676:1992.*
Altieri, D., et al., "Structural Recognition of a Novel Fibrinogen y Chain Sequence (117-133) by Intercellular Adhesion Molecule-1 Mediates Leukocyte-Endothelium Interaction", "The Journal of Biological Chemistry", Jan. 13, 1995, pp. 696-699, vol. 270, No. 2.
Artursson, P., "Epithelial Transport of Drugs in Cell Culture. I: A Model for Studying the Passive Diffusion of Drugs over Intestinal Absorbtive (Caco-2) Cells", "Journal of Pharmaceutical Sciences", Jun. 1990, pp. 476-482, vol. 79, No. 6.
Bareford, L., et al., "Endocytic mechanisms for targeted drug delivery", "Advanced Drug Delivery Reviews", Jun. 28, 2007, pp. 748-758, vol. 59.
Boyd, J., et al., "Fibrinogen decreases cardiomyocyte contract through an ICAM-1-dependent mechanism", "Critical Care", Jan. 2008, pp. R2, vol. 12, No. 1.
Chen, H., et al., "Oral particulate delivery: status and future trends", "Advanced Drug Delivery Reviews", 1998, pp. 339-350, vol. 34.
Chen, H., et al., "Lectin-bearing Polymerized Liposomes as Potential Oral Vaccine Carriers", "Pharmaceutical Research", 1996, pp. 1378-1383, vol. 13, No. 9.
Danilov, S., et al., "Lung uptake of antibodies to endothelial antigens: key determinants of vascular immunotargeting", "Am J Physiol Lung Cell Mol Physiol", 2001, pp. L1335-L1347, vol. 280.
Dejana, E., "Endothelial Cell-Cell Junctions: Happy Together", "Nature Reviews: Molecular Cell Biology", Apr. 2004, pp. 261-270, vol. 5.
Dermaut, B., et al., "Aberrant lysosomal carbohydrate storage accompanies edocytic defects and neurodegeneration in *Drosophila* benchwarmer", "The Journal of Cell Biology", Jul. 4, 2005, pp. 127-139, vol. 170, No. 1.
Dhami, R., et al., "Mannose 6-Phosphate Receptor-mediated Uptake Is Defective in Acid Sphingomyelinase-deficient Macrophages", "The Journal of Biological Chemistry", Jan. 9, 2004, pp. 1526-1532, vol. 279, No. 2.
Ding, B. et al., "Advanced Drug Delivery Systems That Target the Vascular Endothelium", "Molecular Interventions", Apr. 2006, pp. 98-111, vol. 6, No. 2.
Dippold, W., et al., "Expression of intercellular adhesion molecule 1 (ICAM-1, CD54) in colonic epithelial cells", "Gut", 1993, pp. 1593-1597, vol. 34.
Discher, B., et al., "Cross-linked Polymersome Membranes: Vesicles with Broadly Adjustable Properties", "J. Phys. Chem. B", 2002, pp. 2848-2854, vol. 106.

(Continued)

*Primary Examiner* — Karlheinz R Skowronek
*Assistant Examiner* — Schuyler Milton
(74) *Attorney, Agent, or Firm* — Hultquist, PLLC; Mary B. Grant

(57) ABSTRACT

A system and method for transcellular transport of compositions containing agents (e.g., research, analytical, reporter or molecular probes, diagnostic and therapeutic agents, biologically active agents, research agents, analytical agents, imaging agents, monitoring agents, enzymes, proteins, peptides, nucleic acids, lipids, sugars, hormones, lipoproteins, chemicals, viruses, bacteria, cells, including modified cells, biosensors, markers, antibodies and/or ligands) across the gastrointestinal epithelial layer including use of a composition containing the agent and a targeting moiety, specific for a determinant at the target location. An exemplary composition of the system includes an anti-ICAM antibody targeting moiety, specific for targeting ICAM-1. The system enables effective, versatile, and safe targeting and transport of agents. The system is useful in research applications, as well as in the context of translational science and clinical interventions.

12 Claims, 21 Drawing Sheets

(56) References Cited

OTHER PUBLICATIONS

D'Souza, S., et al., "Identification of an Active Sequence within the First Immunoglobulin Domain of Intercellular Cell Adhesion Molecule-1 (ICAM-1) That Interacts with Fibrinogen", "The Journal of Biological Chemistry", 1996, pp. 24270-24277, vol. 271, No. 39.

Duperray, A., et al., "Molecular Identification of a Novel Fibrinogen Binding Site on the First Domain of ICAM-1 Regulating Leukocyte-Endothelium Bridging", "The Journal of Biological Chemistry", Jan. 3, 1997, pp. 435-441, vol. 272, No. 1.

Dziubla, T., et al., "Chapter 23 Nanocarriers for the Vascular Delivery of Drugs to the Lungs", "Nanoparticulates as Drug Carriers (V. Torchilin, Ed.)", 2006, pp. 499-506, Publisher: Imperial College Press.

Garnacho, C., et al., "Differential intra-endothelial delivery of polymer nanocarriers targeted to distinct PECAM-1 epitopes", "Journal of Controlled Release", Jun. 18, 2008, pp. 226-233, vol. 130.

Garnacho, C., et al., "Delivery of Acid Sphingomyelinase in Normal and Niemann-Pick Disease Mice Using Intercellular Adhesion Molecule-1-Targeted Polymer Nanocarriers", "Journal of Pharmacology and Experimental Therapeutics", May 2008, pp. 400-408, vol. 325, No. 2.

Ghandehari, H., "Materials for advanced drug delivery in the 21st century: a focus area for Advanced Drug Delivery Reviews", "Advanced Drug Delivery Reviews", Apr. 8, 2008, p. 956, vol. 60.

Hallahan, D., et al., "Intercellular adhesion molecule 1 knockout abrogates radiation induced pulmonary inflammation", "Proc. Natl. Acad. Sci.", Jun. 1997, pp. 6432-6437, vol. 94.

Hamman, J., et al., "Targeting Receptors, Transporters and Site of Absorption to Improve Oral Drug Delivery", "Drug Target Insights", 2007, pp. 71-81, vol. 2.

Hans, M., et al., "Biodegradable nanoparticles for drug delivery and targeting", "Current Opinion in Solid State and Materials Science", 2002, pp. 319-327, vol. 6.

He, X., et al., "A fluorescence-based, high-performance liquid chromatographic assay to determine acid sphingomyelinase activity and diagnose types A and B Niemann—Pick disease", "Analytical Biochemistry", 2003, pp. 116-120, vol. 314.

Hidalgo, I., et al., "Characterization of the Human colon Carcinoma Cell Line (Caco-2) as a Model System for Intestinal Epithelial Permeability", "Gastroenterology", Mar. 1989, pp. 736-749, vol. 96, No. 3.

Hidalgo, I., et al., "Transport of a large neutral amino acid (phenylalanine) in a human intestinal epithelial cell line: Caco-2", "Biochimica et Biophysica Acta", 1990, pp. 25-30, vol. 1028.

Hopkins, A., et al., "ICAM-1: targeted docking for exogenous as well as endogenous ligands", "Advanced Drug Delivery Reviews", 2004, pp. 763-778, vol. 56.

Huang, G., et al., "Infection of Human Intestinal Epithelial Cells with Invasive Bacteria Upregulates Apical Intercellular Adhesion Molecule-1 (ICAM-1) Expression and Neutrophil Adhesion", "The Journal of Clinical Investigation", Jul. 1996, pp. 572-583, vol. 98, No. 2.

Hubbard, A., et al., "Intercellular Adhesion Molecule-1 (ICAM-1) Expression and Cell Signaling Cascades", "Free Radical Biology & Medicine", 2000, pp. 1379-1386, vol. 28, No. 9.

Jung, T., et al., "Biodegradable nanoparticles for oral delivery of peptides: is there a role for polymers to affect mucosal uptake?", "European Journal of Pharmaceutics and Biopharmaceutics", 2000, pp. 147-160, vol. 50.

Kavanaugh, A., et al., "Repeat Treatment of Rheumatoid Arthiritis Patients with a Murine Anti-intercellular Adhesion Molcule 1 Monoclonal Antibody", "Arthritis & Rheumatism", May 1997, pp. 849-853, vol. 40, No. 5.

Kelly, C., et al., "Human colon cancer cells express ICAM-1 in vivo and support LFA-1-dependent lymphocyte adhesion in vitro", "Am J Physiol Gastrointest Liver Physiol", 1992, pp. G864-G870, vol. 263.

Kim, S., et al., "Fibrinogen binding to ICAM-1 promotes EGFR-dependent mucin production in human airway epithelial cells", "Am J Physiol Lung Cell Mol Physiol", May 2009, pp. L174-L183, vol. 297, No. 1.

Kitchens, K., et al., "Transepithelial and endothelial transport of poly (amidoamine) dendrimers", "Advanced Drug Delivery Reviews", Nov. 11, 2005, pp. 2163-2176, vol. 57.

Languino, L., et al., "Fibrinogen Mediates Leukocyte Adhesion to Vascular Endothelium through an ICAM-1-Dependent Pathway", "Cell", Jul. 2, 1993, pp. 1423-1434, vol. 73.

Lee, C., et al., "Designing dendrimers for biological applications", "Nature Biotechnology", Dec. 6, 2005, pp. 1517-1526, vol. 23, No. 12.

Minko, T., et al., "New Generation of Liposomal Drugs for Cancer", "Anti-Cancer Agents in Medicinal Chemistry", 2006, pp. 537-552, vol. 6.

Moghimi, S., et al., "Stealth liposomes and long circulating nanoparticles: critical issues in pharmacokinetics, opsonization and protein-binding properties", "Progress in Lipid Research", 2003, pp. 463-478, vol. 42.

Monroy, M., et al., "Abnormal Osteoclast Morphology and Bone Remodeling in a Murine Model of a Lysosomal Storage Disease", "Bone", Feb. 2002, pp. 352-359, vol. 30, No. 2.

Murciano, J., et al., "ICAM-directed vascular immunotargeting of antithrombotic agents to the endothelial luminal surface : Presented in part as posters at the American Thoracic Society (ATS) Meeting, May 5-10, 2000, Toronto, ON, Canada", "Blood", May 15, 2003, pp. 3977-3984, vol. 101.

Muro, S., et al., "A novel endocytic pathway induced by clustering endothelial ICAM-1 or PECAM-1", "Journal of Cell Science", 2003, pp. 1599-1609, vol. 116.

Muro, S., et al., "Targeting of Antioxidant and Anti-Thrombotic Drugs to Endothelial Cell Adhesion Molecules", "Current Pharmaceutical Design", 2005, pp. 2383-2401, vol. 11.

Muro, S., et al., "Lysosomal Enzyme Delivery by ICAM-1-Targeted Nanocarriers Bypassing Glycosylation- and Clathrin-Dependent Endocytosis", "Molecular Therapy", Sep. 8, 2005, pp. 135-141, vol. 13, No. 1.

Muro, S., "Chapter 117 Intercellular Adhesion Molecule-1 and Vascular Cell Adhesion Molecule-1", "The Endothelium: A Comprehensive Reference (W. Aird, Ed.)", Jan. 19, 2007, pp. 1058-1070, Publisher: Cambridge University Press, Published in: New York.

Muro, S, et al., "Control of Endothelial Targeting and Intracellular Delivery of Therapeutic Enzymes by Modulating the Size and Shape of ICAM-1-targeted Carriers", "Mol Ther.", Aug. 2008, pp. 1450-1458, vol. 16, No. 8.

Muro, S., et al., "Slow intracellular trafficking of catalase nanoparticles targeted to ICAM-1 protects endothelial cells from oxidative stress", "Am J Physiol Cell Physiol", 2003, pp. C1339-C1347, vol. 285.

Muro, S., et al., "ICAM-1 recycling in endothelial cells: a novel pathway for sustained intracellular delivery and prolonged effects of drugs", "Blood", Sep. 14, 2004, pp. 650-658, vol. 105, No. 2.

Muzykantov, V., "Biomedical aspects of targeted delivery of drugs to pulmonary endothelium", "Expert Opin. Drug Deliv.", 2005, pp. 909-926, vol. 2, No. 5.

Oh, P., et al., "Subtractive proteomic mapping of the endothelial surface in lung and solid tumours for tissue-specific therapy", "Nature", Jun. 10, 2004, pp. 629-635, vol. 429.

Owen, R., "Uptake and transport of intestinal macromolecules and microorganisms by M cells in Peyer's patches-a personal and historical perspective", "Seminars in Immunology", 1999, pp. 157-163, vol. 11.

Note: For the non-patient literature citations that no month of publication is indicated, the year of publication is more than 1 year prior to the effective filing date of the present application.

Pardridge, W., "Molecular Trojan horses for blood-brain barrier drug delivery", "Current Opinion in Pharmacology", Jul. 12, 2006, pp. 494-500, vol. 6.

Pol, A., et al., "Cholesterol and Fatty Acids Regulate Dynamic Caveolin Trafficking through the Golgi Complex and between the Cell Surface and Lipid Bodies", "Molecular Biology of the Cell", Apr. 2005, pp. 2091-2105, vol. 16.

Ponchel, G., et al., "Specific and non-specific bioadhesive particulate systems for oral delivery to the gastrointestinal tract", "Advanced Drug Delivery Reviews", 1998, pp. 191-219, vol. 34.

(56) References Cited

OTHER PUBLICATIONS

Predescu, D., et al., "Functional and morphological studies of protein transcytosis in continuous endothelia", "Am J Physiol Lung Cell Mol Physiol", Nov. 2004, pp. L895-L901, vol. 287.

Puri, V., et al., "Cholesterol modulates membrane traffic along the endocytic pathway in sphingolipid-storage diseases", "Nature Cell Biology", Oct. 1999, pp. 386-388, vol. 1.

Rezai, K., et al., "Comparison of tight junction permeability for albumin in iris pigment epithelium and retinal pigment epithelium in vitro", "Graefe's Arch Clin Exp Ophthalmol", 1997, pp. 48-55, vol. 235.

Rossin R., et al., "In Vivo Imaging of 64Cu-Labeled Polymer Nanoparticles Targeted to the Lung Endothelium", "The Journal of Nuclear Medicine", Jan. 2008, pp. 103-111, vol. 49, No. 1.

Rothlein, R., et al., "A Human Intercellular Adhesion Molecule (ICAM-1) Distinct From LFA-1", "The Journal of Immunology", Aug. 15, 1986, pp. 1270-1274, vol. 137, No. 4.

Russell-Jones, G., "The potential use of receptor-mediated endocytosis for oral drug delivery", "Advanced Drug Delivery Reviews", 2001, pp. 59-73, vol. 46.

Sakhalkar, H., et al., "Leukocyte-inspired biodegradable particles that selectively and avidly adhere to inflamed endothelium in vitro and in vivo", "PNAS", Dec. 23, 2003, pp. 15895-15900, vol. 100, No. 26.

Savin, V., et al., "Measurement of Albumin Reflection Coefficient With Isolated Rat Glomeruli", "J. Am. Soc. Nephrol.", 1992, pp. 1260-1269, vol. 3, No. 6.

Schnitzer, J., "Caveolae: from basic trafficking mechanisms to targeting transcytosis for tissue-specific drug and gene delivery in vivo", "Advanced Drug Delivery Reviews", 2001, pp. 265-280, vol. 49.

Schuchman, E., et al., "Chapter 8 the Development of Enzyme Replacement Therapy for Lysosomal Diseases: Gaucher Disease and Beyond", "Gaucher disease: Lessons learned about therapy of lysosomal disorders (Futerman, A., Ed.)", Jun. 1, 2006, pp. 125-140, Publisher: CRC Press.

Takei, Y., et al., "Expression of ICAM-1 is Involved in the Mechanism of Liver Injury During Liver Transplantation: Therapeutic usefulness of the F(ab')2 Fragment of an Anti-ICAM-1 Monoclonal Antibody", "Transplantation Proceedings", Apr. 1996, pp. 1103-1105, vol. 28, No. 2.

Torchilin, V., "Multifunctional nanocarriers", "Advanced Drug Delivery Reviews", Sep. 18, 2006, pp. 1532-1555, vol. 58.

Tsakadze, N., et al., "Interactions of Intercellular Adhesion Molecule-1 with Fibrinogen", "Trends Cardiovascular Medicine", Apr. 2002, pp. 101-108, vol. 12, No. 3.

Villanueva, F., et al., "Microbubbles Targeted to Intercellular Adhesion Molecule-1 Bind to Activated Coronary Artery Endothelial Cells", "Circulation", 1998, pp. 1-5, vol. 98.

Weisel, J., "Fibrinogen and Fibrin", "Advances in Protein Chemistry", 2005, pp. 247-299, vol. 70.

Weller, G., et al., "Modulating Targeted Adhesion of an Ultrasound Contrast Agent to Dysfunctional Endothelium", "Annals of Biomedical Engineering", 2002, pp. 1012-1019, vol. 30.

Yang, L, et al., "ICAM-1 regulates neutrophil adhesion and transcellular migration of TNF-alpha-activated vascular endothelium under flow", "Blood", Jul. 15, 2005, pp. 584-592, vol. 106.

Yin, Y., et al., "Lectin-conjugated PLGA nanoparticles loaded with thymopentin: Ex vivo bioadhesion and in vivo biodistribution", "Journal of Controlled Release", Jul. 5, 2007, pp. 27-38, vol. 123.

Panyam, J., et al., "Biodegradable nanoparticles for drug and gene delivery to cells and tissue", "Advanced Drug Delivery Reviews", 2003, pp. 329-347, vol. 55.

Anderson, M., et al., "Mechanism of Binding and Internalization of ICAM-1-Derived Cyclic Peptides by LFA-1 on the Surface of T Cells: A Potential Method for Targeted Drug Delivery", "Pharmaceutical Research", Oct. 2003, pp. 1523-1532, vol. 20, No. 10.

Belizaire, A., et al., "Identification of a murine ICAM-1-specific peptide by subtractive phage library selection on cells", "Biochemical and Biophysical Research Communications", 2003, pp. 625-630, vol. 309.

Chittasupho, C., et al., "ICAM-1 targeting of doxorubicin-loaded PLGA nanoparticles to lung epithelial cells", "European Journal of Pharmaceutical Sciences", Feb. 27, 2009, pp. 141-150, vol. 37.

Hayashi, T., et al., "MUC1 Mucin Core Protein Binds to the Domain 1 of ICAM-1", "Digestion", 2001, pp. 87-92, vol. 63 (Suppl 1).

Jaafari, M., et al., "Targeting of Liposomes to Human Keratinocytes Through Adhesive Peptides from Immunoglobulin Domains in the Presence of IFN-gamma", "Drug Delivery", 2002, pp. 1-9, vol. 9.

Kam, J., et al., "MUC1 Synthetic Peptide Inhibition of Intercellular Adhesion Molecule-1 and MUC1 Binding Requires Six Tandem Repeats", "Cancer Research", Dec. 1, 1998, pp. 5577-5581, vol. 58.

Muro, S., et al., "Endothelial Endocytic Pathways: Gates for Vascular Drug Delivery", "Current Vascular Pharmacology", 2004, pp. 281-299, vol. 2.

Muro, S., et al., "Control of intracellular trafficking of ICAM-1-targeted nanocarriers by endothelial Na+/H+ exchanger proteins", "Am J Physiol Lung Cell Mol Physiol", Nov. 18, 2005, pp. L809-L817, vol. 290.

Muro, S., et al., "Endothelial Targeting of High-Affinity Multivalent Polymer Nanocarriers Directed to Intercellular Adhesion Molecule 1", "The Journal of Pharmacology and Experimental Therapeutics", 2006, pp. 1161-1169, vol. 317, No. 3.

Sillerud, L., et al., "NMR solution structure of a potent cyclic nonapeptide inhibitor of ICAM-1- mediated leukocyte adhesion produced by homologous amino acid substitution", "J. Peptide Res.", 2004, pp. 127-140, vol. 64.

Smith, J., et al., "Identification of a *Plasmodium faciparum* intercellular adhesion molecule-1 binding domain: A parasite adhesion trait implicated in cerebral malaria", "PNAS", Feb. 15, 2000, pp. 1766-1771, vol. 97, No. 4.

Springer, A., et al., "Functional interdependence of the DBLbeta domain and c2 region for binding of the *Plasmodium falciparum* variant antigen to ICAM-1", "Molecular and Biochemical Parasitology", May 25, 2004, pp. 55-64, vol. 137.

Welply, J., et al., "A Peptide Isolated by Phage Display Binds to ICAM-1 and Inhibits Binding to LFA-1", "Proteins: Structure, Function, and Genetics", 1996, pp. 262-270, vol. 26.

Xu, C., et al., "Structural and ICAM-1-Docking Properties of a Cyclic Peptide from the I-domain of LFA-1: An inhibitor of ICAM-1/LFA-1-mediated T-cell adhesion", "Journal of Biomolecular Structure and Dynamics", 2002, pp. 789-799, vol. 19, No. 5.

NOTE: For the non-patent literature citations that no month of publication is indicated, the year of publication is more than 1 year prior to the effective filing date of the present application.

Gardiner, E., et al., "A Mitogenic Action for Fibrinogen Mediated through Intercellular Adhesion Molecule-1", "The Journal of Biological Chemistry", Jun. 13, 1997, pp. 15474-15480, vol. 272, No. 24.

Garnacho, C., et al., "A Fibrinogen-Derived Peptide Provides Intercellular Adhesion Molecule-1-Specific Targeting and Intraendothelial Transport of Polymer Nanocarriers in Human Cell Cultures and Mice", "The Journal of Pharmacology and Experimental Therapeutics", Mar. 2012, pp. 638-647, vol. 340, No. 3.

\* cited by examiner

```
                           SEQUENCE LISTING

<160> NUMBER OF SEQ ID NOS: 31

<210> SEQ ID NO 1
<211> LENGTH: 17
<212> TYPE: PRT
<213> ORGANISM: Artificial Sequence
<220> FEATURE:
<223> OTHER INFORMATION: fibrinogen-derived gamma-3

<400> SEQUENCE: 1

Asn Asn Gln Lys Ile Val Asn Leu Lys Glu Lys Val Ala Gln Leu Glu
1               5                   10                  15

Ala

<210> SEQ ID NO 2
<211> LENGTH: 17
<212> TYPE: PRT
<213> ORGANISM: Artificial Sequence
<220> FEATURE:
<223> OTHER INFORMATION: fibrinogen-derived 2-gamma-3

<400> SEQUENCE: 2

Asn Asn Gln Lys Ile Val Asn Ile Lys Glu Lys Val Ala Gln Ile Glu
1               5                   10                  15

Ala

<210> SEQ ID NO 3
<211> LENGTH: 17
<212> TYPE: PRT
<213> ORGANISM: Artificial Sequence
<220> FEATURE:
<223> OTHER INFORMATION: fibrinogen-derived 3-gamma-3

<400> SEQUENCE: 3

Asn Asn Gln Lys Leu Val Asn Ile Lys Glu Lys Val Ala Gln Ile Glu
1               5                   10                  15

Ala

<210> SEQ ID NO 4
<211> LENGTH: 60
<212> TYPE: DNA
<213> ORGANISM: Artificial Sequence
<220> FEATURE:
<223> OTHER INFORMATION: XmaI-ATG-gamma-3-SpeI-F oligonucleotide

<400> SEQUENCE: 4
ccgggatgaa taatcaaaag attgttaacc tgaaagagaa ggtagcccag cttgaagcaa    60
```

<210> SEQ ID NO 5
<211> LENGTH: 60
<212> TYPE: DNA
<213> ORGANISM: Artificial Sequence
<220> FEATURE:
<223> OTHER INFORMATION: XmaI-ATG-gamma-3-SpeI-R oligonucleotide

<400> SEQUENCE: 5
ctagttgctt caagctgggc taccttctct ttcaggttaa caatcttttg attattcatc    60

<210> SEQ ID NO 6
<211> LENGTH: 60
<212> TYPE: DNA
<213> ORGANISM: Artificial Sequence
<220> FEATURE:
<223> OTHER INFORMATION: XmaI-ATG-2-gamma-3-SpeI-F oligonucleotide

<400> SEQUENCE: 6
ccgggatgaa taatcaaaag attgttaaca tcaaagagaa ggtagcccag atcgaagcaa    60

<210> SEQ ID NO 7
<211> LENGTH: 61
<212> TYPE: DNA
<213> ORGANISM: Artificial Sequence
<220> FEATURE:
<223> OTHER INFORMATION: XmaI-ATG-2-gamma-3-SpeI-R oligonucleotide

<400> SEQUENCE: 7
ctagtttgct tcgatctggg ctaccttctc tttgatgtta acaatctttt gattattcat    60
c                                                                   61

<210> SEQ ID NO 8
<211> LENGTH: 60
<212> TYPE: DNA
<213> ORGANISM: Artificial Sequence
<220> FEATURE:
<223> OTHER INFORMATION: XmaI-ATG-3-gamma-3-SpeI-F oligonucleotide

<400> SEQUENCE: 8
ccgggatgaa taatcaaaag cttgttaaca tcaaagagaa ggtagcccag atcgaagcaa    60

<210> SEQ ID NO 9
<211> LENGTH: 60
<212> TYPE: DNA
<213> ORGANISM: Artificial Sequence
<220> FEATURE:
<223> OTHER INFORMATION: XmaI-ATG-3-gamma-3-SpeI-R oligonucleotide

<400> SEQUENCE: 9
ctagttgctt cgatctgggc taccttctct ttgatgttaa caagcttttg attattcatc    60

<210> SEQ ID NO 10
<211> LENGTH: 42
<212> TYPE: DNA
<213> ORGANISM: Artificial Sequence
<220> FEATURE:
<223> OTHER INFORMATION: SpeI-(Ser4Gly)2-EcoRI-F oligonucleotide

<400> SEQUENCE: 10
actagttctt cttcttctgg ctcttcttct tctggcgaat tc                       42

<210> SEQ ID NO 11
<211> LENGTH: 42
<212> TYPE: DNA

```
<213> ORGANISM: Artificial Sequence
<220> FEATURE:
<223> OTHER INFORMATION: SpeI-(Ser4Gly)2-EcoRI-R oligonucleotide

<400> SEQUENCE: 11
gaattcgcca gaagaagaag agccagaaga agaagaacta gt                    42

<210> SEQ ID NO 12
<211> LENGTH: 24
<212> TYPE: DNA
<213> ORGANISM: Artificial Sequence
<220> FEATURE:
<223> OTHER INFORMATION: EcoRI-ASM-F oligonucleotide

<400> SEQUENCE: 12
aattcccccg ctacggagcg tcac                                        24

<210> SEQ ID NO 13
<211> LENGTH: 25
<212> TYPE: DNA
<213> ORGANISM: Artificial Sequence
<220> FEATURE:
<223> OTHER INFORMATION: ASM-XbaI-R oligonucleotide

<400> SEQUENCE: 13
ctagactagc aaaacagtgg ccttg                                       25

<210> SEQ ID NO 14
<211> LENGTH: 7
<212> TYPE: PRT
<213> ORGANISM: Artificial Sequence
<220> FEATURE:
<223> OTHER INFORMATION: phage display-derived peptide A1

<400> SEQUENCE: 14

Tyr Pro Ala Ser Tyr Gln Arg
1               5

<210> SEQ ID NO 15
<211> LENGTH: 7
<212> TYPE: PRT
<213> ORGANISM: Artificial Sequence
<220> FEATURE:
<223> OTHER INFORMATION: phage display-derived peptide B7

<400> SEQUENCE: 15

Tyr Gln Ala Thr Pro Leu Pro
1               5

<210> SEQ ID NO 16
<211> LENGTH: 7
<212> TYPE: PRT
<213> ORGANISM: Artificial Sequence
<220> FEATURE:
<223> OTHER INFORMATION: phage display-derived peptide B8

<400> SEQUENCE: 16

Gly Ser Leu Leu Ser Ala Ala
1               5

<210> SEQ ID NO 17
<211> LENGTH: 7
<212> TYPE: PRT
<213> ORGANISM: Artificial Sequence
<220> FEATURE:
<223> OTHER INFORMATION: phage display-derived peptide B9
```

<400> SEQUENCE: 17

Phe Ser Pro His Ser Arg Thr
1               5

<210> SEQ ID NO 18
<211> LENGTH: 7
<212> TYPE: PRT
<213> ORGANISM: Artificial Sequence
<220> FEATURE:
<223> OTHER INFORMATION: phage display-derived peptide B10

<400> SEQUENCE: 18

Tyr Pro Phe Leu Pro Thr Ala
1               5

<210> SEQ ID NO 19
<211> LENGTH: 7
<212> TYPE: PRT
<213> ORGANISM: Artificial Sequence
<220> FEATURE:
<223> OTHER INFORMATION: phage display-derived peptide D6

<400> SEQUENCE: 19

Gly Cys Lys Leu Cys Ala Gln
1               5

<210> SEQ ID NO 20
<211> LENGTH: 30
<212> TYPE: DNA
<213> ORGANISM: Artificial Sequence
<220> FEATURE:
<223> OTHER INFORMATION: XmaI-ATG-A1-SpeI-F oligonucleotide

<400> SEQUENCE: 20
ccgggatgta ccccgccagc taccagcgga                              30

<210> SEQ ID NO 21
<211> LENGTH: 31
<212> TYPE: DNA
<213> ORGANISM: Artificial Sequence
<220> FEATURE:
<223> OTHER INFORMATION: XmaI-ATG-A1-SpeI-R oligonucleotide

<400> SEQUENCE: 21
ctagtccgct ggtagctggc ggggtacatc c                            31

<210> SEQ ID NO 22
<211> LENGTH: 30
<212> TYPE: DNA
<213> ORGANISM: Artificial Sequence
<220> FEATURE:
<223> OTHER INFORMATION: XmaI-ATG-D6-SpeI-F oligonucleotide

<400> SEQUENCE: 22
ccgggatggg ctgcaagctg tgcgcccaga                              30

<210> SEQ ID NO 23
<211> LENGTH: 30
<212> TYPE: DNA
<213> ORGANISM: Artificial Sequence
<220> FEATURE:
<223> OTHER INFORMATION: XmaI-ATG-D6-SpeI-R oligonucleotide

<400> SEQUENCE: 23
ctagtctggg cgcacagctt gcagcccatc                              30

<210> SEQ ID NO 24
<211> LENGTH: 30
<212> TYPE: DNA
<213> ORGANISM: Artificial Sequence
<220> FEATURE:
<223> OTHER INFORMATION: XmaI-ATG-B7-SpeI-F oligonucleotide

<400> SEQUENCE: 24
ccgggatgta ccaggccacc cccctgccca                                    30

<210> SEQ ID NO 25
<211> LENGTH: 30
<212> TYPE: DNA
<213> ORGANISM: Artificial Sequence
<220> FEATURE:
<223> OTHER INFORMATION: XmaI-ATG-B7-SpeI-R oligonucleotide

<400> SEQUENCE: 25
ctagtgggca gggggtggc ctggtacatc                                     30

<210> SEQ ID NO 26
<211> LENGTH: 30
<212> TYPE: DNA
<213> ORGANISM: Artificial Sequence
<220> FEATURE:
<223> OTHER INFORMATION: XmaI-ATG-B8-SpeI-F oligonucleotide

<400> SEQUENCE: 26
ccgggatggg cagcctgctg agcgccgcca                                    30

<210> SEQ ID NO 27
<211> LENGTH: 30
<212> TYPE: DNA
<213> ORGANISM: Artificial Sequence
<220> FEATURE:
<223> OTHER INFORMATION: XmaI-ATG-B8-SpeI-R oligonucleotide

<400> SEQUENCE: 27
ctagtggcgg cgctcagcag gctgcccatc                                    30

<210> SEQ ID NO 28
<211> LENGTH: 30
<212> TYPE: DNA
<213> ORGANISM: Artificial Sequence
<220> FEATURE:
<223> OTHER INFORMATION: XmaI-ATG-B9-SpeI-F oligonucleotide

<400> SEQUENCE: 28
ccgggatgtt cagcccccac agccggacca                                    30

<210> SEQ ID NO 29
<211> LENGTH: 30
<212> TYPE: DNA
<213> ORGANISM: Artificial Sequence
<220> FEATURE:
<223> OTHER INFORMATION: XmaI-ATG-B9-SpeI-R oligonucleotide

<400> SEQUENCE: 29
ctagtggtcc ggctgtgggg gctgaacatc                                    30

<210> SEQ ID NO 30
<211> LENGTH: 30
<212> TYPE: DNA
<213> ORGANISM: Artificial Sequence
<220> FEATURE:
<223> OTHER INFORMATION: XmaI-ATG-B10-SpeI-F oligonucleotide

```
<400> SEQUENCE: 30
ccgggatgta ccccttcctg cccaccgcca                                30

<210> SEQ ID NO 31
<211> LENGTH: 30
<212> TYPE: DNA
<213> ORGANISM: Artificial Sequence
<220> FEATURE:
<223> OTHER INFORMATION: XmaI-ATG-B10-SpeI-R oligonucleotide

<400> SEQUENCE: 31
ctagtggcgg tgggcaggaa ggggtacatc                                30
```

TARGETED CARRIERS FOR DRUG DELIVERY ACROSS THE GASTROINTESTINAL EPITHELIUM

CROSS-REFERENCE TO RELATED APPLICATIONS

This application is a continuation in part of U.S. application Ser. No. 13/376,362, filed Dec. 5, 2011, and published as U.S. Patent Application Publication No. 2012/0076730, which is the National Stage of International Application No. PCT/US2010/037490 filed Jun. 4, 2010, which claims the benefit of U.S. Provisional Application No. 61/184,657 filed Jun. 5, 2009 and further claims the benefit of U.S. Provisional Application No. 61/220,404 filed Jun. 25, 2009. The present application further claims the benefit of U.S. Provisional Application No. 61/481,779 filed May 3, 2011. The disclosures of such applications are hereby incorporated by reference in their respective entireties, for all purposes.

FIELD OF THE INVENTION

The present invention relates to novel ICAM-1-targeting moieties and methods of using the same in compositions for targeted oral delivery and transport of agents for research, analytical, diagnostic or therapeutic purposes.

DESCRIPTION OF THE RELATED ART

Oral administration of nutritional supplements, therapeutics, and other agents represents the most desirable route of delivery to the systemic circulation (Owen, R. L. *Semin. Immunol.* 11 (1999): 157-163; Hidalgo, I. J. & Borchardt, R. T., *Biochim. Biophys. Acta* 1028 (1990): 25-30; Artusson, P., *J. Pharma. Sci.* 79 (1990): 476-482.). Whereas intravenous delivery poses an inconvenience to healthcare professionals and causes patient discomfort due to its invasiveness, oral administration of therapeutic agents includes various benefits, such as increased patient compliance, reduction of cost, and a more flexible dosing regimen. However, in many cases, implementation of oral delivery needs to overcome crucial challenges of bioavailability (Chen, R. & Langer, R., *Adv. Drug Del. Rev.* 34, 2-3 (1998): 339-350.). This concept refers to the fraction of an administered drug that reaches the systemic circulation, determined by numerous factors, including the degree of gastrointestinal (GI) degradation, adhesion to the mucosa, and transport across the GI tract.

An important obstacle of orally administered agents that influences their bioavailability is the extent to which they adhere to the mucosa. This event, referred to as bioadhesion, occurs as a prerequisite to GI absorption. Substances must diffuse through the mucus layer, adhere to mucosal cells, and be transported across this cellular barrier into the blood (Ponchel, G. & Irache, J., *Adv. Drug Del. Rev.* 34 (1998): 191-219; Chen, R. & Langer, R., *Adv. Drug Del. Rev.* 34, 2-3 (1998): 339-350). Therefore, oral and GI delivery would benefit from strategies to surmount these obstacles.

In an attempt to circumvent the challenges associated with oral drug delivery and, most generally, with drug delivery via other administration routes, vehicles called carriers are currently being investigated to assist and improve the bioavailability of therapeutic agents (Chen, R. & Langer, R., *Adv. Drug Del. Rev.* 34, 2-3 (1998): 339-350; Bareford, L. & Swaan. P., *Adv. Drug Del. Rev.* 59 (2007): 748-758; Ghandehari, H. *Adv. Drug Del. Rev.* 60 (2008): 956; Kitchens, K. M., et al., *Adv. Drug Del. Rev.* 57 (2005): 2163-2176.). Carriers are macromolecular assemblies fabricated from a variety of materials, designed to carry therapeutic or diagnostic agents. Functions of carriers include solubilization of hydrophobic drugs, protection of drugs against inactivation and premature activity en route to the target, optimization of a drug's pharmacokinetics (including circulation and tissue distribution), fine control of drug-release kinetics, and control of drug metabolism and elimination. Key controllable parameters of carriers that define their utility for drug delivery include their chemistry, surface characteristics, morphology, size, shape, permeability, biocompatibility, and biodegradability A great diversity of carriers has been designed with this purpose, including (but not restricted to) nanotubes and other carbon nanostructures, linear polymers, branched dendrimers, phospholipid liposomes, and amphiphilic polymers formulated as self-assembled micelles or polymer particles (Torchilin, V., *Adv. Drug Del. Rev.* 58 (2006): 1532-1555; Ding, B. et al., *Mol. Interventions.* 6 (2006): 98-111; Lee, C. C., et al., *Nat. Biotechnol.* 23 (2005): 1517-1526; Ghandehari, H. *Adv. Drug Del. Rev.* 60 (2008): 956; Minko, T., et al. *Anticancer Agents Med. Chem.* 6 (2006): 537-552; Moghimi, S. & Szebani, J., *Prog. Lipid Res.* 42 (2003): 463-478; Hans, M. L. & Lowman, A. M., *Curr. Opin. Solid State Mater. Sci.* 6 (2002): 319-327; Discher, B. M., et al., *J. Phys. Chem. B.* 106, 11 (2002): 2848-2854; Panyam, J., & Labhasetwar, V., *Adv. Drug Del. Rev.* 55 (2003): 329-347; Dziubla, T. D. & Muzykantov, V., V Torchilin, Ed. Imperial College Press, London. (2006): 499-506.)

Although such carriers optimize the bioavailability and pharmacokinetics of drugs in the blood and protect drugs from degradation in the GI and the circulation, there still exist several problems associated with oral delivery of carriers. For instance, most enterocytes (as most other cell types) do not actively internalize and transport carriers across their body and, hence, across the GI epithelium, in a non-specific manner (Ponchel, G. & Irache, J., *Adv. Drug Del. Rev.* 34 (1998): 191-219.). Therefore, carriers which are not targeted to specific determinants in the epithelial layer are sub-optimally absorbed by the GI tract given their low bioadhesion. Rather than adhering to the intestinal cells, non-specific carriers remain in the mucus layer where they become detached due to mucus turnover and elimination through the feces. Therefore, carriers hold potential for increasing the bioavailability of therapeutic agents by protecting the drug from degradation in the gastrointestinal lumen (Ponchel, G. & Irache, J., *Adv. Drug Del. Rev.* 34 (1998): 191-219; Ghandehari, H. *Adv. Drug Del. Rev.* 60 (2008): 956; Chen, H. et al., *Pharm. Res.* 13, 9 (1996): 1378-1383), yet efficient delivery of carriers across the GI epithelium into the blood is still sub-optimal.

The utility of carriers can be further optimized by coupling them to molecules that have specific affinity for those sites in the body where the therapeutic agent needs to be delivered, which is referred to as targeted drug delivery. Coupling affinity-moieties (e.g., an antibody, a naturally-occurring ligand for the receptor or a functional derivative thereof, a vitamin, a hormone, a small molecule mimetic of a naturally-occurring ligand, a peptide, a polypeptide, a peptidomimetic, a carbohydrate, a lipid, an aptamer, a nucleic acid, a toxin, a component of a microorganism, or any other molecule provided it binds specifically to the cell surface molecule) with affinity to certain cell surface markers to the surface of carriers provides specific targeting, transport properties, and drug delivery capabilities. The concept of selecting an affinity ligand to specifically recognize a molecular marker or receptor can be applied to deliver therapeutics to a certain organ, tissue, or subcellular compartment. Indeed, when injected in the circulation, targeted carriers are capable of recognizing disease-specific sites, which decreases side effects in healthy tissues (Ding, B. et al., *Mol. Interventions.* 6 (2006): 98-111; Chen, H. et al., *Pharm. Res.* 13, 9 (1996): 1378-1383; Hamman, J. H., et al, *Drug Target Insights.* 2 (2007): 71-81; Muro, S. & Muzykantov, V. R., *Curr Pharm Des.* 11 (2005): 2383-2401.).

In the context of oral delivery, one advantage of targeted delivery systems is that they delay intestinal excretion of drugs by enhancing bioadhesion. Intestinal epithelial cells present a vast array of glycoproteins and glycolipids on the epithelial surface, which are readily available to molecules present in the intestinal lumen. Thus, any molecules which possess binding affinity for these markers could potentially be used to direct carriers to the epithelium and thereby prolong the contact or transit time in the GI (Russell-Jones. G. J., *Adv. Drug Deliv. Rev.* 46 (2001): 59-73; Chen, H. et al., *Pharm. Res.* 13, 9 (1996): 1378-1383; Yin, Y. & Chen, D., *J. Cont. Rel.* 123, 1 (2007): 27-38; Hamman, J. H., et al, *Drug Target Insights.* 2 (2007): 71-81.)

Significant progress in the identification of such cellular surface markers—both relatively selective for GI epithelial cells and more general molecules characteristic of several or many cell types in the body—is being achieved using techniques including phage display libraries and monoclonal antibodies (Muzykantov, V. *Expert Opin Drug Deliv* 2 (2005): 909-926; Oh, P, et al, *Nature* 2004; 429:629-35.). However, the utility of most of these newly identified candidate markers for drug delivery in humans remains to be tested. For example, functions of most cell surface markers defined by these modern techniques are either not known or are responsible for vital physiological processes in the body, hence inadvertent intervention into or blocking of their functions may lead to harmful side effects.

Targeted drug carriers are also more efficiently absorbed than their non-targeted counterparts because they may induce active transport pathways into and/or across cells. For example, carriers that target vitamin B12 receptors enhance oral drug delivery compared to their unconjugated counterparts, given that they utilize the B12 absorption pathway in enterocytes, which operates via receptor-mediated endocytosis (Hamman, J. H., et al, *Drug Target Insights.* 2 (2007): 71-81.). Such transport of substances and pathogens into cells and/or across cell layers (e.g., endothelial cells in the blood-brain barrier and epithelial cells in the GI tract) involves either the transcellular or paracellular route. The paracellular pathway involves transport of molecules across the junctions that interlock epithelial cells. This lateral domain of the epithelial barrier includes (i) the tight junctions, a branching network of sealing strands mainly composed of the proteins occludins and claudins, and (ii) anchoring junctions known to as adherens junctions, which maintain cell-cell adherence by linking transmembrane proteins on adjacent cells to the cytoskeleton (Dejana, E. *Nat. Rev. Mol. Cell. Biol.* 5 (2004): 261-270.). The paracellular transport requires disturbance of these junctions, through which materials are transported through the extracellular space. This may lead to the uncontrolled, passive and, hence, damaging transport of substances other than the drug in the GI.

In contrast to the paracellular pathway, the transcellular route does not cause disruption of the permeability barrier and, hence, is better suited for safe and controlled drug delivery (Predescu, D., et al., *Am. J. Physiol. Lung Cell Mol. Physiol.* 287 (2004): L895-L901; Pardridge W M. *Curr Opin Pharmacol* 2006; 6:494-500.). This route involves internalization of materials on the apical membrane in contact with the GI lumen via membrane invagination, traffic of endocytic vesicles across the enterocyte, and exocytosis at the basolateral membrane for delivery into the circulation (Predescu, D., et al., *Am. J. Physiol. Lung Cell Mol. Physiol.* 287 (2004): L895-L901; Pardridge W M. *Curr Opin Pharmacol* 2006; 6:494-500.). This type of transport is mediated by endocytosis. The endocytic pathways include: (i) macropinocytosis, a mechanism allowing uptake of extracellular fluid into large micrometer size vesicles, (ii) phagocytosis involves uptake of large particulate ligands via formation of large endocytic vesicles called phagosomes, (iii) clathrin-mediated endocytosis is triggered by binding of specific ligands to their receptors in the plasma membrane, leading to internalization of extracellular macromolecules along with extracellular fluid into vesicles coated by the cytosolic protein, clathrin (clathrin-coated pits), and (iv) caveolin-mediated endocytosis, characterized by uptake of materials into flask-shape vesicles enriched on the protein caveolin-1, which occurs in areas of the membrane where the lipid bilayer is enriched in cholesterol and glycolipids (Muro, S., et al. *Curr. Vasc. Pharm.* 2 (2004): 281-299.).

However, some of these natural pathways, e.g., macropinocytosis and phagocytosis, are typically associated to cells of the immune system, precluding targeting and delivery to other cell types in the body (Muro, S., et al. *Curr. Vasc. Pharm.* 2 (2004): 281-299.). In addition, all these pathways have been found to be suppressed in certain types of human pathology including inflammation, metabolic disorders, ischemia and abnormalities of blood flow, negatively impacting delivery in the setting in which drugs are needed in the tissues (Dermaut B, et al. *J Cell Biol* 2005; 170:127-39; Dhami R, & Schuchman E H. *J Biol Chem* 2004; 279:1526-32; Monroy M A, et al. *Bone* 2002; 30:352-9; Pol A, et al. *Mol Biol Cell* 2005; 16:2091-105; Puri V, et al. *Nat Cell Biol* 1999; 1:386-8.).

Also, intracellular and transcellular transporting capacity of clathrin- and caveolar-mediated pathways common to most cell types in the body (e.g., exploited by targeting to manose-6-phosphate receptor, glucose receptors, LDL-family receptors, receptor associated protein RAP, insulin-like growth factor II, transferrin, insulin, folate receptor, and other receptors), is restricted to relatively small objects, typically <100 nm in diameter (Muro, S., et al. *Curr. Vasc. Pharm.* 2 (2004): 281-299; Pardridge W M. *Curr Opin Pharmacol* 2006; 6:494-500; Schnitzer J E, *Adv Drug Deliv Rev* 2001; 49:265-80.). For instance, phage particles (~800 nm length) targeted to pulmonary caveolar determinants simply do not bind to their intended targets due to inaccessibility of caveolar determinants for objects larger than 50-80 nm, from the circulation (Oh et al., 2007) This fact restricts transport of many emerging targeted drug and diagnostic delivery systems (100 nm-1 μm) with promising applications in virtue of their high affinity and payload.

Finally, even if these obstacles are overcome, the transported carriers must be able to then transport their cargoes (therapeutics and/or diagnostic agents) through the circulation to the different organs, tissues, cell types, and subcellular compartments in the body where their action is required. Therefore, such carriers must be targeted to markers that are present not only on GI epithelial cells but also cells in the blood vessel wall and cells within the different tissues and organs in the body, primarily on sites affected by disease. Ultimately, safe targeting moieties much be available to target such carriers across the GI epithelium and to all these body destinations in a safe manner, e.g., relatively "invisible" and innocuous to the body to avoid secondary detrimental reactions, particularly if recurrent administrations are necessary for an effective treatment.

There therefore remains a need in the art for targeting moieties and compositions comprising such targeting moieties for safe and controlled delivery via the gastrointestinal tract, where the targeting moieties effectively target GI epithelial cells, and are transported across the GI epithelial layer with no effect on the GI permeability and further provide systemic availability of the composition. The present invention provides such methods and compositions.

SUMMARY OF THE INVENTION

This invention relates to the use of targeting moieties effective as targeting molecules providing efficient and specific binding of compositions containing therapeutic agents and drug delivery systems to a determinant present in both mice and humans, e.g. for delivery to the surface of a cell and/or effective and safe transport into and/or across cells. In one aspect the targeting moieties are short peptides derived from fibrinogen, a natural protein present in the human circulation. In another aspect the targeting moieties are anti-ICAM-1 antibodies.

The present invention relates to a composition for oral administration to a subject, the composition comprising a targeting moiety comprising an anti-ICAM antibody; and an agent, wherein the targeting moiety recognizes and binds to ICAM-1 on a GI epithelial cell and the composition is transported across the GI epithelium. In various aspects, the composition may further comprise a delivery carrier, a protective agent and/or a second or additional targeting moiety.

In another aspect the invention relates to a method for delivery of an agent across the gastrointestinal epithelium, comprising oral administration of a composition comprising a targeting moiety selected from SEQ ID NO:1, SEQ ID NO:2, SEQ ID NO:3, SEQ ID NO:14, SEQ ID NO:15, SEQ ID NO:16, SEQ ID NO:17, SEQ ID NO:18, SEQ ID NO:19, and an anti-ICAM antibody; and an agent, wherein the targeting moiety recognizes and binds to a target on a gastrointestinal epithelial cell and the composition is transported across the gastrointestinal epithelium.

A further aspect of the invention relates to a targeting moiety specific for targeting ICAM-1, the targeting moiety selected from SEQ ID NO: 1, SEQ ID NO: 2, SEQ ID NO: 3, SEQ ID NO: 14, SEQ ID NO: 15, SEQ ID NO: 16, SEQ ID NO: 17, SEQ ID NO: 18, SEQ ID NO: 19 and an anti-ICAM antibody.

Other aspects, features and embodiments of the invention will be more fully apparent from the ensuing disclosure and appended claims.

BRIEF DESCRIPTION OF THE DRAWINGS

FIG. 2D is a graph of location of the carriers, as a function of their size.

FIG. 4B provides a graph demonstrating the effects of blocking ICAM-1 or other molecules on the binding of γ3 carriers with ASM cargo and binding to cells that do not express ICAM-1; FIGS. 4C-E FIG. 22 provides an illustration of a polymer coated carrier, protected from detection by the immune system.

DETAILED DESCRIPTION OF THE INVENTION AND PREFERRED EMBODIMENTS THEREOF

Figure 1:
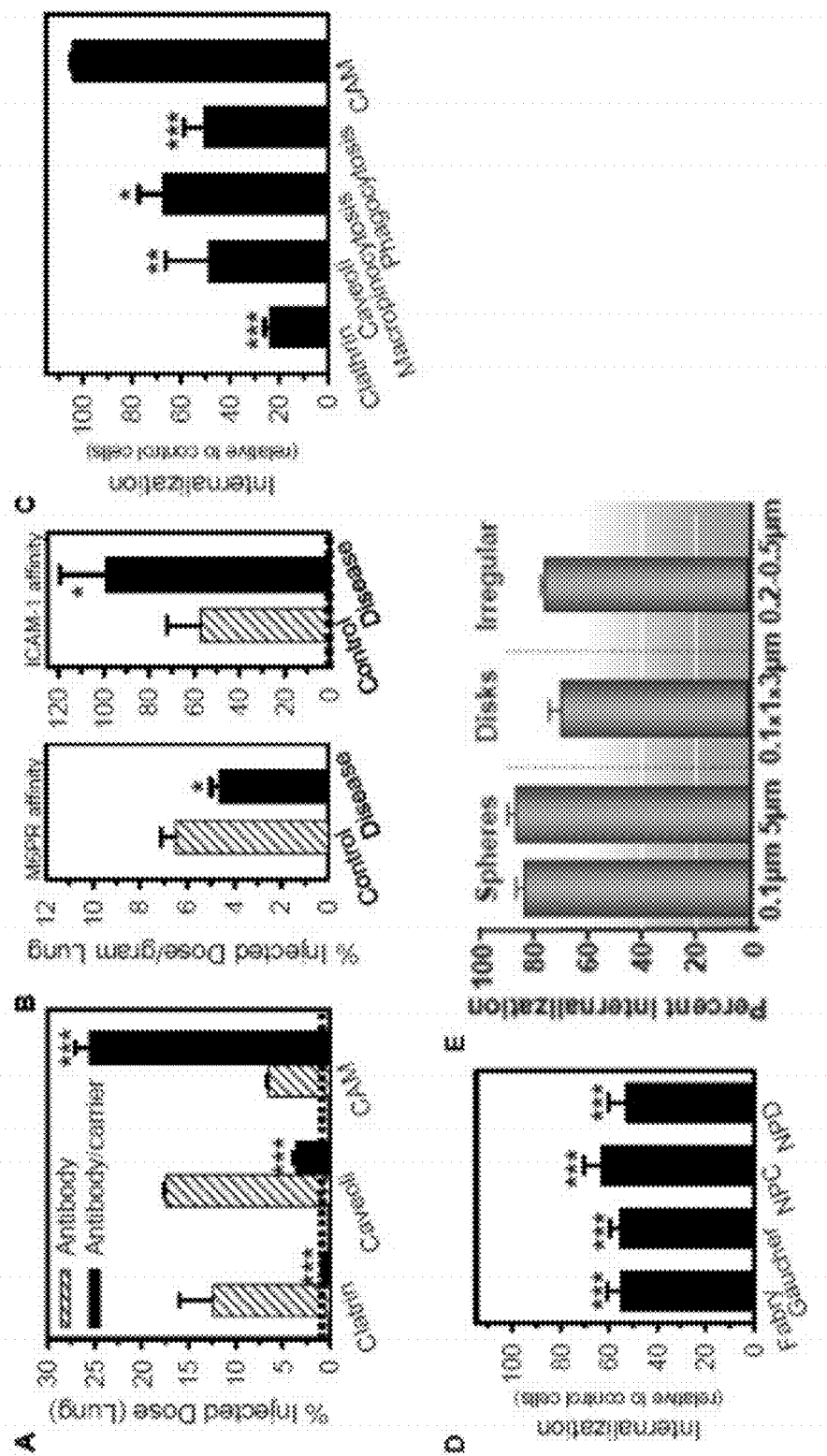
FIG. 1 illustrates the results of Example 1, comparing the in vivo accessibility and internalization in cells, of free anti-ICAM and anti-ICAM carriers, in vivo and in cell cultures, in normal and disease conditions, via ICAM-1 and CAM-mediated endocytosis, as compared to endocytosis mediated by clathrin, caveoli, macropinocytosis and phagocytosis.

The present invention relates to targeting moieties used to provide more effective, versatile, and safe targeting and transport of molecular probes, diagnostic and therapeutic agents and/or their carriers. The moieties provided are useful in both research settings and in the context of translational science and clinical interventions. The invention further relates to compositions containing such targeting moieties and to methods of using such target moieties.

"Targeting moiety" as used herein refers to moieties useful in the compositions and methods described herein, wherein the moieties specifically target a surface expressed protein, e.g., ICAM-1. In one embodiment the targeting moieties mediate efficient and specific delivery of an agent to a determinant through such targeting. Targeting moieties and/or their carriers may be varied, such as by size, shape, and/or valency in order to modulate delivery. A targeting moiety may also be described herein as any of an "affinity moiety," an "affinity peptide," a "targeting peptide," "targeting molecule," or "ligand."

"Carrier" as used herein refers to an accessory substance present as a vehicle during the transfer of an active substance to a target. In one embodiment, the targeting moieties are carriers for the agents. As such, the targeting moieties may also be referred to herein as "targeting carriers." In another embodiment, "delivery carriers" are provided for transfer or delivery of a composition containing the targeting moiety and/or the agent to the target. A delivery carrier may also function to protect the targeting moiety and/or the agent between the time of administration and the time of arrival at the locus of the target. In such an embodiment the delivery carrier may alternately be referred to as a "protective agent."

"Agent" as used herein refers to the subject of the targeting or transport of the targeting moiety. In conjunction with the action of the targeting moiety, agents may be transported to a cell, to the surface of a cell, into a cell or across a cell. Specifically, the targeting moiety provides a means for transporting agents such as, but not limited to, research, analytical, reporter or molecular probes, diagnostic and therapeutic agents, biologically active agents, research agents, analytical agents, imaging agents, monitoring agents, enzymes, proteins, peptides, nucleic acids, lipids, sugars, hormones, lipoproteins, chemicals, viruses, bacteria, cells, including modified cells, biosensors, markers, antibodies and ligands. An agent may also be described herein as a "cargo."

"Target" as used herein refers to a determinant recognized by the targeting moiety. In one embodiment a target recognized by this targeting moiety is a molecule expressed on the surface of a cell which constitutes a part of the first layer after administration within a tissue. Such cells are therefore easily accessible. Examples of such cells include, but are not limited to, endothelial cells in the context of preferable intravascular (intravenous or intra-arterial) administration; epithelial cells in the case of gastrointestinal, nasal, intratracheal, or rectal administration; immune system cells for treatment of conditions affecting these cells; muscle cells for intramuscular administration; glial cells and neurons for intra-cerebral or intrathecal administration and the like. Expression of the target molecule in normal physiological conditions would provide a target for protective or prophylactic interventions, whereas up-regulation of the expression of the molecule in many pathologies would provide a target for site-specific interaction with the composition, such as delivery of therapeutic and diagnostic agents to disease sites and/or cell-specific transport of the composition, including, but not limited to surface residency, intracellular transport and transcellular transport of the composition and/or agent. In another embodiment a target recognized by the targeting moiety may be a tissue or an organ. A target may also be described herein as a "target molecule," a "determinant," or a "receptor."

Where the target molecule is expressed on the surface of a cell, it should be stably expressed on the cell surface to allow sufficient time frame for targeted interventions. If the cell surface is the intended destination for a composition or agent, the target molecule should remain on the cell surface. If the interior of the cell is the intended destination for a composition or agent, the target molecule should provide internalization within the cell body or safe transport across cellular layers (e.g., by an endocytic pathway or transcytosis, respectively) upon proper induction by targeting. Such internalization may be used for intracellular delivery of agents to the cell interior or transcellular delivery for penetration across cell layers or tissues. In a particular embodiment the invention provides a method of CAM-mediated cytosis of a composition across the GI epithelial layer.

The physiological function of the target molecule is not detrimental (and, preferably is beneficial) to the interaction of the agent with the target molecule and/or the biological, physiological, or pathological function of the target molecule. The mechanism associated with interaction of the agent and the target molecules resulting in any of surface residency, intracellular transport or transcellular transport should be not affected by disease, and the parameters of such interaction should be known, to allow rational design of strategies for delivery of therapeutic and/or diagnostic agents with precision.

In one embodiment the invention provides a composition including a targeting moiety, where the targeting moiety recognizes and binds to a target on a cell. A composition of the invention may optionally include two or more targeting moieties, where the two or more targeting moieties may react with their targets simultaneously or sequentially but, preferably, do not compete for a particular target. Optionally, the composition may further comprise a delivery carrier. Still further, the composition may optionally comprise a protective agent to protect the composition e.g., from degradation in the digestive system or from detection by the immune system. In another embodiment the composition includes a nucleic acid encoding a targeting moiety, where the targeting moiety, when expressed, recognizes and binds to a target on a cell.

In still another embodiment the invention provides a composition for delivery of an agent to a cell, where the delivery composition includes both a targeting moiety and one or more agents, where the targeting moiety recognizes and binds to a target on a cell and is effective to deliver the agent to the cell. Optionally, the composition may further comprise a delivery carrier. In a further embodiment, the invention provides a composition for delivery of an agent to a cell, where the delivery composition includes both a nucleic acid encoding a targeting moiety and a nucleic acid encoding an agent, where the targeting moiety, when expressed, recognizes and binds to a target on a cell and is effective to deliver the agent to the cell. Expression of the agent may be co-expression with the targeting moiety or may be separately expressed.

Expression and production systems as described above may include, but are not limited to, viruses, bacteria, and eukaryotic cells expressing and producing the targeting moieties and/or the agents.

In an exemplary embodiment, the inventors explored the utility as a targeting moiety of a 17 amino acid peptide derived from the γ chain of fibrinogen and its cleavage product fibrin, known as γ3, (Altieri D. C., et al., *J. Biol. Chem.* 1995; 270:696-9; D'Souza S. E., et al., *J. Biol. Chem.* 1996; 271: 24270-7; Duperray A., et al., *J. Biol. Chem.* 1997; 272:435-41; Languino, L. R., et al., *Cell* 1993; 73:1423-34.) and two peptides derived from γ3, derivatives termed 2γ3 and 3γ3. Fibrinogen is a dimer of three pairs of disulfide-bonded chains (Aα, Bβ, and γ) arranged in three globular domains (a central E domain and two peripheral D domains). (Weisel J. W., *Adv. Protein Chem.* 2005; 70:247-99.) Cleavage by thrombin of fibrinopeptides A and B from the amino-terminus of chains Aα and Bβ, converts fibrinogen into fibrin and exposes polymerization sites for forming fibrin mesh, typically involved in blood clotting. Both fibrinogen and fibrin form a molecular bridge between endothelial ICAM-1 and leukocyte β2 integrin Mac-1, which is the main function attributed to ICAM-1 in regard to fibrinogen/fibrin interaction: strengthening of the adhesion between these two cell types during inflammation.

Although the γ3 sequence within the fibrinogen/fibrin γ chain has been demonstrated to bind to human ICAM-1, none of native fibrinogen, fibrin, the γ chain, or the γ3 peptide had been coupled to or tested in the context of targeting therapeutic or diagnostic agents or their carriers to ICAM-1, or any other cell surface determinant, prior to the present invention. In addition, they had not been observed to affect cellular transport, for example internalization by cells by induction of CAM-mediated endocytosis or by any other method, and the potential recognition of ICAM-1 in other species (e.g., mouse) by the γ3 peptide was unknown. Prior to the inventors' work, potential use of γ3 for safe and efficient ICAM-1 targeting and delivery of therapeutic and diagnostic compounds, and their carriers, was unpredictable and unlikely.

γ3, 2γ3 and 3γ3 were examined as targeting moieties with regard to targeting therapeutic agents to the surface molecule "intercellular adhesion molecule 1" (ICAM-1). Therefore, in one embodiment of the invention, the targeting moiety is selected from γ3 (amino-terminus NNQKIVNLKEKVAQLEA carboxyl-terminus (SEQ ID NO: 1)), 2γ3 (amino-terminus NNQKIVNIKEKVAQIEA carboxyl-terminus (SEQ ID NO: 2)), and 3γ3 (amino-terminus NNQKLVNIKEKVAQIEA carboxyl-terminus (SEQ ID NO: 3)), short peptides derived from fibrinogen, a natural protein present in human circulation, which retain their affinity and selectivity for particular target determinants, particularly ICAM-1.

As can be seen from SEQ ID NOs: 2 and 3, peptides 2γ3 and 3γ3 are derivatives of γ3. Peptides 2γ3 and 3γ3 both retain the affinity and selectivity for ICAM-1, as demonstrated by γ3. In another embodiment of the invention, the targeting moiety is an additional variant or derivative of γ3, wherein the variant or derivative is truncated or extended with respect to SEQ ID NO: 1 and/or contains one or more amino acid substitutions, deletions, insertions, and/or additions relative to SEQ ID NO: 1. Such a targeting moiety retains affinity and selectivity for particular target determinants, such as ICAM-1. Accordingly, targeting moieties as described herein may include peptidomimetics of any of γ3, 2γ3, or 3γ3 their nucleotide encoding sequences, and the viral, bacterial, or cellular systems expressing and/or producing these peptides.

In a further embodiment, the inventors explored the utility as a targeting moiety of various very short chain peptides developed utilizing phage display. From such investigation a battery of 7 amino acid peptides (termed A1, B7, B8, B9, B10 and D6) was determined to be individually useful as targeting moieties in targeting of ICAM-1. Therefore, in one embodiment of the invention, the targeting moiety is selected from A1 (amino-terminus YPASYQR carboxyl-terminus (SEQ ID NO: 14)), B7 (amino-terminus YQATPLP carboxyl-terminus (SEQ ID NO: 15)), B8 (amino-terminus GSLLSAA carboxyl-terminus (SEQ ID NO: 16)), B9 (amino-terminus FSPHSRT carboxyl-terminus (SEQ ID NO: 17)), B10 (amino-terminus YPFLPTA carboxyl-terminus (SEQ ID NO: 18)), D6 (amino-terminus GCKLCAQ carboxyl-terminus (SEQ ID NO: 19)), phage display-derived peptides. In another embodiment, the targeting moiety is an additional variant or derivative of any of A1, B7, B8, B9, B10 and D6, wherein the variant or derivative is truncated or extended with respect to any of SEQ ID NO: 14-19 and/or contains one or more amino acid substitutions, deletions, insertions, and/or additions relative to any of SEQ ID NO: 14-19. Such a targeting moiety retains affinity and selectivity for particular target determinants, such as ICAM-1. Accordingly, targeting moieties as described herein may include peptidomimetics of any of A1, B7, B8, B9, B10 and D6 their nucleotide encoding sequences, and the viral, bacterial, or cellular systems expressing and/or producing these peptides.

Phage-display technology was utilized to identify small 7-mer random sequence peptides capable of recognizing ICAM-1. Although this technique has been proven in the past regarding identification of peptides with recognition properties, classically phage-display of larger random peptide sequences is used, (e.g., >12 amino acids) to increase chances of specific recognition of a determinant. Importantly, although targeting peptides can be generated by this method, whether these peptides have the ability to induce (upon binding to their surface determinants) cellular signals to induce transport into and/or across cells is totally unpredictable. The importance of this is demonstrated in a recent publication by the present inventors (Garnacho et al., 2008, Journal of Controlled Release, 130:226-233), which indicates that binding of targeting moieties to different epitopes or regions of the same determinant may lead to surface retention of drug carriers, their endocytic transport, and/or differential intracellular destination, even when the targeted epitopes are in close proximity or even overlapping. Moreover, some targeting moieties do not bind to their targets after coupling them to carriers (Garnacho et al., 2008, Journal of Controlled Release, 130:226-233).

Targeting moieties that are proteins or peptides may be obtained by any method known to those of skill in the art. Specifically, such proteins or peptides may be synthetic or recombinant or may be isolated from a naturally-occurring source or may be identified by phage display. Isolation of proteins or peptides of the invention so identified may be performed by any known method, including use of oligonucleotides, such as those described in Example 8 below.

In one embodiment, the targeting moiety is a protein or peptide expressed from a polynucleotide or expressed from an expression plasmid containing a polynucleotide encoding the protein or peptide. Furthermore the invention includes nucleic acid sequences that encode a targeting moiety selected from γ3, derivatives of γ3 (e.g., 2γ3 or 3γ3), A1, B7, B8, B9, B10, and D6. The invention also includes nucleic acid sequences that encode a peptide of any of SEQ ID NO: 1, 2, 3, 14, 15, 16, 17, 18 or 19. In another embodiment, the targeting moiety is a protein or peptide expressed from a nucleic acid sequence.

Targeting moieties of the invention may be monomeric, dimeric, tetrameric, or any other oligomeric form.

In another embodiment of the invention, the composition comprises more than one targeting moiety, where the composition comprises a targeting moiety that is one or more of γ3, 2γ3, and 3γ3, a variant, derivative or peptidomimetic of γ3, 2γ3, or 3γ3, A1, B7, B8, B9, B10, D6, a variant, derivative or peptidomimetic of A1, B7, B8, B9, B10, or D6, in combination with an antibody, an aptamer, a nucleic acid, a peptide, a carbohydrate, a lipid, a vitamin, a toxin, a component of a microorganism, a hormone, a receptor ligand and any derivative thereof.

In a further embodiment the invention provides a viral, non-viral, bacterial or cell system containing, encoding, expressing, and/or producing a targeting moiety. Such systems may also, optionally, further contain, encode, express, and/or produce an agent. Nucleic acid sequences encoding one or more targeting moieties and/or one or more agents may be present on the same nucleotide sequence or may be present on different nucleotide sequences. Expression of the agent may be co-expression with the targeting moiety or may be separately expressed.

In a still further embodiment, the targeting moiety recognizes a specific target. Such a specific target may include, but is not limited to an antigen or a receptor. In one particular embodiment the specific target is ICAM-1. In one embodiment of the invention, the targeting moiety recognizes both a molecular target isoform present in an animal model (e.g., mice) and also recognizes the human isoform. Preferably the targeting moiety demonstrates an affinity for both human and mouse ICAM-1.

Binding of the targeting moiety to its target molecule on the cell surface is contemplated by the invention for tunable drug carrier delivery and/or transport on the cell surface, intracellularly or transcellularly, as well as interaction with the cell surface target providing secondary protective and/or beneficial effects, e.g., blockage of ICAM-1 binding to leukocytes, fibrinogen/fibrin, and/or pathogens.

In one embodiment the invention provides a delivery composition that comprises a targeting moiety that is capable of binding to ICAM-1. In a further embodiment the targeting moiety binds to human and/or mouse ICAM-1.

The binding of the targeting moiety and ICAM-1 or the transfection, expression, or production of the ICAM-1-targeting moiety may occur in any of cell culture, in vivo, ex vivo or in vitro. The binding may occur such that the targeting moiety binds to and remains on or at the cell surface, such that the targeting moiety binds to and is internalized by cells, or such that the targeting moiety is transported across the cells. Where the targeting moiety is internalized by the cells or transported across the cells, such internalization or transport may progress by any suitable mechanism, including, but not restricted to, endocytosis mechanisms, such as, but not restricted to, CAM-mediated endocytosis.

As a part of fibrinogen/fibrin, γ3 is constitutively present in the circulatory system. Binding of γ3 to ICAM-1 has been shown to decrease inflammation, it has been postulated that γ3 may attenuate atherosclerosis, cancer, and ICAM-1-dependent infections, and there is evidence that γ3 promotes cell survival and anti-apoptotic effects in activated endothelial cells. ICAM-1 is involved in and/or contributes to a variety of maladies or disorders. Such involvement or contribution may include interactions such as binding to ICAM-1, ICAM-1 function, ICAM-1 signaling, CAM-mediated endocytosis (see below) or, generally, ICAM-1-mediated pathways or pathways including ICAM-1 function (where ICAM-1 contributes either solely or in addition to other molecules). Such maladies or disorders include, but are not limited to, inflammation, immune diseases, thrombosis, oxidative stress, and/or certain pathogens, such as acute lung injury, acute respiratory distress syndrome, pulmonary thromboembolism, acute myocardial infarction, ischemic stroke, peripheral vascular pathology, deep vein thrombosis, atherosclerosis, hypertension, diabetes, cancer, AIDS, flu, common cold, poliomyelitis, and malaria.

Accordingly, delivery compositions of the invention, comprising γ3, variants or derivatives thereof (e.g., 2γ3 or 3γ3), A1, B7, B8, B9, B10, and/or D6 are effective in treating such conditions, disorders or maladies. Specifically, in one embodiment, a delivery composition is effective to inhibit inflammation. In another embodiment, a delivery composition of the invention is effective to inhibit lodging of an embolus or inhibit other occlusion of a blood vessel by lodging in the vasculature. Delivery compositions of the invention may also be effective in treating conditions such as bacterial infection, cancer and atherogenesis. The Examples as described herein and set forth in detail below demonstrate the successful conversion of γ3 and phage-display derived peptides into targeting molecules to drive binding, intracellular and transcellular transport of therapeutics and their carriers to cells, and block adhesion of objects to ICAM-1. The Examples further demonstrate the successful inhibition of inflammatory transmigration of leukocytes across endothelial cells and successful in vivo demonstration of inhibition of lodging of fibrin microemboli in the vasculature using compositions of the invention.

As described herein, the invention provides a composition comprising a targeting moiety. In one embodiment the composition is for delivery of an agent to a cell, where the delivery composition includes both a targeting moiety and one or more agents, where the targeting moiety recognizes and binds to a target on a cell and is effective to deliver the agent to the cell. In a further embodiment, the invention provides a delivery composition that includes one or more targeting moieties (recognizing the same or different targets, in the same or different cells) and one or more agents, where one or more of the targeting moieties recognizes and binds to a target on a cell, tissue or organ and is effective to deliver the agent to the cell, tissue or organ.

Target locations may include, but are not limited to, targeting of the kidneys, the spleen, the heart, the lungs, the liver or the brain, and targeting of cells or tissues present in or derived from such organs. The Examples provided herein demonstrate successful in vivo brain transport of therapeutic agent-containing delivery compositions of the invention.

In one embodiment the invention provides a composition comprising an agent such as, but not limited to, research, analytical or molecular probes, diagnostic and therapeutic agents, biologically active agents, research agents, analytical agents, imaging agents, monitoring agents, enzymes proteins, hormones, lipids, sugars, nucleic acids, lipoproteins, and chemicals. In another embodiment, where the agent is an enzyme, it comprises a lysosomal enzyme or encodes for a lysosomal enzyme. Such a lysosomal enzyme may be selected from the enzymes involved in Pompe Disease, GM1 gangliosidosis, Tay-Sachs disease, GM2 gangliosidosis, Sandhoff disease, Fabry disease, Gaucher disease, metachromatic leukodystrophy, Krabbe disease, Niemann-Pick disease type A, Niemann-Pick disease type B, Niemann-Pick disease type C, Niemann-Pick disease type D, Farber disease, Wolman disease, Hurler Syndrome, Scheie Syndrome, Hurler-Scheie Syndrome, Hunter Syndrome, Sanfilippo A Syndrome, Sanfilippo B Syndrome, Sanfilippo C Syndrome, Sanfilippo D Syndrome, Morquio A disease, Morquio B disease, Maroteaux-Lamy disease, Sly Syndrome, α-mannosidosis, β-mannosidosis, fucosidosis, aspartylglucosaminuria, sialidosis, mucolipidosis II, mucolipidosis III, mucolipidosis IV, Goldberg Syndrome, Schindler disease, cystinosis, Salla disease, infantile sialic acid storage disease, Batten disease, infantile neuronal ceroid lipofuscinosis, and prosaposin. In one embodiment of the invention the agent is acid sphingomyelinase.

The composition may further comprise a delivery carrier for the targeting moiety and/or the agent. In one embodiment, such a delivery carrier is selected from a natural virus or derived viral-like particle, dendrimer, carbon nanoassembly, liposome, a polymer carrier, a microbubble, a paramagnetic particle, a ferromagnetic particle, a self-assembled polymer, a polymersome, a filomicelle, a micelle, a micro particle or nanoparticle, an albumin particle, and/or a lipoprotein.

The elements of the composition may be varied, such as by size and shape, to modulate transport of the composition from the plasma membrane into or across the cells.

In one embodiment the targeting moiety is selected by its size, wherein the size is optimized for delivery to particular destination(s) within a cell. Targeting may be directed to loci such as the lysosome, endosomes, or pathways mediating transport from inside of a target cell to the surface of the cell. Therefore, in one embodiment, the targeting moiety is either below 1 μm size or larger than 1 μm size.

In one embodiment the composition further comprises sodium proton exchanger 1 (NHE1) inhibitors (such as amiloride) or protein kinase C activators (such as phorbol esters) to modulate transport.

Within the composition, the interaction of the elements may occur in a manner providing the most efficient reaction with the target. Accordingly, the interactions may include, but are not limited to, any of the following: the targeting moiety may be coupled to the delivery carrier, the agent may be coupled to the targeting moiety, the agent may be coupled to the delivery carrier, and/or the agent may be coupled to both the targeting moiety and the delivery carrier. The coupling of the elements of the composition may be any effective means of linking, binding, or conjugating the elements. Such interactions may include, but are not limited to, covalent binding, non-covalent binding, binding as a single entity, or binding in combination with one or more other elements of the composition.

The data described herein and reported in the Examples below demonstrate that materials of very different nature and chemistry, size and geometry can safely and efficiently access both human and mouse ICAM-1 when targeted by any of γ3, 2γ3, 3γ3, A1, B7, B8, B9, B10, and D6 and deliver viruses, carriers and agents to the cell surface, as well as into and across cells, via a pathway including ICAM-1 function, operative in a variety of cell types in control and disease conditions.

In one embodiment the invention provides compositions and methods useful in both laboratory experimentation and clinical endeavors. The compositions and methods of the invention are applicable in in vivo, ex vivo and in vitro applications, including cell cultures, animal models, human application or administration, and the like.

Comparison was made of γ3, 2γ3, 3γ3, A1, B7, B8, B9, B10, and D6 expressed onto viruses or coupled to prototype polystyrene carriers, biodegradable FDA-approved material-PLGA carriers, and carriers bearing therapeutic enzymes (recombinant acid sphingomyelinase, ASM) vs IgG-, anti-ICAM- and γ3-derived or A1-derived scramble peptide counterparts and ligands of classical endocytic pathways, and non-targeted counterparts, in terms of binding, transport, and effects, both in cell cultures and animal models.

In Example 1, in vivo accessibility of ICAM-1 was compared to that of determinants of clathrin and caveolar pathways, which also mediate transport into and across cells. As an example, antibodies to transferrin receptor and GM1, associated to clathrin pits and caveoli, only gained access to lung endothelium when injected iv in mice as free counterparts, not on 180 nm carrier particles (FIG. 1A), likely due to size limits of clathrin pits and caveoli and/or distribution of their receptors. ICAM-1 was accessible to both free targeting moieties (antibodies) and preferential carriers, which were specific against control IgG carriers (FIG. 1A). ICAM-1 targeting increased in a disease mouse model (ASM knockout (KO) mice), likely due to ICAM-1 overexpression described in many pathologies, while accumulation of free ASM, an enzyme that binds to mannose-6-phosphate receptor associated to classical clathrin pathways, was 10-fold lower and was further decreased in the disease model (FIG. 1B). This could be due to reduced endocytic uptake via classical pathways in disease conditions, as Niemann-Pick A/B-patient cells and ASMKO-mice cells had reduced uptake of ligands, toxins, and particles by clathrin pits, caveoli, macropinocytosis, and phagocytosis (FIG. 1C). Endocytic defects were also observed in other diseases, including Fabry, Gaucher and Niemann-Pick C (FIG. 1D). Yet, CAM-endocytosis of ICAM-1-targeted carriers was as efficient as in control cells (FIG. 1C). Also, ICAM-1-targeted particles of various sizes (up to 5 μm) and shapes (spheres, elliptical disks, and polymorphous conjugates) could access ICAM-1 targets in vivo and be efficiently endocytosed in cell culture (FIG. 1E).

In Example 2, ICAM-1-targeting moieties were shown to stably target the cell surface (anti-ICAM in FIG. 2A) and intracellular compartments (anti-ICAM polystyrene nanocarriers in FIG. 2B) in cell culture, as well as in vivo after iv injection in mice (anti-ICAM polystyrene carriers in endosomes and lysosomes in FIG. 2C left), where they were also safely transported across endothelial cells layers transcellularly without disruption of the cell junctions (FIG. 2C right). The final destination of these carriers, to compartments within the cell or re-surfacing to the exterior of the cell (adequate for intracellular vs transcellular delivery) can be controlled by the size of the carriers (FIG. 2D).

Figure 3:
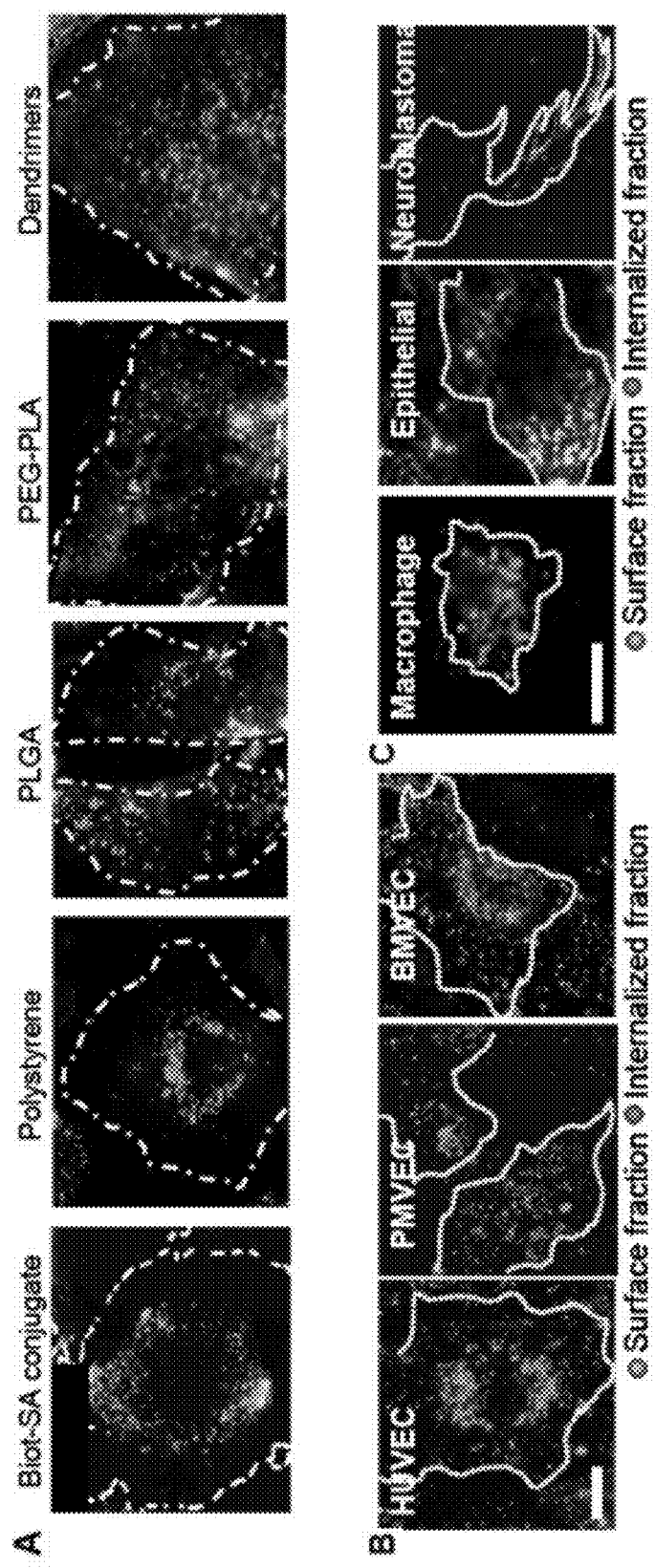
FIG. 3 illustrates the results of Example 3, showing efficient targeting and internalization of various delivery compositions and various cell types.

Example 3 demonstrates broad utility of ICAM-1-mediated targeting and transport for a variety of drug delivery systems and cell types. ICAM-1-targeted systems were tested, including biotin-streptavidin conjugates, polystyrene particles, PLGA carriers, poly-ethylene glycol poly-lactic acid (PEG-PLA) carriers, and natural polymer dendrimers, were efficiently internalized by cells in culture (FIG. 3A); and all tested endothelial cells, such as lung and brain endothelium, from macro- and micro-vascular beads, of mouse and human origin (FIG. 3B), and also by non-endothelial cells, including macrophages, alveolar epithelial cells, and neuroblastoma cells (FIG. 3C). Hence, altogether this series of experiments demonstrate the efficacy and versatility or ICAM-1 targeting in the context of delivery of drug carriers in cell cultures and in vivo, to different sub-cellular environments, in control and diseased conditions.

Figure 4:
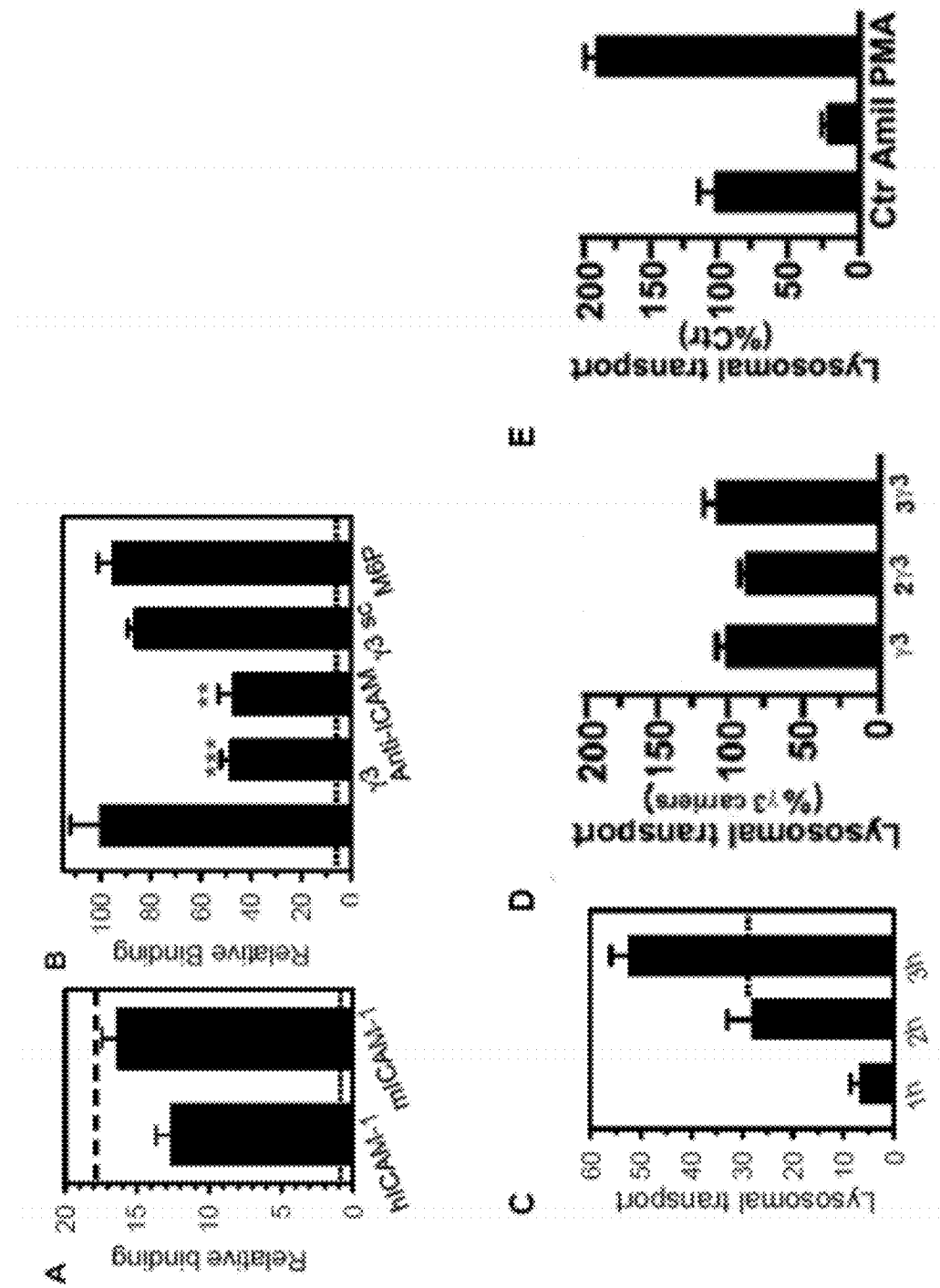
FIG. 4 illustrates the results of Example 4, where FIG. 4A provides a graph of the relative binding of γ3 carriers to both human and mouse ICAM-1, and as compared to anti-ICAM carriers.
Figure 5:
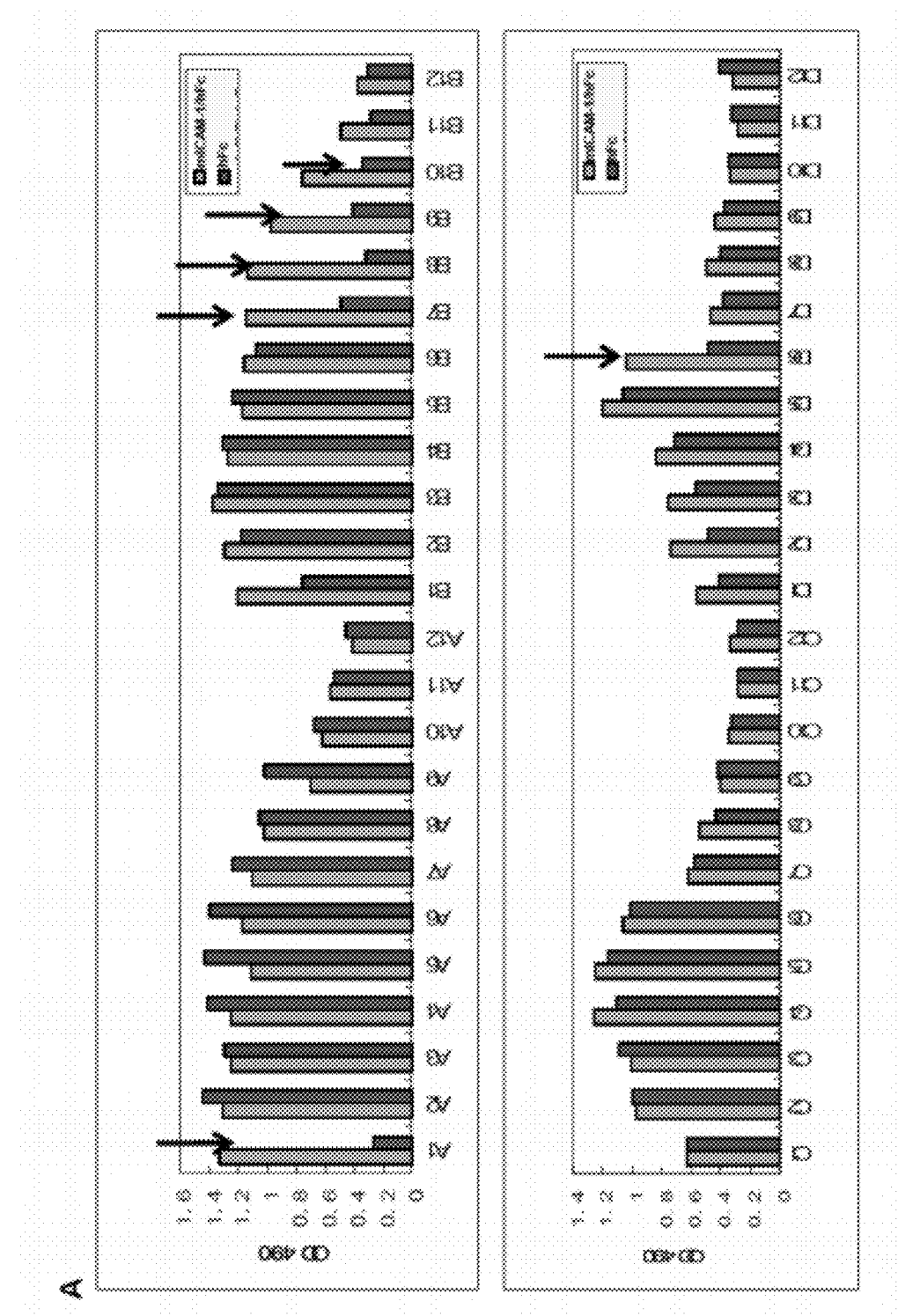
Figure 5:
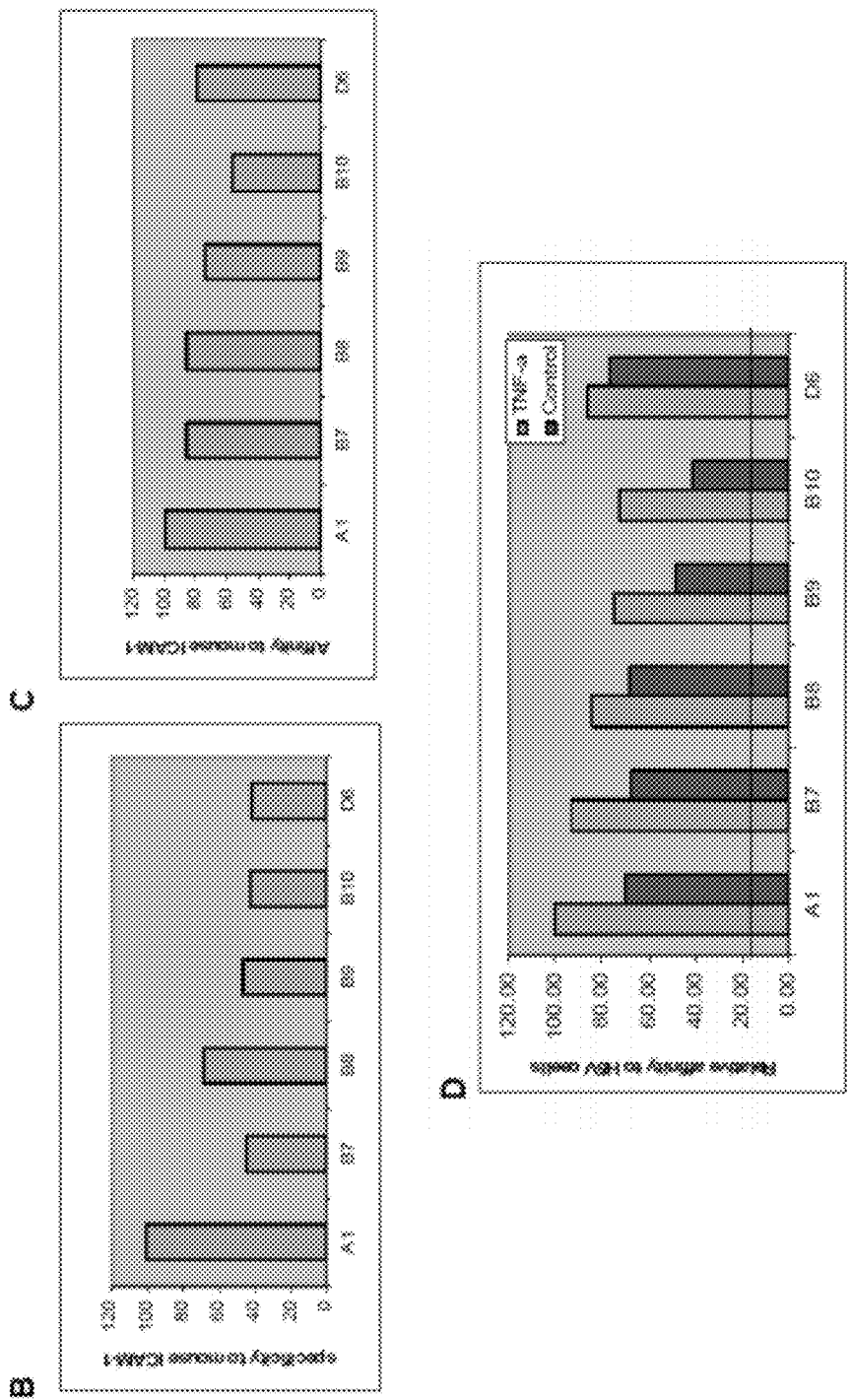
Figure 5:
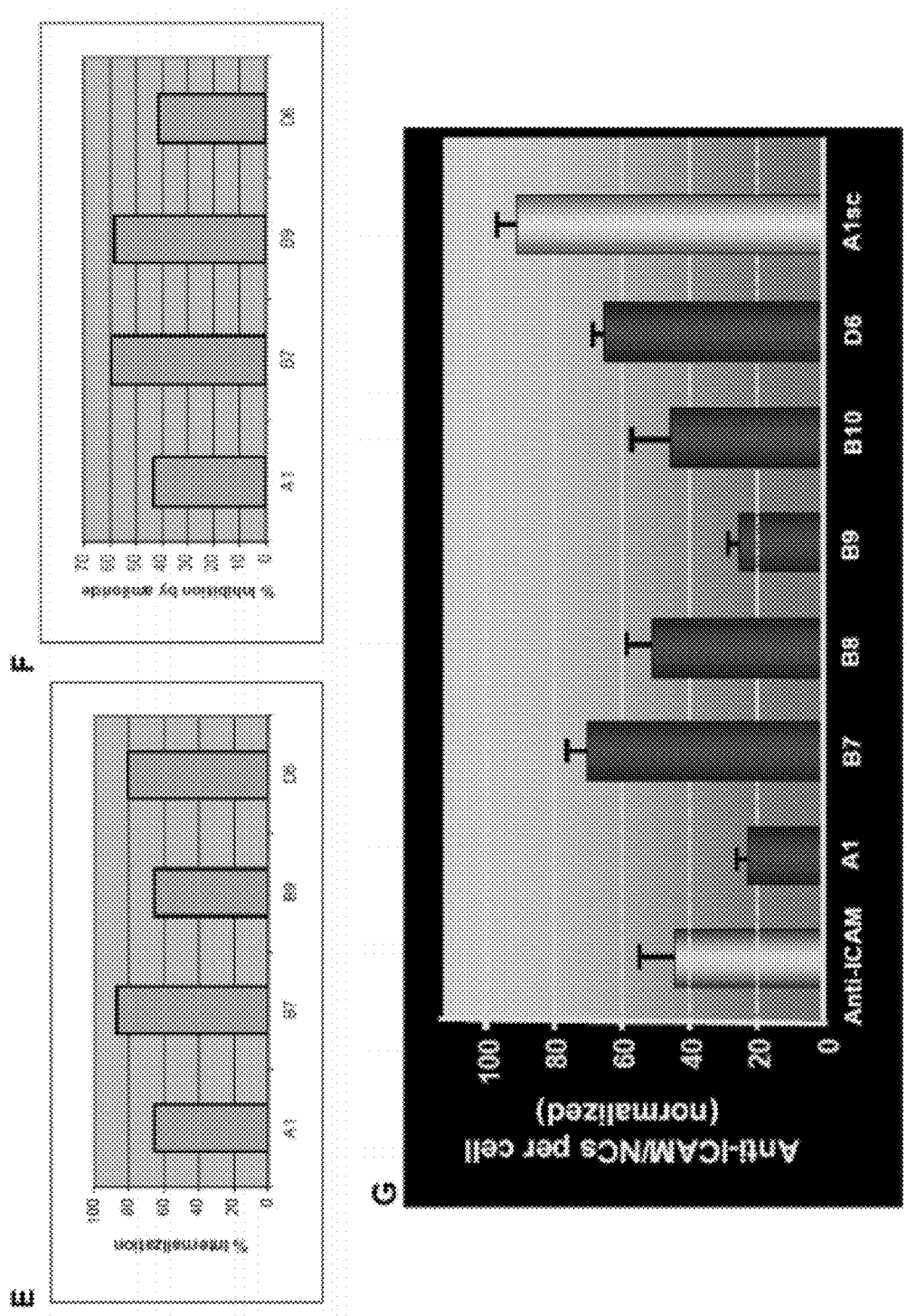
Figure 6:
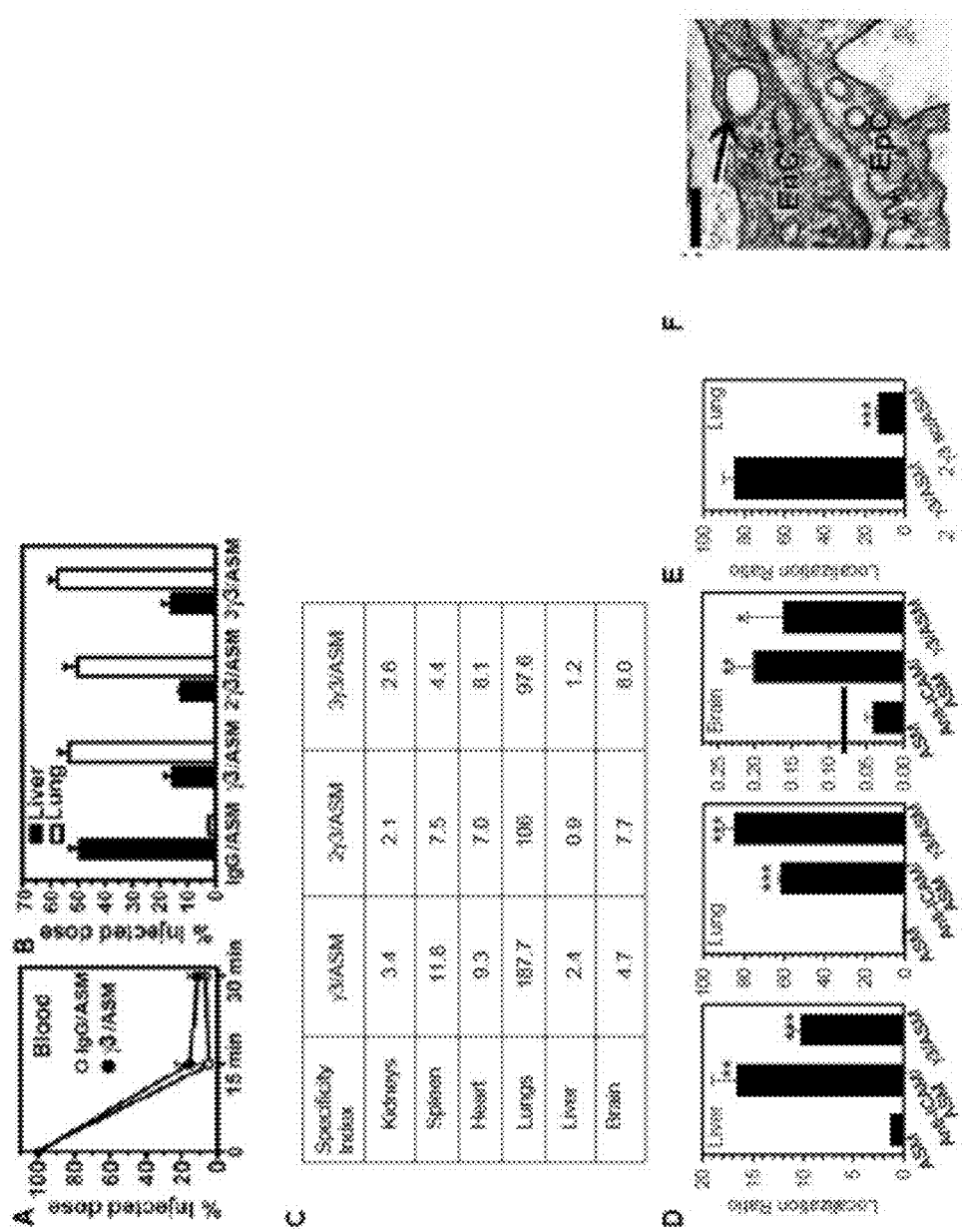

Example 4 demonstrates efficient and specific binding and intracellular transport of therapeutic carriers to human and mouse ICAM-1 via the affinity peptide γ3 and its derivative peptides 2γ3 and 3γ3. Furthermore, synthetic peptide γ3 was absorbed on 100 nm FITC polystyrene particles and the resulting carriers efficiently bound to immobilized human ICAM-1/Fc (as expected) but also, surprisingly, to mouse ICAM-1/Fc, vs to control immobilized albumin (FIG. 4A). Binding was similar to that of anti-ICAM carriers (FIG. 4A). Hence, γ3 can be used in mouse and human models and settings. The γ3 carriers also bound to native ICAM-1 expressed by both activated human and mouse endothelial cells, but not control 293 cells which are known to be voided of ICAM-1 expression (FIG. 4B). Importantly, co-absorption of the therapeutic enzyme ASM with γ3 on the carrier surface did not affect targeting to human or mouse endothelial cells (FIG. 4B). Targeting to these cells was similarly suppressed by excess of free γ3 peptide or anti-ICAM in the media, but not by a peptide with a scrambled γ3 sequence (FIG. 4B). Excess free mannose-6-phosphate (MP6) in the media did not compete for carrier binding to cells, either, indicating that M6P residues in ASM did not contribute to targeting (FIG. 4B).

The γ3/ASM polystyrene carriers were internalized by human and mouse endothelial cells at 37° C., and after uptake, γ3/ASM carriers trafficked to lysosomes in the perinuclear region of the cell, shown by co-localization with dextran-labeled lysosomes in HUVEC (FIG. 4C). Binding and internalization leading to lysosomal transport was similar for carriers targeted to ICAM-1 by either γ3 or their derivatives 2γ3 and 3γ3 (FIG. 4D). Endocytic transport was inhibited by amiloride and activated by phorbol esters activating protein kinase C or PKC, confirming a CAM-mediated mechanism (FIG. 4E). Hence, γ3 carriers elicit the same unique pathway than anti-ICAM carriers, crucial to effectively deliver therapeutics intracellularly and across cells.

Example 5 details development of the 7-mer phage-display derived peptides against ICAM-1. These were identified and isolated from a random library by using a chimeric ICAM-1 protein consisting of the two most membrane-distal Ig domains of mouse ICAM-1 fused to human Fc (hFc). One round of negative selection against hFc, followed by three rounds of positive selection against mouse ICAM-1/hFc, rendered six phage clones (A1, B7, B8, B9, B10, and D6), which recognized immobilized mouse ICAM-1 (FIG. 5A). Specificity vs hFc was higher for A1 (~5.1 fold), followed by B8>B7>B9>B10>D6 (68.6%-41.2% of A1) (FIG. 5B). A1 clone presented the highest affinity to immobilized mouse ICAM-1 (~4.7 fold over non-selected phages), followed by B7>B8>D6>B9>B10 clones (85.7%-56.7% of A1) (FIG. 5C). All six clones recognized native ICAM-1 expressed by mouse endothelial cells (H5V) as compared to control 293-ICAM-1 negative-cell type. In this setting, also A1 phage clone presented the highest affinity followed by D6>B10>B7>B8>B9 clones (92.9%-72.3% of A1) (FIG. 5D). Binding to cells increased up to 1.8 fold by TNFα, a cytokine which up-regulates ICAM-1 expression (FIG. 5D).

In addition, fluorescence microscopy showed that phage viruses expressing 5 copies of the peptides A1, B7, B9, or D6 (but not B8 or B10) on their capsid were internalized by endothelial cells at 37° C. (65-87% internalization, 1 h) but not at 4° C., indicative of endocytosis (FIG. 5E). This process was inhibited by amiloride (41-59% inhibition) (FIG. 5F), which has been shown in the past to interfere with CAM-mediated endocytosis. Therefore, these peptides are also adequate for either stable delivery to the cell surface, or intracellular delivery.

Surprisingly, clone A1 phages also strongly recognized immobilized human ICAM-1/hFc and native human ICAM-1 expressed by human endothelial cells (HUVEC), (~70% affinity of mouse ICAM-1). A1 peptide synthesized in vitro (but not control A1 scramble peptide), as well as B9 (and at some extent B8 and B9) competed binding of anti-ICAM nanocarriers to human endothelial cells (~80% inhibition) (FIG. 5G). This is a crucial finding, since it provides the opportunity to utilize these peptides in mouse and human cells and settings, and potentially in future clinical trials. Also, this demonstrates that ICAM-1-targeting peptides can block binding of other objects to ICAM-1, e.g., for applications such as beneficial blockage of binding of leukocytes, fibrinogen/fibrin, and/or pathogens to ICAM-1.

Example 6 demonstrates in vivo pharmacokinetics and biodistribution of therapeutic carriers targeted to ICAM-1 via the affinity peptide γ3 and its derivative peptides 2γ3 and 3γ3. In animal model tests, the γ3 2γ3 or 3γ3 carriers, coupled to therapeutic ASM, bound specifically and efficiently to, and were endocytosed by, endothelium in vivo in mice. They rapidly disappeared from the bloodstream (FIG. 6A), which was not a consequence of rapid clearance by the reticuloendothelial system (as in the case of clearance of control IgG/ASM carriers by the liver) but rather a consequence of rapid targeting to organs, e.g., the lungs, after i.v. injection in mice (FIG. 6B). Indeed, γ3 2γ3 or 3γ3 carriers enhanced the delivery of ASM vs than of free ASM in all organs, including brain, kidneys, spleen, liver, heart, and lungs, and 2γ3 or 3γ3 carriers showed lower lung deposition and greater brain deposition than γ3 carriers (specificity index, FIG. 6C) This is the first time that test brain targeting of ICAM-1 strategy has been examined and surprisingly its efficacy was found to be higher than the one reported for strategies of targeting to determinants commonly used for brain delivery, such as the case of insulin receptor or transferrin receptor: targeting to insulin receptor of α-L-iduronidase=0.02% injected dose per gram (% ID/g) versus ICAM-1 targeting of ASM prototype carriers=0.2% ID/g in brain.

Accumulation of ASM delivered by γ3, 2γ3 or 3γ3 carriers to this organs was comparable to that of ASM delivered by anti-ICAM carriers (FIG. 6D). This is readily clear from the localization ratio of these formulations, which represents the ratio between the % injected dose per gram of organ and that in circulation. Since the estimated dose measured in a given organ also include that of the blood irrigating that organ, the localization ratio permits to normalize data to the different levels of circulating materials. For instance, ASM lacks affinity and results in high circulating levels compared to ICAM-1 targeted formulations that rapidly bind to endothelium and disappear from blood. ASM targeting in vivo to ICAM-1 by the γ3-strategy was specific, as shown by lack of targeting of 2γ3-scramble/ASM carriers, or that of 2γ3/ASM carriers in ICAM-1 KO mice (FIG. 6E). Importantly, targeting to ICAM-1 with biodegradable PLGA carriers by the γ3-strategy resulted in CAM-mediated endocytic transport in vesicular compartments in endothelium in vivo (e.g., 2γ3/ASM PLGA carriers in FIG. 6F).

Example 7 demonstrates the therapeutic effects of cargoes intracellularly delivered to patient cells by γ3-strategy carriers (Table 1).

As an example of the therapeutic utility of this strategy, the effects of ASM targeting were compared to ICAM-1 using anti-ICAM vs the γ3-strategy provided herein. Recombinant ASM is used for enzyme replacement therapy of patients of types A and B Niemann-Pick disease, where genetic mutations lead to ASM deficiency and intracellular lysosomal accumulation of sphingomyelin and cholesterol, resulting in cell dysfunction, multi-organ complications, and often a fatal outcome. (He X., et al., *Anal. Biochem.* 2003; 314:116-20; Schuchman E. H., and Muro, S., *The development of enzyme replacement therapy for lysosomal diseases: Gaucher disease and beyond*. In: Futerman A H, ed. Gaucher disease: Lessons learned about therapy of lysosomal disorders: CRC Press; 2006:125-40.) It has been previously shown by the present inventors that anti-ICAM carriers deliver active ASM to lysosomes in cells from Niemann-Pick patients, attenuating sphingomyelin and cholesterol storage to control values, vs free ASM which only partially attenuates the levels of these lipids. Similar levels of degradation of these lipids were achieved by targeting ASM to ICAM-1 via the present γ3 strategy, using either prototype polystyrene carriers or biodegradable PLGA carriers (Table 1).

Example 8 provides a strategy for the design of a chimeric therapeutic enzyme containing ICAM-1-targeting γ3, 2γ3 or 3γ3 derivative peptides, or A1, B7, B8, B9, B10, or D1 peptides.

Figure 7:
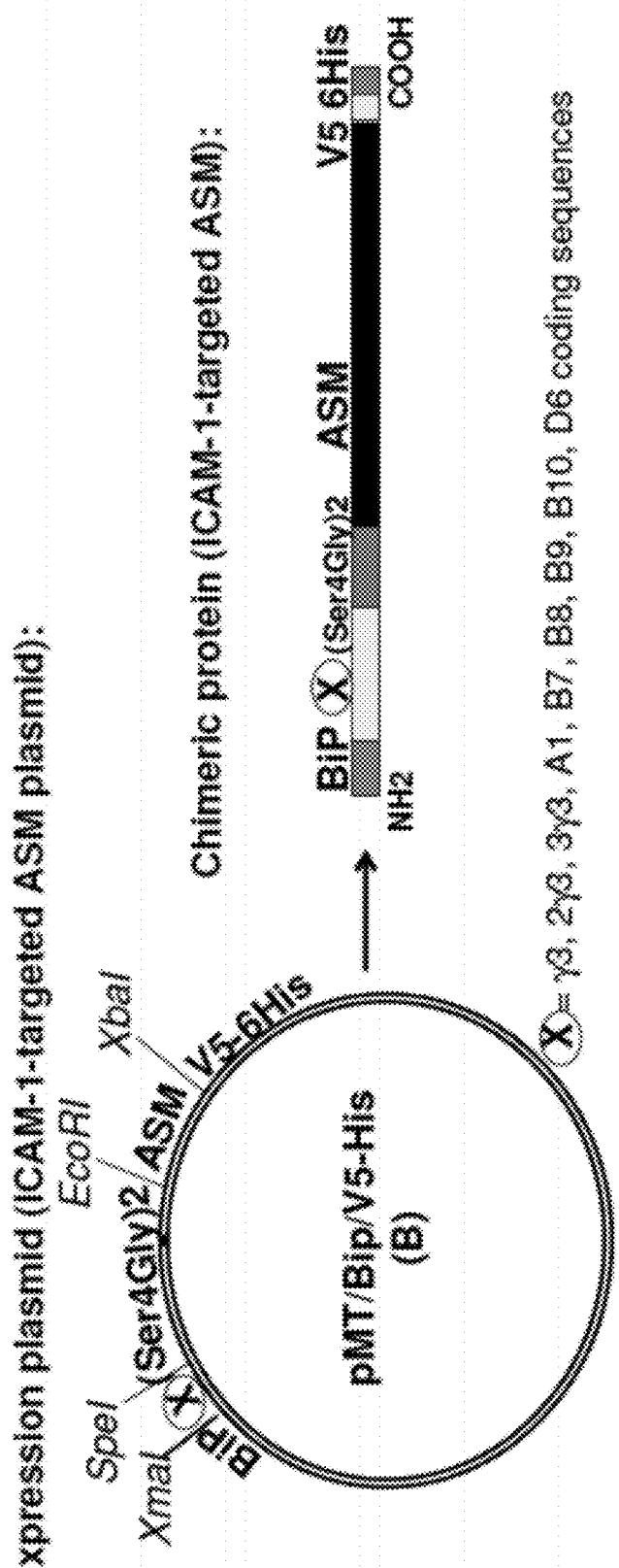

Further, direct coupling of γ3, 2γ3, 3γ3, A1, B7, B8, B9, B10, and/or D6 peptides (or their nucleotide encoding sequences) to therapeutic or diagnostic agents, via biotin-streptavidin, chemical conjugation, covalent coupling, through antibodies, or direct synthesis (e.g., chimeric proteins or their coding sequence for gene expression via plasmid, viral or non-viral vectors), is contemplated for utility for ICAM-1 targeting and transport to cells or the body in vivo. As an example, FIG. 7 shows the design of a therapeutic chimeric enzyme produced from a plasmid containing γ3, 2γ3 or 3γ3 sequences cloned at the amino-terminus of the ASM sequence, separated by a (Ser-4-Gly)$_2$ peptide spacer to allow independent folding and the targeting and enzymatic moieties of the chimera. This cassette can be cloned in a pMT/BiP/V5-His (B) plasmid for amplification under ampicillin selection in E. coli and expression in S2 insect eukaryotic cells, which will allow for expression under metallothionein promoter upon induction by copper sulfate, traffic of the chimeric enzyme through the secretory pathway due to presence of BiP, and extracellular secretion after BiP cleavage by S2 cells. The chimeric enzyme, which contains V5 sequence and 6H is tag fused to the carboxyl terminus, can be purified using a Ni-chelating resin. The resulting protein (~80 kDa) can be separated by SDS-PAGE and blotted with anti-V5 to trace the V5-tag. Possible modifications of this design include elimination of the BiP, V5 and/or His-tag sequences, elimination of change of the linker, cloning of the targeting peptide in the carboxyl-terminus of ASM, exchange of the ASM coding sequence for another therapeutic gene, siRNA, or cloning of the targeting peptide with no cargo, tandem repeats of the targeting peptide to allow for multivalency of ICAM-1 targeting, inclusion of interacting peptides or sequences to promote dimerization, tetramerization, or formation of oligomers of the peptides or the chimera, and to provide multivalent targeting to ICAM-1, cloning into other vectors for expression under different selection markers, in different cell types, in bacteria, by viruses, for enzyme or gene therapy, among other modifications.

Figure 9:
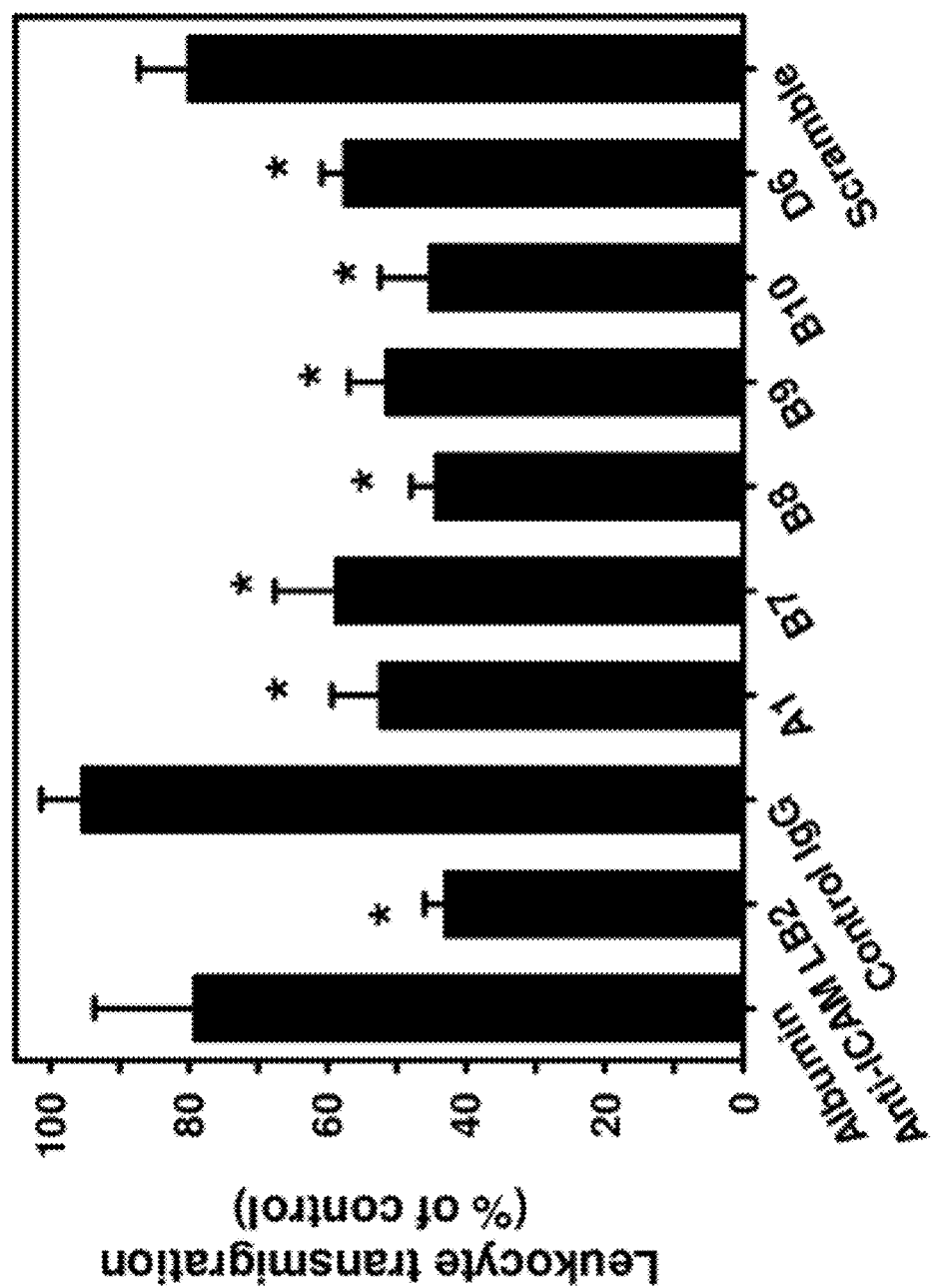

Example 9 provides in vivo brain transport of a composition of the invention in a mouse model, where the composition contains 2γ3/ASM and PLGA. FIG. 9 is transmission electron microscopy pictures showing successful migration of the compositions across the blood-brain barrier.

Example 10 provides inhibition of inflammatory leukocyte transmigration across endothelial cells by ICAM-1-targeting peptides A1, B7, B8, B9m B10 and D6. All were shown (FIG. 9) to inhibit leukocyte transmigration, when compared to the controls (albumin (negative control), scrambled peptide (negative control) and LB2 (positive control)).

Example 11 provides in vivo inhibition of lodging of fibrin microemboli in the vasculature of mice by administration of ICAM-1-targeting peptide γ3, resulting in continued circulation of the fibrin microemboli, rather than lodging in the vasculature or other organ.

Therefore, it is possible to safely and effectively target therapeutics and their carriers (including viruses) to both human and mouse ICAM-1, in a variety of cell types in culture and in vivo in animals and animal models, using the γ3 peptide, derivative peptides 2γ3 or 3γ3, and/or phage-derived peptides A1, B7, B8, B9, B10, or D6. This provides either stable binding to the cell surface and/or further transport to intracellular compartments and/or across cells for penetration in the tissues, with delivery of active compounds providing therapeutic benefits, as in the case of enzyme therapies and/or gene therapies for lysosomal disorders (see U.S. Provisional Patent Application 60/584,648). Exemplary carriers for safe transport of materials from intracellular compartments such as endosomes into the cell cytosol and nucleus are described in U.S. Provisional Patent Application 60/931,552. The present ICAM-1-targeting strategy in combination with these carriers have general applicability for delivery to these cell compartments.

ICAM-1 serves as an adhesive surface for leukocytes during inflammation (L. Yang, et al., *Blood* 106, 2 (2005): 584-92; S. Muro, VCAM-1 and ICAM-1. In: Aird W. (Ed), The Endothelium: A Comprehensive Reference. Cambridge Univ. Press. 2007: New York. 1058-1070; Rothlein R, et al., *J Immunol* 1986; 137:1270-4.). It is constitutively expressed on diverse cell types, including (but not restricted to) endothelial, Schwann, glial, and epithelial cells, leukocytes, myocytes, etc (S. Muro, VCAM-1 and ICAM-1. In: Aird W. (Ed), The Endothelium: A Comprehensive Reference. Cambridge Univ. Press. 2007: New York. 1058-1070; Hopkins, A. M., et al. *Adv Drug Deliv Rev* 56 (2004): 763-778.) Since ICAM-1 is expressed in diverse cell types in the body, including epithelial cells lining most of body cavities and entry routes (e.g., epithelial cells in the airways and alveoli, epithelial cells in the gastrointestinal tract, mesothelial cells in the pleura, and epithelial cells lining joints and ventricles in the CNS), muscle cell, glial and neuronal cells, etc., the compositions and methods described herein are useful for delivery of drugs to all of these compartments in the body. Furthermore, delivery is likely to be enhanced under pathological conditions due to overexpression of ICAM-1 and ICAM-1 blocking may be additionally beneficial (anti-inflammatory effects, anti-thrombotic by preventing deposition of fibrinogen and/or fibrin). Similar methods could be applied for intracellular delivery of drugs, biosensors, research, analytical, imaging, diagnostic and therapeutic agents, either in the context of research or clinical applications.

ICAM-1 is an attractive target to achieve selectivity toward disease sites in the body, since the expression of this molecule is up-regulated in many pathologies (S. Muro, VCAM-1 and ICAM-1. In: Aird W. (Ed), The Endothelium: A Comprehensive Reference. Cambridge Univ. Press. 2007: New York. 1058-1070; Rothlein R, et al., *J Immunol* 1986; 137:1270-4; Hopkins, A. M., et al. *Adv Drug Deliv Rev* 56 (2004): 763-778; Hubbard, A. K. & Rothlein, R. *Free Radic Biol Med.* 28 (2000): 1379-1386.). Targeting ICAM-1 does not seem to lead to side effects and indeed this strategy is being explored to block of ICAM-1 adhesive function and provide side benefits, such as anti-inflammatory effects (Takei, Y. et al., *Transplant Proc* 28 (1996): 1103-1105; Kavanaugh, A. F., et al., *Arthritis Rheum* 40 (1997): 849-853; Hallahan, D. E. & Virudachalam, S. *PNAS.* 94 (1997): 6432-6437.). For instance, antibodies to ICAM-1 are being explored as therapeutics and affinity carriers in cell cultures, animal models, and early clinical studies, where they have shown good safety (Muro, S. et al., *Mol. Ther.* 13, 1 (2006): 135-141; Garnacho, C. et. al. *JPET* 325 (2008): 400-408; Muro, S. et al., *Molecular Therapy* 16, 8 (2008): 1450-1458; Murciano, J. C., et al., *Blood* 101 (2003): 3977-3984; Villanueva, F. S., et al., *Circulation* 98 (1998): 1-5; Weller, G. E., et al., *Ann Biomed Eng.* 30 (2002): 1012-1019; Danilov, S. M. et al., *Am J Physiol* 280 (2001): L1335-L1347; Sakhalkar, H. S., et al., *Proc Natl Acad Sci USA* 100 (2003): 15895-15900; Rossin, R., et al., *J. Nucl. Med.* 49, 1 (2008): 103-111; Muro, S., et al., *Blood.* 105 (2005): 650-658.). The short peptides and peptides identified by phage-display described herein also serve as ICAM-1 targeting molecules to provide efficient and specific binding of therapeutic agents and drug delivery systems to ICAM-1 in both mice and humans.

Coupling of multiple ICAM-1-targeting moieties (e.g., anti-ICAM antibodies) on the surface of carriers has been shown to provide binding of carriers to ICAM-1 expressed on the plasma membrane of cells (Muro, S., et al., *Am J Phys-Cell Physiology.* 285, 5 (2003): C1339-47.). Carrier binding through multiple ICAM-1-targeting molecules (multivalent binding) causes ICAM-1 to cluster, which initiates signal transduction pathways leading to uptake of such carriers into cells by an endocytic mechanism known to as Cell Adhesion Molecule- or CAM-mediated endocytosis, which is distinct from classical mechanisms of macropinocytosis, phagocytosis, clathrin- or caveolar-mediated endocytosis described above (Muro, S., et al., *Am J Phys-Cell Physiology.* 285, 5 (2003): C1339-47.). However, when presented to cells as non-coupled counterparts (in contrast to multivalent binding) binding of the ICAM-1-targeting moieties (e.g., anti-ICAM) to ICAM-1 on endothelial cells does not elicit this endocytic transport mechanism. This precludes the use of ICAM-1-targeting molecules per se (without a carrier scaffold or another mechanism to provide multivalent binding to ICAM-1) from being used for drug delivery into or across cells.

In addition, CAM-mediated endocytosis has only been demonstrated in endothelial cells that constitute the inner layer of the blood vessel but not in epithelial cells from GI tract. Endothelial cells are believed to have a very active endocytic capacity given that they use this mechanism of transport to control exchange of large macromolecules and blood cells between the blood and the tissues, whereas GI epithelial cells transport most substances via cell junctions, non-endocytic channels and carrier proteins in their membrane, which are not suitable for safe transport of large bulky drug carriers (Owen, R. L. *Semin. Immunol.* 11 (1999): 157-163; Hidalgo, I. J. & Borchardt, R. T., *Biochim. Biophys. Acta* 1028 (1990): 25-30; Muro, S., et al. *Curr. Vasc. Pharm.* 2 (2004): 281-299; Predescu, D., et al., *Am. J. Physiol. Lung Cell Mol. Physiol.* 287 (2004): L895-L901.). It was therefore uncertain whether the signal cascades and other cell machinery related to CAM-mediated endocytosis is in place in GI epithelial cells and whether such mechanisms could be employed in transport of carriers across the epithelial tract.

Furthermore, polarized epithelial cells of the GI tract, with multiple protruding microvilli in the apical membrane in contact with the GI lumen, have a morphology categorically different from the flat easily accessible apical surface of endothelial cells in blood vessels, which can pose a tremendous accessibility obstacle to ICAM-1-targeting moieties and/or carriers. Moreover, endothelial cells are believed to express the highest level of ICAM-1, which may contribute to induction of CAM-mediated endocytosis, whereas ICAM-1 levels in other cells are only relevant or have increased relevance by up-regulation during pathological stimuli but are not relevant or have decreased relevance under normal conditions, which is likely to be the case for delivery of drugs needed in distal diseased areas across a healthy GI tract (Muro, S., et al. *Curr. Vasc. Pharm.* 2 (2004): 281-299; Rothlein R, et al., *J Immunol* 1986; 137:1270-4.). Finally, all characterized ICAM-targeted delivery systems underwent intracellular trafficking via endosomal vesicles to either plasma membrane recycling pathways (in rare instances) or (in most instances) to lysosomal delivery and degradation (Muro, S., et al., *J Cell Sci,* 116, 8 (2003): 1599-1609; Muro, S. & Muzykantov, V. R., *Curr Pharm Des.* 11 (2005): 2383-2401; Muro, S. et al., *Mol. Ther.* 13, 1 (2006): 135-141.) but not to cross epithelial layers by transcytosis. In fact, ICAM-1 serves as an adhesion surface for leukocytes during inflammation and is involved in the process of leukocyte migration into tissues by opening of cell junctions linked to the paracellular transport (Muro, S., et al. *Curr. Vasc. Pharm.* 2 (2004): 281-299; Rothlein R, et al., *J Immunol* 1986; 137: 1270-4; L. Yang, et al., *Blood* 106, 2 (2005): 584-92.), which is opposite to safe transport by the transcellular route.

In consideration of these known characteristics of ICAM and GI epithelial cells, the possibility of ICAM-1 targeting to and transport across healthy GI epithelial cells by a transcellular mechanism was unlikely, uncertain and unpredictable. As set forth in the examples below, the present inventors have demonstrated methods of transport and delivery employing CAM-mediated endocytosis in the GI epithelial tract.

The examples provided herein demonstrate that GI epithelial cells support: (i) efficient and specific targeting of ICAM-1-targeted carriers both as non-activated healthy cells and also as pathologically altered cells, as well as (ii) safe, fast, and efficient transport of such carriers across their cellular body in both healthy and pathological conditions, via CAM-mediated endocytosis with no damaging opening of cell junctions. GI epithelial cells also supported targeting and CAM-mediated endocytosis of non-multivalent, non-coupled ICAM-1-targeting moieties (anti-ICAM) in the absence of carrier particles.

In the examples it was shown that GI epithelial cells express ICAM-1 and that anti-ICAM carriers bind to such GI epithelial cells efficiently and that uptake of the anti-ICAM carriers by GI epithelial cells is CAM-mediated endocytosis (Examples 12-15). A model representative of the GI epithelium was generated (Example 16) and tested for ICAM-1 expression (Example 17) and rapid anti-ICAM carrier transport (Examples 18 and 19). It was further shown that CAM-mediated endocytosis is involved in the transcytosis of anti-ICAM carriers in the model (Example 20), even in the case of non-multivalent binding to ICAM-1 (Example 21).

The examples therefore demonstrate that: (i) ICAM-1-targeted carriers bind efficiently to GI epithelial cells, such binding is specific to ICAM-1, and binding is relatively fast; (ii) ICAM-1-targeted carriers are transported across GI epithelial cells in a relatively efficient and fast manner; and (iii) transport of ICAM-1-targeted carriers does not occur via the paracellular pathway that disturbs the epithelial permeability barrier, but rather it occurs by an endocytic vesicular pathway related to CAM-mediated endocytosis.

The present invention therefore further provides specific strategies for effective targeting of GI epithelial cells, providing fast, safe and effective transport across the epithelial layer with no effect on the GI permeability and which provides increased bioavailability of the agent. In a particular embodiment, ICAM-1, expressed on the surface of GI epithelial cells is targeted.

In a preferred embodiment, the administration of the composition for delivery across the GI epithelium is provided to the subject orally. However, administration may be carried out in any manner sufficient to provide the composition to the digestive tract and/or in contact with the gastrointestinal epithelium.

Therefore in one embodiment the invention provides a composition comprising a targeting moiety comprising an anti-ICAM antibody; and an agent, wherein the targeting moiety recognizes and binds to ICAM-1 on a GI epithelial cell and the composition is transported across the GI epithelium. In a particular embodiment the composition is orally administered to a subject.

As previously noted herein, compositions of the invention may further comprise a delivery carrier. In one embodiment the delivery carrier is effective to transport the targeting moiety and the agent of the composition to the GI epithelial cell for uptake and/or transport.

Figure 21:
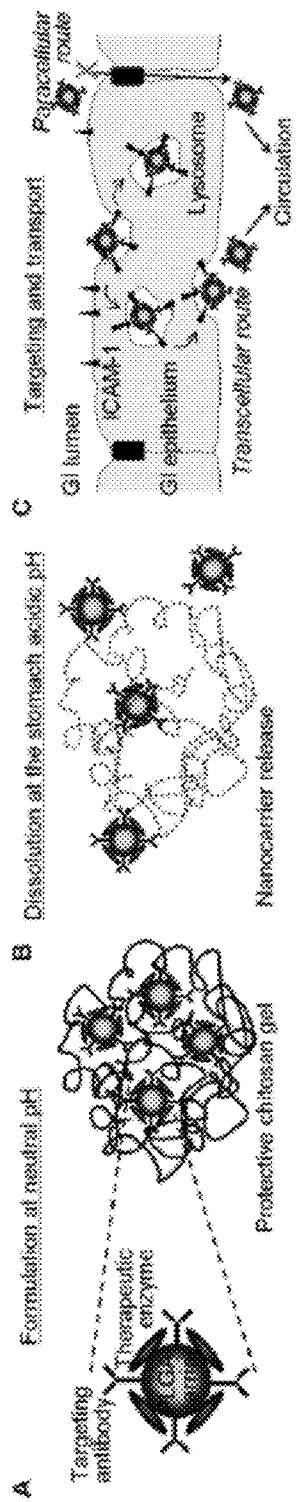

Compositions of the invention may further comprise a protective agent. In a particular embodiment the protective agent is effective to protect the targeting moiety and the agent from degradation prior to binding ICAM-1. Polymers and materials can be used to provide protection to ICAM-1-targeted carriers against potential degradation in the stomach while in transit to the intestine (Jung, T., et al., *Euro. Journ. Pharm. and Biopharm.* 50 (2000): 147-160), such as, but not limited to, polymers containing amino groups providing an acidic pKa, so that the polymer is insoluble at neutral pH and can be formulated as a tablet-like matrix or hydrogel containing carriers embedded in its structure, to protect them from rapid degradation in the GI. As such polymers pass through the acid pH in the stomach, their amines can become protonated and positively charged, allowing the polymer to transition to a soluble state. Gradual protonation of the polymer would favor bioadhesion to the negatively charged epithelial mucosa, and gradual dissolution would release ICAM-1-targeted carriers in situ, which will induce ICAM-1-mediated endocytic transepithelial transport with carrier release into the circulation. FIGS. 21A and 21B illustrate such exemplary use of a protective agent, where FIG. 21A illustrates protection of anti-ICAM carriers from degradation in the stomach by polymers (e.g., chitosan), FIG. 21B illustrates dissolution of polymer gels and gradual carrier release after passage through the stomach, and FIG. 21C illustrates binding and endocytic transcellular transport (vs paracellular transport) of carriers across the GI epithelial layer. A fraction of the carriers may also be delivered to lysosomes, where carriers may also release therapeutics, e.g., in the case of treatment of lysosomal storage disorders using recombinant enzymes, such as the case of deficiency of acid sphingomyelinase (ASM) in Niemann-Pick disease.

Figure 22:
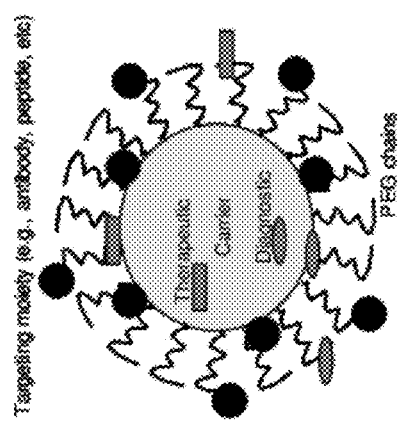

Protection of the targeting moiety and the agent may further comprise protection from the immune system of the subject. One limitation of GI drug delivery which could impede transport is the mucosa-associated lymphoid tissue (MALT), which contains various immune cells and may destroy some carriers, and M cells that sample antigens from the GI lumen, which are then delivered to the underlying MALT. In order to evade detection by immune cells of the gut, as shown in FIG. 22, carriers can be coated with certain polymers, including, but not limited to, polyethylene glycol (PEG), which acts by masking antigens (Moghimi et al., 2003) (e.g. anti-ICAM or ICAM-1-targeting peptides). To still achieve targeting, ICAM-1-targeting moieties can be attached to carriers via the PEG spacer arm, so that the targeting moiety is extended outside of the dense PEG brush for binding to ICAM-1. Substitution of anti-ICAM by small ICAM-1 targeting peptides as described herein may also provide an avenue for optimization of this strategy. Therapeutic and/or diagnostic agents can be carried within the interior of the carrier, on its surface, or coupled to PEG chains (not limited to the described locations).

Additionally, since ICAM-1 is also expressed in endothelial and other cell types it is likely that upon transport of ICAM-1-targeted carriers and their cargoes across GI epithelial cells and into the circulation, the compositions will subsequently target the endothelium and tissues that express ICAM-1. Because ICAM-1 expression is up-regulated under pathological conditions, upon transport into the circulation, such strategy will provide preferential targeting and delivery to disease-affected areas.

In addition, given that pathologically altered GI epithelial cells (e.g., human epithelial colorectal adenocarcinoma cells, TNFα treated cells which are a model of GI inflammation, etc), it is likely that this strategy may be also used to treat pathologies pertinent to the gut, such as colorectal carcinoma, inflammatory bowel disease, Crohn's disease, and ulcerative colitis, and bacterial infections (Dippold, W., et al., *Gut.* 34 (1993): 1593-1597; Kelly, C. P., et al. *Am J Physiol Gastrointest Liver Physiol* 263 (1992): G864-G870; Huang, G., et al., *J. Clinical Investigation.* 98 (1996): 572-583). The ability to effectively access these intestinal maladies promotes the possibilities that exist for clinical applications involving ICAM-1 targeting.

In a further embodiment, compositions of the invention may comprise a second or additional targeting moiety. Such targeting moiety may be effective to target a cell, tissue or organ after transport across the gastrointestinal epithelium and into the circulatory system, such that the second targeting moiety recognizes and binds to a target on the cell, tissue or organ, and is effective to deliver the agent to the cell, tissue or organ.

In a still further embodiment, the invention provides methods of using the compositions described herein. In one embodiment the invention provides a method for delivery of an agent across the gastrointestinal epithelium, comprising administration of a composition comprising a targeting moiety selected from SEQ ID NO:1, SEQ ID NO:2, SEQ ID NO:3, SEQ ID NO:14, SEQ ID NO:15, SEQ ID NO:16, SEQ ID NO:17, SEQ ID NO:18, SEQ ID NO:19, and an anti-ICAM antibody; and an agent, wherein the targeting moiety recognizes and binds to a target on a gastrointestinal epithelial cell and the composition is transported across the gastrointestinal epithelium. In a particular embodiment the composition is orally administered to a subject. In a further embodiment the target is a cell adhesion molecule (CAM) expressed on the surface of the gastrointestinal epithelial cell, e.g., ICAM-1.

As described herein, the preferred uptake and transport of the composition across the epithelium is a transcellular route. Such a route is advantageous in that it does not cause disruption of the permeability barrier. The compositions and methods of the invention provide such transport.

The compositions and methods of the invention therefore demonstrate significant therapeutic benefits of ICAM-1-targeted carriers in GI and oral drug delivery.

The advantages and features of the invention are further illustrated with reference to the following examples, which are not to be construed as in any way limiting the scope of the invention, but rather as illustrative of various embodiments of the invention in specific applications thereof.

EXAMPLE 1

Efficacy and Versatility of Targeting to and Transport Mediated by ICAM-1 Vs Determinants of Classical Endocytic Pathways (A) Lung uptake (30 min) of $^{125}$I-labeled anti-transferrin receptor (targeted to the clathrin route), anti-GM1 (anti-ganglioside GM1, targeted to caveoli), or anti-ICAM, injected intravenously in mice as free antibodies or absorbed on the surface of 100 nm polystyrene particles (prototype carrier final size=180 nm). Particles had $^{125}$I-labeled IgG as a tracer. Dashed line=control unspecific IgG carriers. (B) Lung uptake (30 min) of radiolabeled acid sphingomyelinase, a recombinant enzyme which binds to mannose 6 phosphate (M6P) receptor, vs anti-ICAM polystyrene carriers in control C57Bl/6 mice vs diseased ASMKO mice. Data is normalized per gram due to larger lung size in ASMKO mice. Dashed line=anti-ICAM carriers injected in control ICAM-1 KO mice, which do not express ICAM-1. (C) Endocytosis (1 h-37° C.) of fluorescent transferrin (targeted to the clathrin route), cholera toxin B (targeted to the caveolar route), EGF-induced dextran (macropinocytosis), and 180 nm anti-ICAM polystyrene carriers (CAM-endocytosis) by fibroblasts from patients of type A-B Niemann-Pick, or 1 µm IgG-coated particles (phagocytosis) by diseased ASMKO alveolar macrophages, analyzed by fluorescence microscopy. (D) Internalization (1 h-37° C.) of fluid-phase Texas-red dextran by skin fibroblast from Fabry, Gaucher, type C Niemann-Pick (NPC) and NPD patients, characterized by deficiency of α-galactosidase-A, glucocerebrosidase, NPC1 transporter, and ASM, respectively. (E) FITC-labeled anti-ICAM carriers of diverse geometry (anti-ICAM polystyrene spheres from 0.1 to 5 µm or 0.1×1×3 µm elliptical disks, and polymorphous anti-ICAM conjugates formed by biotin-streptavidin crosslinking were incubated with TNFα activated human umbilical vein endothelial cells (HUVEC) for 1 h at 37° C. The cells were then washed and fixed, cell surface-located carriers were differentially stained with a texas red-conjugated secondary antibody, and the samples were analyzed by fluorescence microscopy to quantify the percent of carriers internalized by the cells. Data are mean±standard error of the mean for n≥4 mice or ≥20 cells. *$p<0.05$, $p<0.005$, *$p<0.001$ by student's t test.

EXAMPLE 2

Transport to Different Sub-Cellular Environments Via ICAM-1 Targeting (A) TNFα activated HUVEC were incubated for 1 h at 37° C. with anti-ICAM antibody, then non-bound antibodies were washed and cells were stained with a secondary antibody conjugates to texas red, only accessible to cell surface-located anti-ICAM, to detect the antibody fraction that remained in the plasma membrane. Then, cells were permeabilized and stained with a secondary antibody conjugated with green FITC, which would be accessible to both surface and internalized anti-ICAM. After analysis by fluorescence microscopy, cell surface antibodies were visualized both under the green and red channels, indicated by yellowish fluorescence, whereas no green internalized antibodies were observed. (B) HUVEC were incubated for 1 h at 37° C. with anti-ICAM antibodies absorbed on the surface of 100 nm FITC-labeled polystyrene nanocarriers. Cells were then washed, fixed, and stained with texas red secondary antibody which can only detect accessible surface anti-ICAM carriers. After analysis by fluorescence microscopy, internalized carriers were visualized under the green channel in the perinuclear region of the cell, whereas no yellowish carriers on the cell surface were observed. Dashed lines in (A) and (B) mark the cell border, determined by phase-contrast microscopy. (C) Anti-ICAM/ASM polystyrene carriers were injected in anesthetized C57Bl/6 mice. Five hours after injection, the animals were perfused and fixed through the left ventricle under ventilation, and the lungs were isolated and processed for transmission electron microscopy. Arrows=endothelial cell (EC) surface-bound carriers. White arrowhead=carriers in an intracellular endosome. Black arrowheads=carriers in intracellular lysosomes. Grey arrowhead=intact cell junctions. Asterisks=caveoli. Bordered arrowheads=carriers transported across the endothelial layer into epithelial cells in the alveoli. Scale bar=100 nm. (D) Activated HUVEC were incubated for 30 min at 4° C. with FITC-labeled anti-ICAM polystyrene carriers (spherical 180 nm or 1 µm, or discoidal 0.1×1×3 µm) to only allow binding, following by washing and endocytosis of pre-bound particles for 1 h (not shown) or 5 h at 37° C. The cells were then fixed and the presence of particles containing intact anti-ICAM coat on the cell surface was assessed by immunostaining using a Texas-red secondary antibody. Since after 1 h incubation no red+green (yellow) particles were visualized in the cell surface, the appearance of such particles at later times indicate recycling from intracellular compartments, quantified by fluorescence microcopy. *$p<0.05$, by student's t test.

EXAMPLE 3

Broad Utility of ICAM-1-Mediated Targeting and Transport for a Variety of Drug Delivery Systems and Cell Types (A) TNFα activated HUVEC were incubated for 1 h at 37° C. with anti-ICAM conjugates prepared by coupling via streptavidin biotinylated anti-ICAM, anti-ICAM polystyrene nanocarriers, anti-ICAM poly-lactic co-glycolic acid (PLGA) nanocarriers, anti-ICAM poly-ethylen glycol (PEG) poly-lactic acid (PLA) nanocarriers, or biopolymeric dendrimers. Non-bound conjugates and carriers were washed, the cells were fixed, stained and analyzed as described in FIG. 2 A-B. (B) Internalization of 100 nm FITC-labeled (green) anti-ICAM polystyrene carriers by TNFα-activated macrovascular human umbilical vein endothelial cells (HUVEC), mouse pulmonary microvascular endothelial cells (PMVEC), human brain microvascular endothelial cells (BMVEC), and (C) mouse peritoneal macrophages, human alveolar epithelium-derived EAhy926, and human neuroblastoma SH-SY5Y. In all pictures cell surface-bound materials are shown in red+green double labeled color (yellowish) vs internalized materials which appear as single labeled in the green channel. Dashed lines mark the cell border, determined by phase-contrast microscopy. Magnification bar=10 µm.

EXAMPLE 4

Efficient and Specific Binding and Intracellular Transport of Therapeutic Carriers to Human and Mouse ICAM-1 Via the Affinity Peptide γ3 and its Derivative Peptides 2γ3 and 3γ3

(A) The peptide γ3 was absorbed on the surface of 100 nm FITC-labeled polystyrene carriers and the resulting products were incubated for 15 min on nitrocellulose-immobilized albumin vs human or mouse ICAM-1 chimeras containing ICAM-1-Ig domains 1 and 2 fused to human Fc sequence. The membranes were washed and analyzed by fluorescence microscopy to quantify the number of carriers bound per area. Data are expressed relative to non-specific binding of γ3 carriers to albumin controls (dotted line). A comparison to binding of anti-ICAM carriers is provided (dashed line). (B) Binding of FITC-labeled polystyrene carriers coated by absorption with the peptide γ3 and recombinant acid sphingomyelinase (ASM, a therapeutic enzyme) to activated HUVEC (bars) vs ICAM-1-negative 293 cells (dotted line) was quantified by fluorescence microscopy after 1 h incubation at 37° C., in the absence or presence of excess γ3, anti-ICAM, γ3 scramble peptide, or mannose 6 phosphate (M6P). Data is shown relative to HUVEC binding of γ3/ASM carriers (134±11 particles/cell). (C) HUVEC lysosomes were labeled for 2 h with Texas-red dextran at 37° C. Cells were then incubated for 30 min at 37° C. with FITC-labeled γ3/ASM carriers, non-bound carriers were washed, and incubation was continued up to 1, 2, or 3 h. Co-localization of FITC carriers with Texas-red dextran-lysosomes was quantified by fluorescence microscopy. (D) Comparison of lysosomal transport of 100 nm FITC-labeled polystyrene carriers coated with either ICAM-1-targeting peptide γ3 vs its derivatives 2γ3 and 3γ3. (E) Activated HUVEC were incubated for 30 min at 37° C. in the presence of FITC-labeled 2γ3 polystyrene carriers after 15 min pre-treatment with 3 mM amiloride to block ICAM-1-mediated endocytosis, or 0.1 µM PMA to activate PKC and promote ICAM-1-mediated endocytosis. Co-localization of FITC 2γ3 carriers with Texas red dextran-labeled lysosomes was assessed by microscopy 3 h post-internalization. Mean±SEM; n=2 assays. p<0.005, *p<0.001, by student's t test.

EXAMPLE 5

Efficient and Specific Binding and/or Intracellular Transport of Peptides or Peptide-Expressing Viruses to Human and Mouse ICAM-1 Via the Affinity Peptides A1, B7, B8, B9, B10, AND D6

(A) ELISA measurement of the binding of 7-mer peptide expressing phage library to immobilized recombinant ICAM-1 (consisting of the two most membrane-distal Ig domains -1 and 2- of mouse ICAM-1 fused to human Fc or hFc), versus their binding to control hFc. (B) Relative specificity and (C) relative affinity of ICAM-1-targeting peptide phages, determined by ELISA from the experiment in (A). (D) Relative binding of phages expressing 7-mer peptides to native ICAM-1 expressed on the surface of HV5 mouse endothelial cells, either control or activated with TNFalpha to mimic a disease phenotype. Binding was determined by microscopy using a fluorescently-labeled antibody to the phage capsid. The line in the graph indicates the level of binding of A1 phage to 293 cells, which are voided of ICAM-1-expression. (E, F) Endocytosis (1 h, 37° C.) of phages expressing 7-mer peptides by control mouse endothelial cells (E) or mouse endothelial cells incubated in the presence of 3 mM amiloride (F) was estimated by microscopy after staining surface-located phages with a Texas red-labeled antibody to the viral capsid, following by cell permeabilization and staining of all (surface and internalized) phages using a FITC-labeled antibody to the viral capsid. (G) Binding of FITC-labeled anti-ICAM polystyrene nanocarriers to human endothelial cells was evaluated by fluorescence microscopy after incubation with cells in the absence (100% level) or presence of anti-ICAM antibody, ICAM-1-targeting synthetic peptides, or peptides with their scramble sequence (e.g., A1 sc).

EXAMPLE 6

In Vivo Pharmacokinetics and Biodistribution of Therapeutic Carriers Targeted to ICAM-1 Via the Affinity Peptide γ3 and its Derivative Peptides 2γ3 AND 3γ3

IgG/$^{125}$I-ASM polystyrene carriers vs γ3/$^{125}$I-ASM carriers, 2γ3/$^{125}$I-ASM carriers or 3γ3/$^{125}$I-ASM carriers were injected iv in C57Bl/6 mice. Blood samples were taken at 15 min and 30 min after injection, and the organs were collected 30 min after injection, to determine the presence of $^{125}$Iodine in the samples. (A) Percent of injected dose in circulation is shown for control IgG/$^{125}$I-ASM polystyrene carriers vs γ3/$^{125}$I-ASM carriers. (B) Percent of injected dose in liver (an organ of unspecific clearance) and lung (and organ requiring targeting for accumulation) are shown. (C) Mice were injected with either free $^{125}$I-ASM vs γ3/$^{125}$I-ASM carriers, 2γ3/$^{125}$I ASM carriers or 3γ3/$^{125}$I-ASM carriers, blood and organs were collected 30 min after injection and the specificity index of all samples was calculated. Specificity index=Localization Ratio of the carrier divided by the Localization Ratio of the free enzyme, where the Localization Ratio is the percent injected dose/gram in an organ divided by percent injected dose/gram in blood. (D) Liver, lung, and brain uptake (30 min) of γ3/$^{125}$I-ASM polystyrene carriers compared to anti-ICAM/$^{125}$I-ASM carriers and control $^{125}$I-ASM. (E) Lung targeting of 273/$^{125}$I-ASM polystyrene carriers vs 2γ3-scramble/$^{125}$I-ASM carriers in control C57Bl/6 mice (bars), and 273/$^{125}$I-ASM carriers in ICAM-1 knock out (ICAM-1 KO) mice (line across the bar on the left). Mean±SEM; n=3 mice. (F) Transmission electron microscopy picture showing endocytosis of 2γ3/ASM PLGA carriers in lungs of mice (30 min post-injection). Asterisks=caveoli. EnC=Endothelial cell. EpC=Epithelial cell. Scale bar=100 nm.

EXAMPLE 7

Therapeutic Effects of Cargoes Intracellularly Delivered to Patient Cells by γ3-Strategy Carriers Skin fibroblasts from type A Niemann-Pick patients were incubated overnight with BODIPY-FLC12-sphingomyelin to label sphingomyelin accumulation in lysosomes in these cells. Cells were then incubated with control media or treated for 5 h with recombinant ASM loaded on the surface of 100 nm polystyrene carriers or poly-lactic co-glycolic acid (PLGA) carriers targeted to ICAM-1 via either anti-ICAM monoclonal antibody or the peptide γ3. The cells were then washed, fixed, and stained with filipin to label cholesterol, which also accumulates intracellularly in Niemann-Pick disease. Samples were analyzed by fluorescence microscopy to determined the reduction of the levels of sphingomyelin and cholesterol. The percent of accumulation of these lipids was compared to that of untreated diseased cells (100% accumulation). Mean±SEM, n>20 cells.

TABLE 1

| (% no treatment) | Anti-ICAM/ ASM polystyrene | γ3/ASM polystyrene | γ3/ASM PLGA |
|---|---|---|---|
| Sphingomyelin | 10 ± 1.7 | 10 ± 1.9 | 3 ± 1.3 |
| Cholesterol | 6 ± 1.0 | 5 ± 1.1 | 5 ± 0.7 |

EXAMPLE 8

Design of a Chimeric Therapeutic Enzyme Containing ICAM-1-Targeting γ3, 2γ3 3γ30R A1 Derivative Peptides The coding sequence for the peptides γ3, 2γ3, 3γ3 or A1 can be formed by hybridization of the forward (F) and reverse (R) oligonucleotides XmaI-ATG-γ3-SpeI, XmaI-ATG-2γ3-SpeI, XmaI-ATG-3γ3-SpeI, XmaI-ATG-B7-SpeI, XmaI-ATG-B8-SpeI, XmaI-ATG-B9-SpeI, XmaI-ATG-B10-SpeI, or XmaI-ATG-D6-SpeI, respectively. The coding sequence for spacer between these peptides and ASM can be formed by hybridization of the forward (F) and reverse (R) oligonucleotides SpeI-(Ser4Gly)-2-EcoRI. ASM coding sequence can be amplified by PCR from a plasmid containing ASM cDNA, using the forward (F) primer EcoRI-ASM and reverse (R) primer ASM-XbaI. The resulting fragments can be cloned into pMT/BiP/V5-His (B) plasmid to obtain an ICAM-1-targeted ASM plasmid termed (B) (FIG. 7). (B) can be used for amplification in *E. coli* and expression in S2 cells, using single-site restriction enzyme digestion with XmaI, SpeI, EcoRI, and XbaI, respectively, and subsequent ligation. Oligonucleotides:

```
XmaI-ATG-γ3-SpeI-F
                                          (SEQ ID NO: 4)
5'-CCGGGATGAATAATCAAAAGATTGTTAACCTGAAAGAGAAGGTAGC

CCAGCTTGAAGCAA-3'

XmaI-ATG-γ3-SpeI-R
                                          (SEQ ID NO: 5)
5'-CTAGTTGCTTCAAGCTGGGCTACCTTCTCTTTCAGGTTAACAATCT

TTTGATTATTCATC-3'

XmaI-ATG-2γ3-SpeI-F
                                          (SEQ ID NO: 6)
5'-CCGGGATGAATAATCAAAAGATTGTTAACATCAAAGAGAAGGTAGC

CCAGATCGAAGCAA-3'

XmaI-ATG-2γ3-SpeI-R
                                          (SEQ ID NO: 7)
5'-CTAGTTTGCTTCGATCTGGGCTACCTTCTCTTTGATGTTAACAATC

TTTTGATTATTCATC-3'

XmaI-ATG-3γ3-SpeI-F
                                          (SEQ ID NO: 8)
5'-CCGGGATGAATAATCAAAAGCTTGTTAACATCAAAGAGAAGGTAGC

CCAGATCGAAGCAA-3'

XmaI-ATG-3γ3-SpeI-R
                                          (SEQ ID NO: 9)
5'-CTAGTTGCTTCGATCTGGGCTACCTTCTCTTTGATGTTAACAAGCT

TTTGATTATTCATC-3'

XmaI-ATG-A1-SpeI-F
                                          (SEQ ID NO: 20)
5'-CCGGGATGTACCCCGCCAGCTACCAGCGGA-3'

XmaI-ATG-A1-SpeI-R
                                          (SEQ ID NO: 21)
5'-CTAGTCCGCTGGTAGCTGGCGGGGTACATCC-3'

XmaI-ATG-D6-SpeI-F
                                          (SEQ ID NO: 22)
5'-CCGGGATGGGCTGCAAGCTGTGCGCCCAGA-3'

XmaI-ATG-D6-SpeI-R
                                          (SEQ ID NO: 23)
5'-CTAGTCTGGGCGCACAGCTTGCAGCCCATC-3'

XmaI-ATG-B7-SpeI-F
                                          (SEQ ID NO: 24)
5'-CCGGGATGTACCAGGCCACCCCCCTGCCCA-3'

XmaI-ATG-B7-SpeI-R
                                          (SEQ ID NO: 25)
5'-CTAGTGGGCAGGGGGGTGGCCTGGTACATCC-3'

XmaI-ATG-B8-SpeI-F
                                          (SEQ ID NO: 26)
5'-CCGGGATGGGCAGCCTGCTGAGCGCCGCCA-3'

XmaI-ATG-B8-SpeI-R
                                          (SEQ ID NO: 27)
5'-CTAGTGGCGGCGCTCAGCAGGCTGCCCATC-3'

XmaI-ATG-B9-SpeI-F
                                          (SEQ ID NO: 28)
5'-CCGGGATGTTCAGCCCCCACAGCCGGACCA-3'

XmaI-ATG-B9-SpeI-R
                                          (SEQ ID NO: 29)
5'-CTAGTGGTCCGGCTGTGGGGGCTGAACATC-3'

XmaI-ATG-B10-SpeI-F
                                          (SEQ ID NO: 30)
5'-CCGGGATGTACCCCTTCCTGCCCACCGCCA-3'

XmaI-ATG-B10-SpeI-R
                                          (SEQ ID NO: 31)
5'-CTAGTGGCGGTGGGCAGGAAGGGGTACATC-3'

SpeI-(Ser4Gly)2-EcoRI-F
                                          (SEQ ID NO: 10)
5'-ACTAGTTCTTCTTCTTCTGGCTCTTCTTCTTCTGGCGAATTC-3'

SpeI-(Ser4Gly)2-EcoRI-R
                                          (SEQ ID NO: 11)
5'-GAATTCGCCAGAAGAAGAAGAGCCAGAAGAAGAAGAACTAGT-3'

EcoRI-ASM-F
                                          (SEQ ID NO: 12)
5'-AATTCCCCCGCTACGGAGCGTCAC-3'

ASM-XbaI-R
                                          (SEQ ID NO: 13)
5'-CTAGACTAGCAAAACAGTGGCCTTG-3'
```

EXAMPLE 9

In Vivo Brain Transport of Therapeutic Carriers Targeted to ICAM-1 Via the Affinity Peptide 2γ3

Biocompatible PLGA carriers (100 nm diameter) were coated by surface absorption with the ICAM-1-targeting peptide 2γ3 and the recombinant enzyme acid sphingomyelinase (ASM), taken as an example for a therapeutic cargo. The resulting 2γ3/ASM PLGA carriers were injected intravenously in anesthetized C57Bl/6 mice. Three hours after injection, animals were euthanized under anesthesia, perfused and fixed though the left ventricle of the heart under ventilation, and the brain was isolated and processed for transmission electron microscopy.

Figure 2:
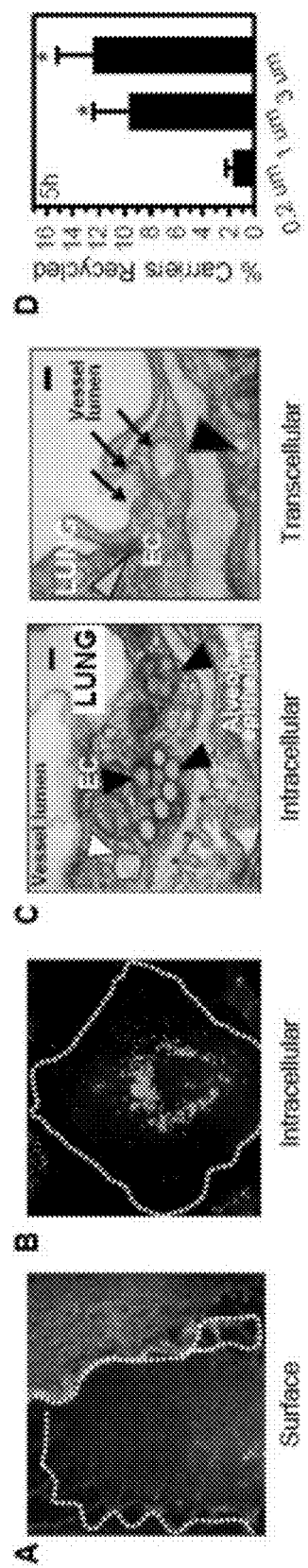
FIG. 2 illustrates the results of Example 2, where FIG. 2A-2C provide fluorescence and electron microscopy images of ICAM targeting by ICAM-1 specific targeting moieties
Figure 8A:
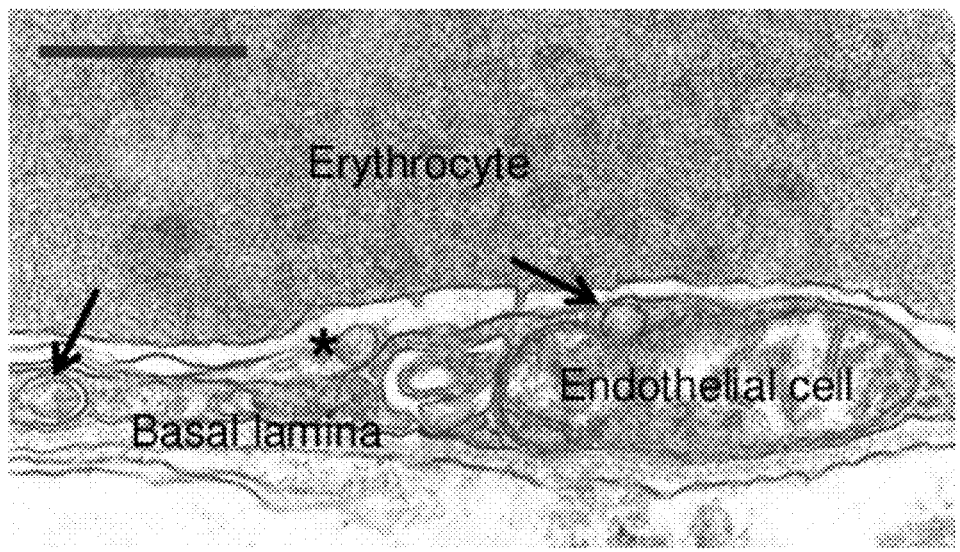
Figure 8B:
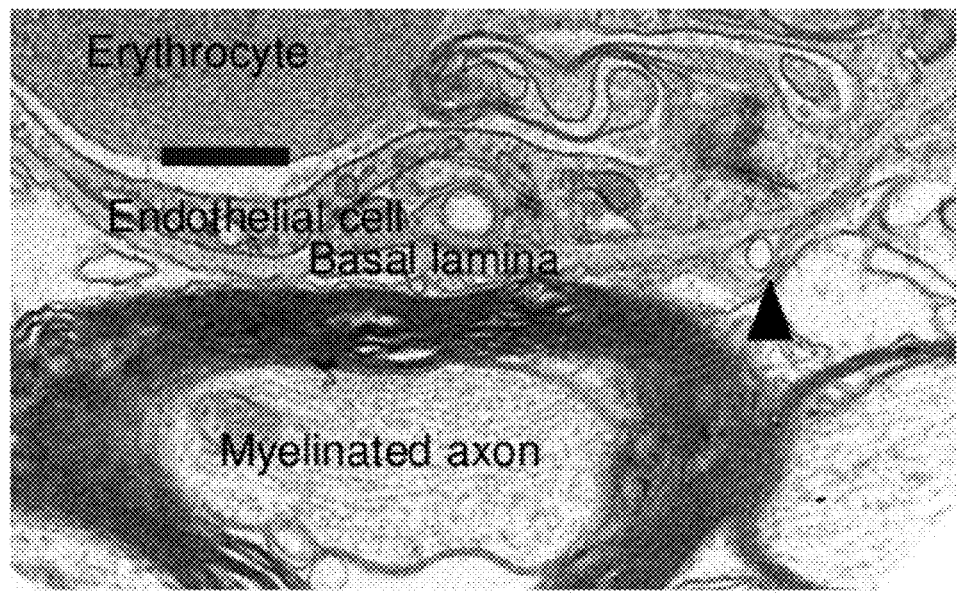

FIG. 8 provides transmission electron microscopy pictures showing biocompatible 2γ3/ASM PLGA carriers in brain of C57Bl/6 mice (3 h post-injection). Scale bar=500 nm. FIG. 8(A) 2γ3/ASM PLGA carriers bound to the surface of (asterisk) or endocytosed within (arrows) vascular endothelial cells in the blood-brain barrier FIG. 8(B) 2γ3/ASM PLGA carriers that have migrated across the blood-brain barrier into a region of the brain close to the myelinated axon of a neuron.

EXAMPLE 10

Inhibition of Inflammatory Leukocyte Transmigration Across Endothelial Cells by ICAM-1 Targeting Peptides Human endothelial cells (human umbilical vein endothelial cells (HUVECs)) were grown until formation of a continuous confluent monolayer in a transwell filter located between upper and lower chambers. The cells were then treated with tumor necrosis factor alpha to mimic inflammatory activation of endothelial cells and SDF1a was added to the lower chamber to generate a gradient to attract white blood cells, as during inflammation. Lymphocytes isolated from human peripheral blood were activated with interleukin 2 and added to the upper chamber above endothelial cells in the absence (control) or presence of ICAM-1-targeting peptides A1, B7, B8, B9, B10, or D6. Albumin or a peptide of scrambled sequence were used as negative controls which should not block inflammatory transmigration of leukocytes across endothelial cells. The anti-ICAM antibody LB2, which is known to block leukocyte adhesion to ICAM-1, was used as a positive control which should block such transmigration.

Leukocytes which transmigrated to the lower chamber below endothelial cells were counted to assess their transmigration. FIG. 9 provides a graph of the resulting leukocyte transmigration as a percentage of the control. The peptides annotated with an asterisk in FIG. 9 indicate that the peptide was effective in statistically significant blockage of leukocyte transmigration across endothelial cells. All ICAM-1-targeting peptides tested were shown to inhibit transmigration of leukocytes in a specific and effective manner.

EXAMPLE 11

In Vivo Inhibition of Lodging of Fibrin Microemboli in the Vasculature by ICAM-1 Targeting Peptides C57Bl/6 mice were first injected intravenously with γ3 to block ICAM-1 in the vascular endothelium in organs. Alternatively, injections of saline or anti-ICAM were used as controls. Fifteen minutes later the mice were injected with fibrin clots (microemboli around 3-5 micrometer) generated in the lab by established procedures.

Figure 10A:
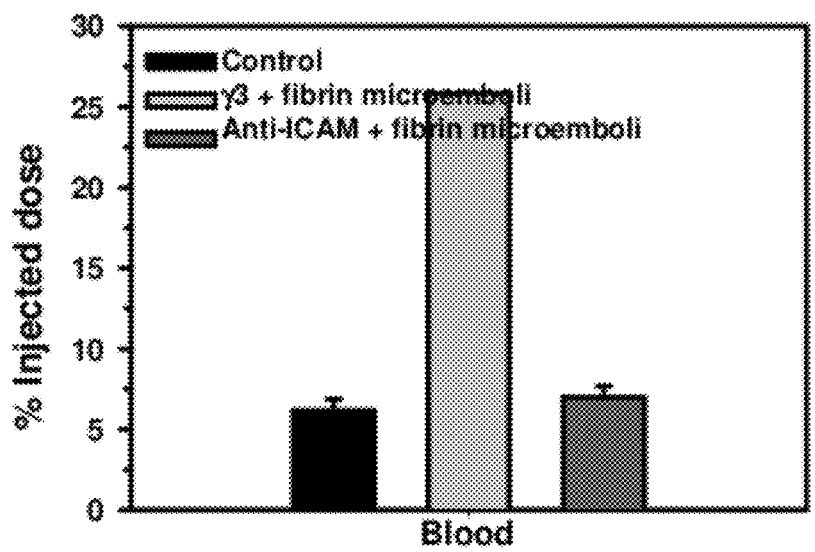
Figure 10B:
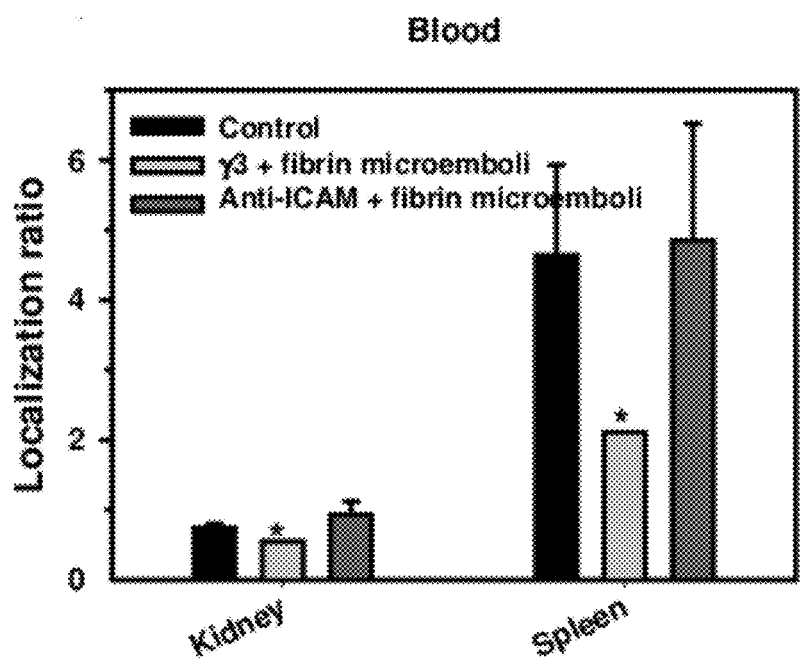

Following microemboli administration, the microemboli amounts were measured in a gamma counter and calculated as percent of injected dose in circulation or localization ratio (the percent injected dose/gram in an organ divided by percent injected dose/gram in blood). FIG. 10(A) is a graphical illustration of the amount of microemboli in circulation in blood, as evaluated at 1 min after injection and FIG. 10(B) is a graphical illustration of the amount of microemboli lodging in the vasculature of the kidneys and spleen at 15 min after injection.

In contrast to anti-ICAM, blocking of ICAM-1 with γ3 peptide caused fibrin microemboli to remain in circulation, attenuating microemboli lodging in organs.

EXAMPLE 12

ICAM-1 Expression in GI Epithelial Cells

Figure 11:
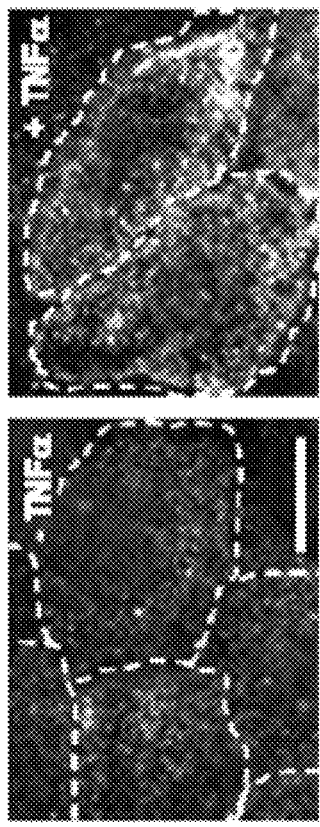

Prior to examining specific binding of anti-ICAM carriers (model 100 nm diameter fluorescent polystyrene-latex beads coated by surface absorption with anti-ICAM) to GI epithelial cells, ICAM-1 expression was verified. Human epithelial colorectal adenocarcinoma Caco-2 cell model was used. Both control cells as well as TNF-α-activated cells were used to mimic normal versus pathologically altered conditions. ICAM-1 was immunolabeled with anti-ICAM followed by FITC goat anti-mouse IgG in control versus TNF-α-activated Caco-2 cells (fixed) and imaged by fluorescence microscopy. Immunofluorescence and microscopy imaging revealed that Caco-2 cells expressed ICAM-1 under both conditions (FIG. 11; magnification bar=10 μm.).

EXAMPLE 13

Marked and Specific Binding of ICAM-1-Targeted Carriers in GI Epithelial Cells

Figure 12:
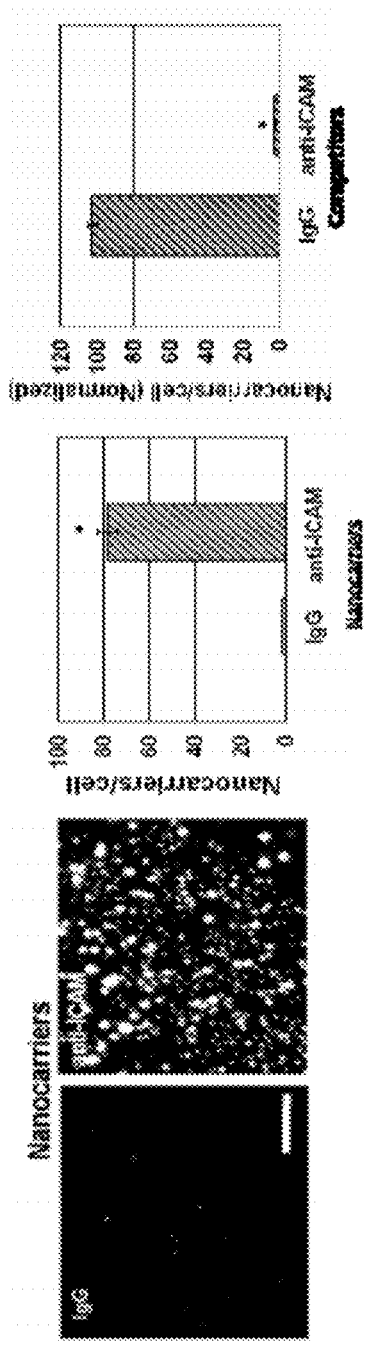

Specific binding of anti-ICAM carriers to Caco-2 cells was tested and results are provided in FIG. 12 (Magnification bar=10 μm. Data are means±S.E.M. (n≥20); *, p<0.001 by Student's t test). Binding of FITC carriers (control IgG or anti-ICAM carriers) to fixed TNF-α-activated Caco-2 cells was assessed by fluorescence microscopy. Anti-ICAM carriers, not IgG carriers, were found to bind to TNF-α-activated Caco-2 cells (FIG. 12A). The number of carriers bound per cell was automatically quantified by fluorescence microscopy and image analysis (FIG. 12B) revealed that binding of anti-ICAM carriers markedly exceeded that of non-specific IgG carriers by ~62 fold (78±4 versus 1.3±0.1 carriers/cell). These results verified the specificity of binding.

In addition, the Caco-2 cells were incubated with FITC anti-ICAM carriers in the presence of non-specific IgG or anti-ICAM. It was seen that presence of anti-ICAM antibodies free in solution greatly reduced binding of anti-ICAM carriers to 2.4±0.3% of the control value with no competitor, whereas the presence of IgG did not affect binding (102±2.6% of the control value) (FIG. 12C). Effective competition by anti-ICAM further confirmed the specificity of binding of anti-ICAM carriers to Caco-2 cells.

EXAMPLE 14

Kinetics of Binding and Endocytosis of ICAM-1-Targeted Carriers in GI Epithelial Cells The efficiency of targeting of anti-ICAM carriers in Caco-2 cells was determined. The amount of carriers bound per cell was quantified from fluorescence images of fixed TNF-α-activated Caco-2 cells incubated with FITC-labeled anti-ICAM carriers. Fluorescence analysis (FIG. 13A) revealed that significant binding of anti-ICAM carriers to activated Caco-2 cells occurred as early as 5 min (40.5±2.7 carriers bound per cell). This amount nearly doubled by 30 min, which indicated a fast binding rate and extent of carrier binding. Binding saturation occurred at 157 carriers bound per cell, demonstrating the high degree of targeting and potential of this strategy.

Figure 13:
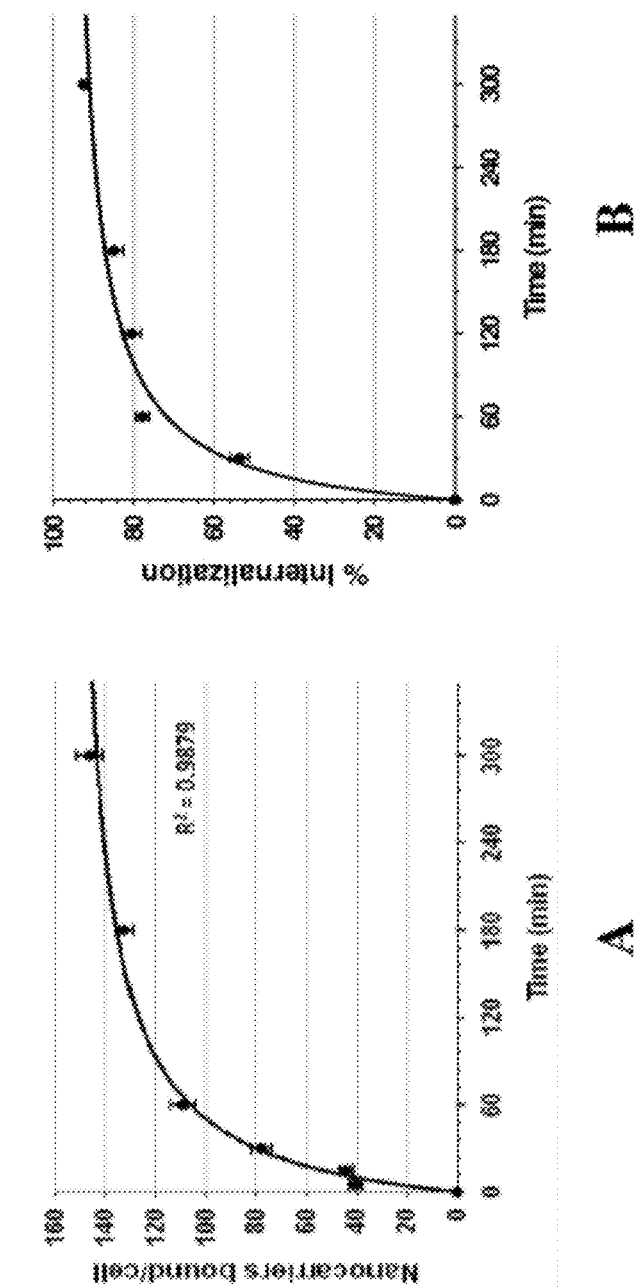

Furthermore the ability of anti-ICAM carriers to be endocytosed by Caco-2 cells was examined. FITC-labeled anti-ICAM carriers were first incubated with cells for 30 min to allow binding, then non-bound carriers were washed and cells were incubated for varying times to allow carrier uptake. After cell fixation, surface-bound carriers were stained with Texas Red secondary antibody. Fluorescence quantification expressed as % internalization revealed fast kinetics for carrier uptake ($t_{1/2}$=22 min and saturation at ~1 h). Data are shown as means±S.E.M. (n≥20). Such analysis of uptake kinetics showed that FITC-labeled anti-ICAM carriers were internalized very rapidly by GI epithelial cells (50% internalization after 22 min) (FIG. 13B). Internalization was highly efficient: approximately 90% of the carriers bound to cells were internalized, which represents ~60 carriers per cell.

EXAMPLE 15

Figure 14:
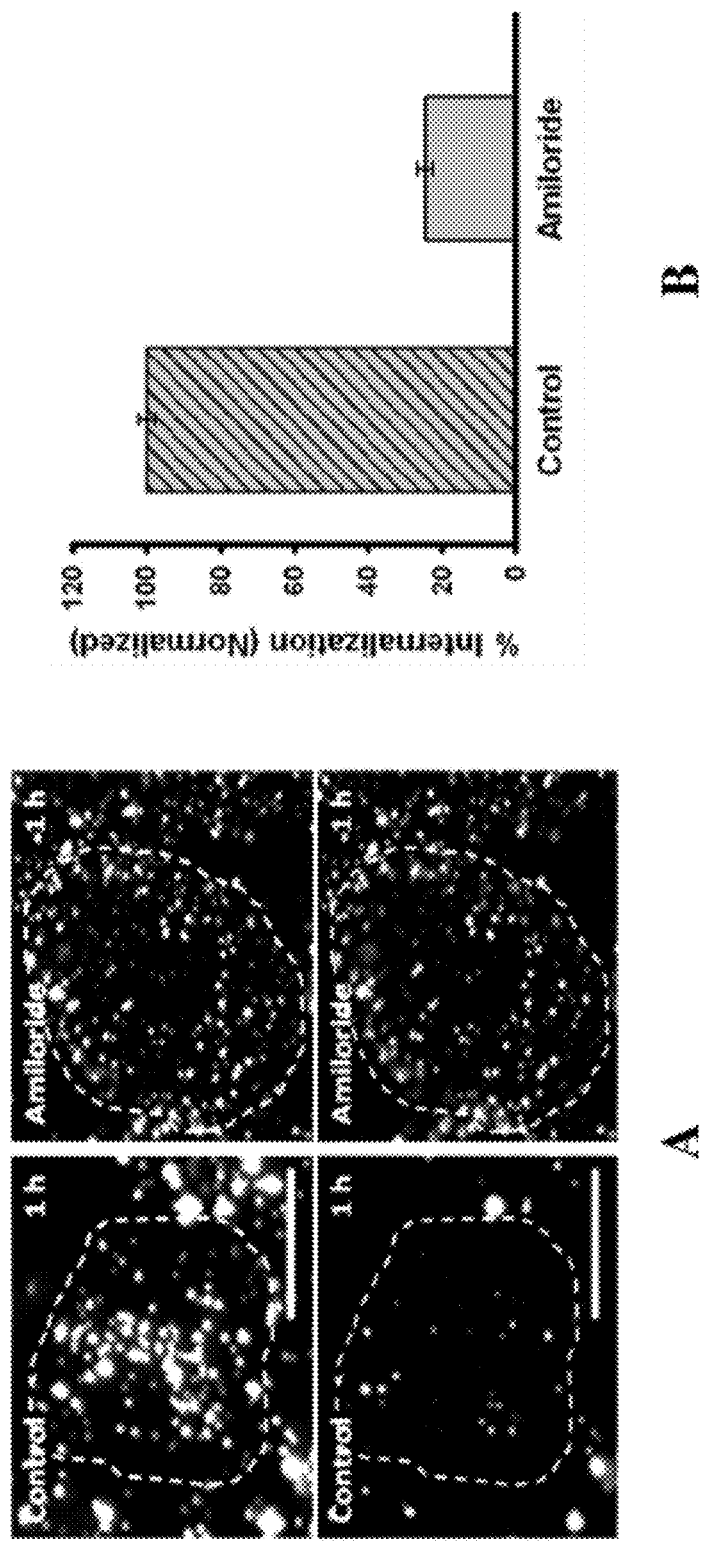

ICAM-1-Targeted Carriers are Internalized by CAM-Mediated Endocytosis in GI Epithelial Cells The mechanism of uptake for Caco-2 cells treated with amiloride, a known inhibitor of CAM-mediated endocytosis (Muro et al., 2003), was examined. TNF-α-treated Caco-2 cells were incubated with FITC-labeled anti-ICAM carriers in the presence or absence of amiloride (1 h, 37° C.), and surface-bound carriers were stained with TxR goat anti-mouse. Fluorescence microscopy revealed that amiloride reduced carrier uptake to 20% of the control value (FIG. 14). Upper panels of FIG. 14A show total carriers associated to cells, whereas lower panels show the fraction of surface-bound, non-internalized carriers. (Magnification bar=10 μm.) The fluorescence microscopy images were analyzed for the ratio of internalized carriers to surface-bound carriers, expressed as % internalization and normalized to the control. (FIG. 14B; Data are shown as means±S.E.M. (n≥20). *, p<0.001 by Student's t test.)

The total amount of cell-associated carriers per cell was similar for both amiloride-treated and control cells, which suggests that the effects of this inhibitor in internalization are not due to effects on binding. Therefore, CAM-mediated endocytosis is responsible for the uptake of anti-ICAM carriers in GI epithelial cells.

EXAMPLE 16

Permeability Barrier in a Transwell GI Epithelial Model

In vitro permeability models designed to mimic physiological transport of materials from the apical (i.e. intestinal lumen) to the basolateral (i.e. systemic circulation) surface of cells were then used. Caco-2 cells grown on porous permeable inserts are known to exhibit the phenotype of mature enterocytes, which include the presence of brush border microvilli and tight junctions, dome formation, and production of brush border enzymes (Hidalgo, I. J., et al., Gastroenterology 96 (1989) 736-749; Hidalgo, I. J. & Borchardt, R. T., *Biochim. Biophys. Acta* 1028 (1990): 25-30.). Also, Caco-2 cells cultured on permeable membranes have been established in previous works as a model of the human intestine to study transepithelial drug transport (Hidalgo, I. J. & Borchardt, R. T., *Biochim. Biophys. Acta* 1028 (1990): 25-30; Artusson, P., *J. Pharma. Sci.* 79 (1990): 476-482.).

The Caco-2 model was confirmed as representative of the GI epithelium in terms of the mentioned features. It was evaluated whether Caco-2 cells could form a permeability barrier (indicative of the GI epithelial barrier) under the particular growth conditions. In addition, the presence of ICAM-1 was assessed to ensure nanocarrier targeting would occur in this more physiologically relevant transport model.

In order to evaluate the proper growth conditions for a Caco-2 transport model, Caco-2 cells were cultured on permeable membrane inserts (0.4 μm pore) and the integrity of the permeability barrier was assessed using transepithelial electrical resistance (TEER) measured over time, whereby increased resistance to the flow of electrical current typically signifies closing of the epithelial junctions, a feature of healthy GI epithelium. It was verified whether TEER values indicative of a permeability barrier correlated with the formation of tight junctions between Caco-2 cells. TEER values around or above 300 Ω×cm² indicate closing of intercellular junctions and formation of the permeability barrier.

Figure 15:
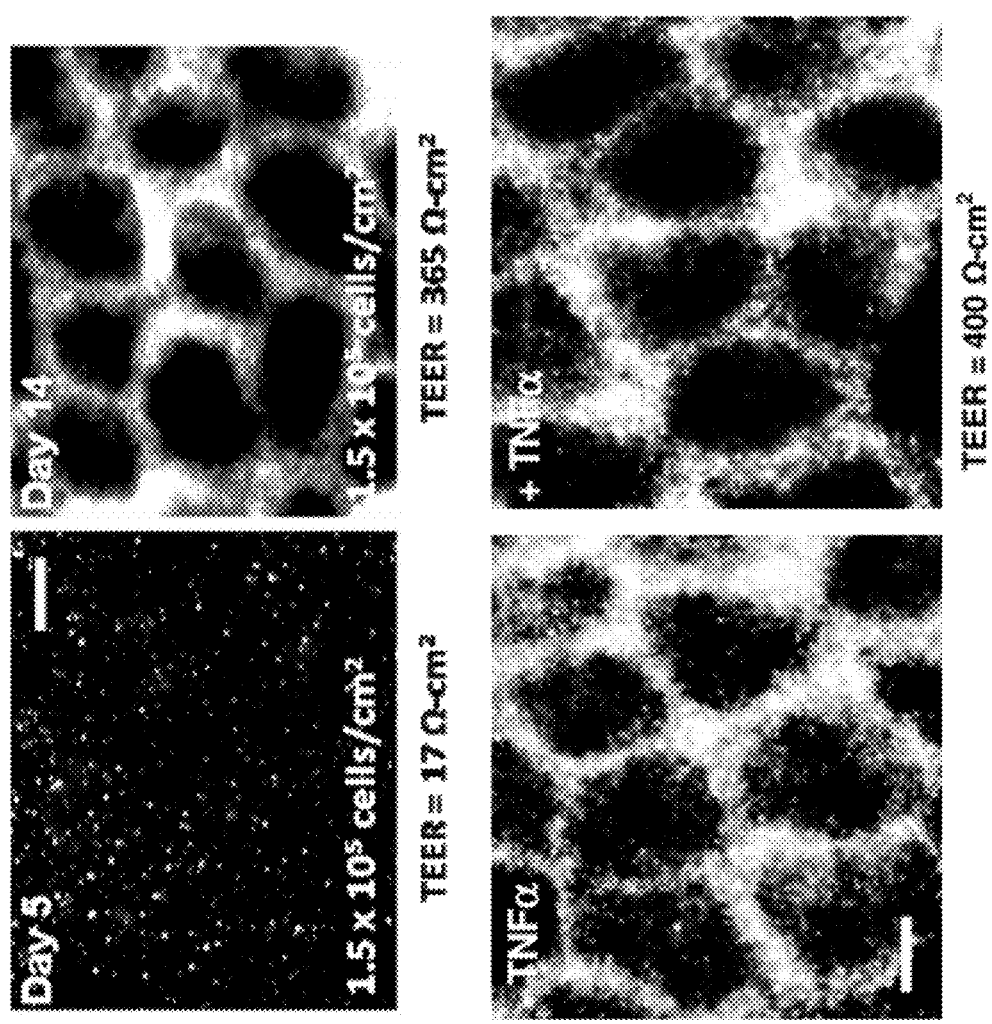

As shown in FIG. 15, cells presented low TEER values and did not form tight junctions within the first 5 days, but they showed a marked TEER increase indicative of a permeability barrier (≥300 Ω×cm²) by day 14. Tight junctions formation was further confirmed by immunolabeling tight junctions with anti-occludin followed by TxR donkey anti-goat IgG. Images were obtained using fluorescence microscopy. (Magnification bar=10 μm.) In addition, treatment of cells with TNFα to mimic pathological activation of GI epithelial cells did not disrupt this permeability barrier. Therefore, this represents a good model to test transepithelial transport of ICAM-1-targeted carriers across the GI.

EXAMPLE 17

ICAM-1 Expression in Differentiated GI Epithelial Cells

Figure 16:
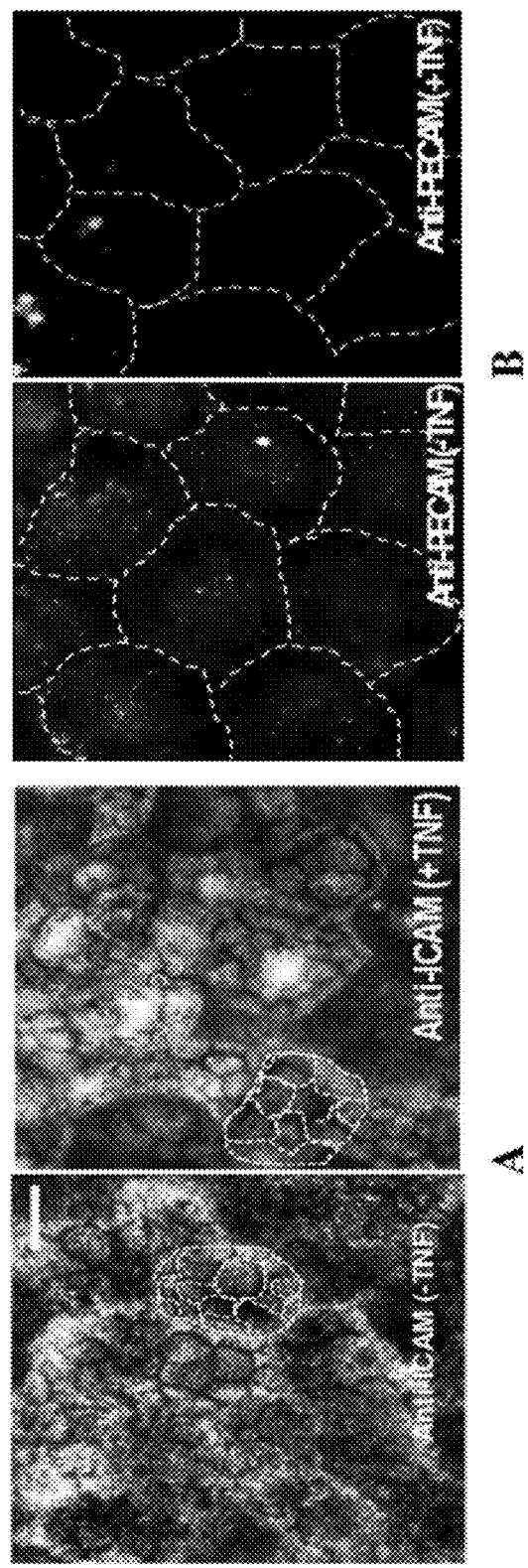

In order to ensure that targeting of anti-ICAM carriers will also occur in such polarized Caco-2 cells, expression of ICAM-1 was examined. Resting and TNF-α-activated Caco-2 cells were grown on permeable membrane inserts. Once confluence was confirmed by TEER, the cells were immunolabeled with either anti-ICAM or control anti-PECAM, followed by FITC-labeled goat anti-mouse IgG. As expected, immunofluorescence with anti-ICAM FIG. 16A) confirmed the expression of ICAM-1 in Caco-2 cells grown to confluence and forming a permeability barrier on transwell filters. A single cell and its microvilli are marked in FIG. 16 (Magnification bar=10 μm), representative of differentiated Caco-2 cells. As a control, the absence of platelet endothelial cell adhesion molecule-1 (PECAM-1), a related cell adhesion molecule which is only expressed by endothelial cells, confirmed the specificity of ICAM-1 expression (FIG. 16B). These experiments further revealed expression of ICAM-1 in microvilli surfaces on Caco-2 cells. Surprisingly, in this more physiological model of GI epithelial cells, ICAM-1 expression was very high in control cells (comparable to pathologically activated cells), supporting the potential of this strategy for drug delivery in both settings.

EXAMPLE 18

Transport of ICAM-1-Targeting Carriers Across GI Epithelial Monolayers

Transport of anti-ICAM carriers across Caco-2 cell layers was examined in cells growing on transwell filters by addition of carriers to the apical/top chamber and collection of transported carriers from the basolateral/bottom chamber. Caco-2 monolayers grown on permeable membrane inserts were incubated with $^{125}$I-anti-ICAM or control $^{125}$I-IgG carriers added to the apical chamber.

Figure 17:
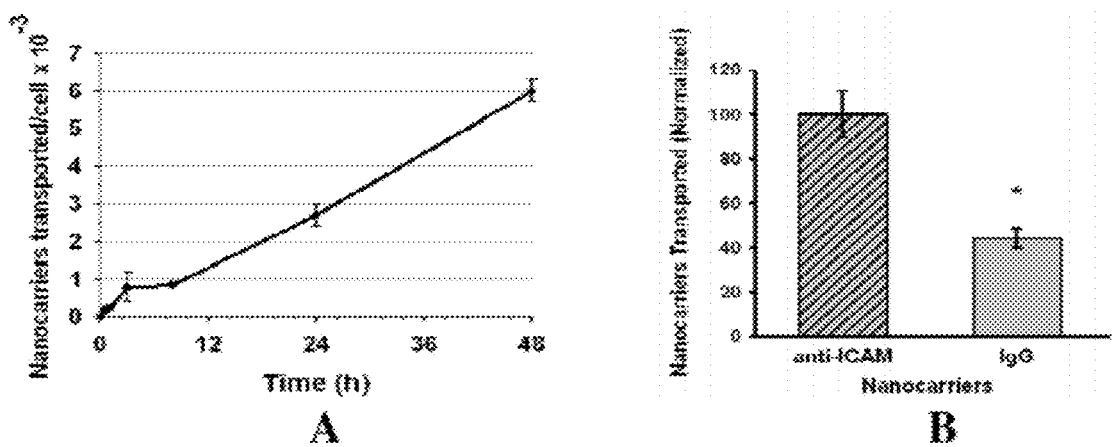

Radioactivity in the basolateral fraction was measured at each time point and converted to the amount of anti-ICAM carriers transported per cell. As shown in FIG. 17A, transport of anti-ICAM carriers from the apical to the basolateral side of Caco-2 cells was highly relevant in absolute values, which markedly increased from ~170 anti-ICAM carriers being transported per cell at 30 min up to ~6,000 carriers per cell at 48 h. This level of transport is equivalent to transport of as much as $3\times10^7$ carriers per mm² epithelial tissue. These results demonstrate the surprising and unexpected high extent to which anti-ICAM carriers are transported across Caco-2 cells.

In addition, transport was specific as shown by the fact that only a fraction of control IgG carriers were transported across the Caco-2 monolayer even after very long incubation times FIG. 17B shows transport of IgG carriers normalized to the transport of anti-ICAM carriers at 24 h. (Data are shown as means±S.E.M. (n=4 wells). *, p<0.001 by Student's t test.)

EXAMPLE 19

Rate of Carrier Transport Across GI Epithelial Cells

Figure 18:
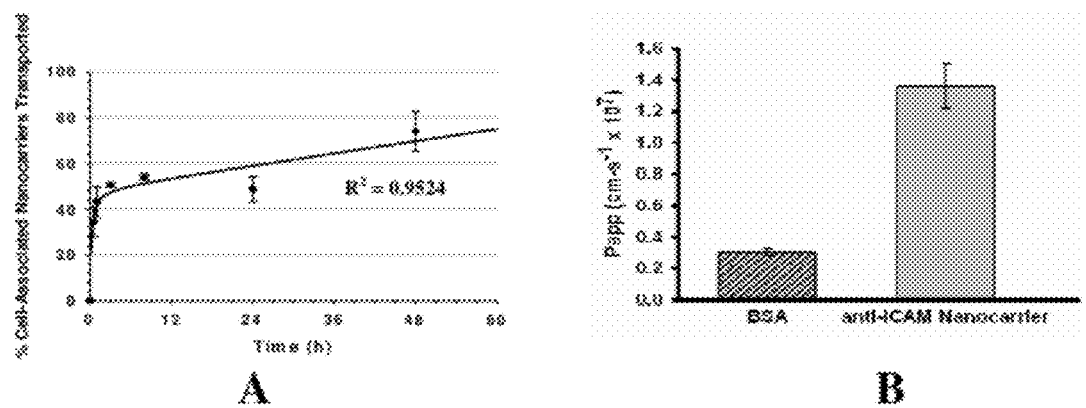

Caco-2 cells grown on permeable membrane inserts were incubated with $^{125}$I-anti-ICAM carriers over time. Percent of transported carriers was calculated as the ratio of carriers in the basolateral fraction to that in the combined basolateral and cell fractions. FIG. 18A shows the percent of transported carriers with respect to the total amount of carriers associated to the cells. This parameter demonstrates a very rapid rate of transport, e.g., 34% after only 30 min, 43% after 1 h, and a maximum value of 75% of carrier transport at 48 h, indicating that the majority of anti-ICAM carriers that bind to cells at the apical side are transported across the cell body and secreted at the abluminal side.

The apparent permeability coefficient ($P_{app}$) is another parameter that indicates rate of transport and allows comparison of permeability between different solutes. Apparent permeability coefficients were derived from rates of transport of $^{125}$I-bovine serum albumin (BSA) versus $^{125}$I-anti-ICAM carriers (24 h). The permeability coefficient of anti-CAM carriers was compared to that of albumin, a serum protein known to maintain the oncotic pressure by being capable of transport across cellular layers into the parenchyma of tissues (Rezai, K. A., et al., *Graefes. Arch. Clin. Exp. Opthalmol.* 235 (1997): 48-55; Savin, V. J. et al., *J Am Soc Nephrol* 3 (1992): 1260-1269.). As shown in FIG. 18B, the relative permeability of $^{125}$I-anti-ICAM carriers was 4.6 fold greater than that of $^{125}$I-albumin (1.4±0.1×10$^7$ cm-s$^{-1}$ versus 0.3±0.02×10$^7$ cm-s$^{-1}$), suggesting that anti-ICAM carriers are involved in fast transport with respect to a standard known for passive transport. (Data are shown as means±S.E.M. (n=4 wells). *, p<0.001 by Student's t test.)

EXAMPLE 20

Transport of ICAM-1-Targeting Carriers Across GI Epithelial Cells by CAM-Mediated Transcytosis The mechanism of transport of anti-ICAM carriers across Caco-2 cells was examined. Paracellular transport operates via the opening of cell junctions, which can be indicated by a drop in transepithelial electrical resistance. TEER was measured during transport of $^{125}$I-anti-ICAM carriers to assess paracellular transport, indicated by decreased TEER. Control TEER measured prior to transport is marked as the interval of S.E.M (two lines). Results are provided in FIG. 19A, where it can be seen that the transport of anti-ICAM carriers across Caco-2 cells over time did not significantly lowered TEER with respect to pre-transport measurements (273±33 vs 290±24 Ω-cm$^2$, respectively). Maintenance of high epithelial resistance suggested that anti-ICAM carriers do not influence opening of intercellular junctions over the course of transport and, hence, it is likely that they do not compromise the integrity of Caco-2 cell monolayers.

In addition, because albumin utilizes paracellular as well as caveolin-mediated transcellular transport, it was used as a marker to indicate whether anti-ICAM carriers are transported via either of these mechanisms. The amount of transported $^{125}$I-albumin (bovine serum albumin or BSA) during simultaneous transport of anti-ICAM carriers (3 h) was normalized to the control (absence of anti-ICAM carriers). Radioisotope tracing confirmed that the transport of anti-ICAM carriers did not increase the quantity of $^{125}$I-albumin transported (FIG. 19B), implying the carriers do not open tight junctions to allow greater permeability of albumin or are transported via caveolin-mediated pathway.

Figure 19:
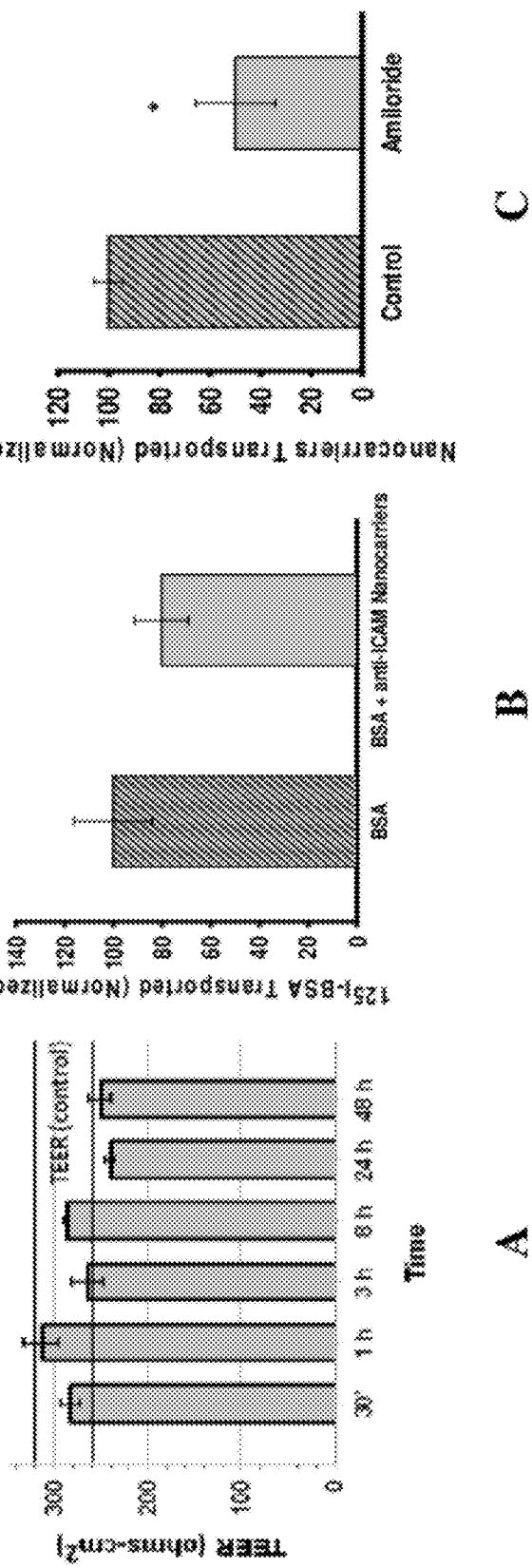

Amiloride-treated versus control Caco-2 cells were incubated with $^{125}$I-anti-ICAM carriers for 3 h. Radioisotope analysis was conducted to determine the amount of transported carriers. The results further demonstrated that amiloride, a drug that inhibits CAM-mediated endocytosis, reduced the transport of $^{125}$I-anti-ICAM carriers by about 50% (FIG. 19B). Therefore, these results support a role for CAM-mediated endocytosis in the transcytosis of anti-ICAM carriers by Caco-2 cells. (Data are shown as means±S.E.M. (n=4 wells). *, p<0.01 by Student's t test.)

Transepithelial transport involving CAM endocytosis has not yet been identified or characterized. Although opening of tight junctions may lead to faster transport, at the same time paracellular pathways poses a threat to epithelial monolayer integrity and its permeability barrier. Hence, these results seem to indicate the potential safety of transport of anti-ICAM carriers in the gastrointestinal epithelium.

EXAMPLE 21

CAM-Mediated Transport of ICAM-1-Targeting Moieties in GI Epithelial Cells

Antibodies to ICAM-1 have been shown to induce therapeutic benefits upon binding to their target (Takei, Y. et al., *Transplant Proc* 28 (1996): 1103-1105; Kavanaugh, A. F., et al., *Arthritis Rheum* 40 (1997): 849-853; Hallahan, D. E. & Virudachalam, S. *PNAS.* 94 (1997): 6432-6437). In addition, targeting moieties alone, including anti-ICAM, can serve as affinity carriers for drugs.

Figure 20:
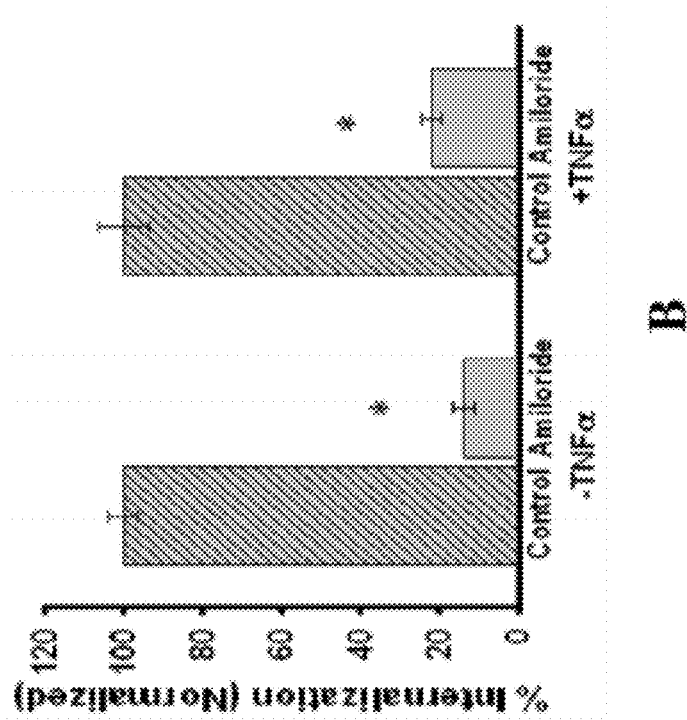
Figure 20:
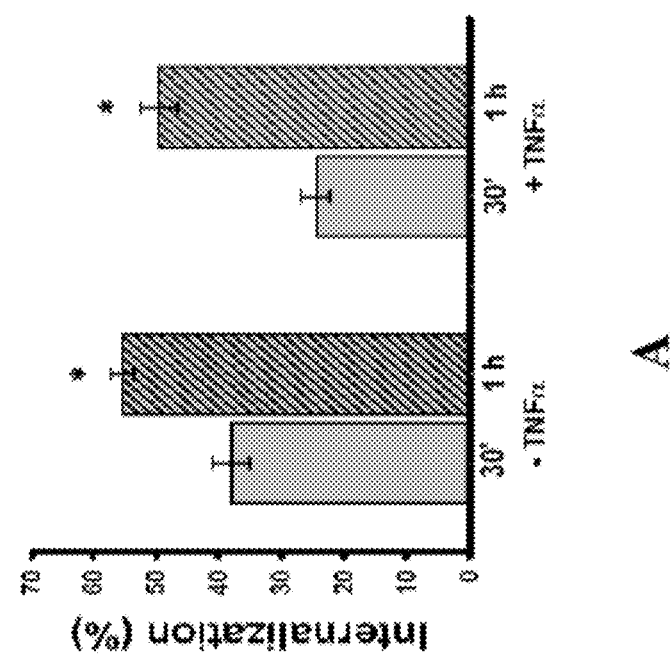

In order to assess the capability of anti-ICAM as therapeutics or affinity carriers, the binding and potential endocytic uptake of anti-ICAM in Caco-2 cells was tested. Upon 30 min and 1 h incubation (37° C.) in TNF-α-stimulated and control Caco-2 cells, surface-bound anti-ICAM was immunolabeled with TxR goat anti-mouse IgG, following cell permeabilization and immunolabeling of both bound and internalized anti-ICAM fractions with FITC goat anti-mouse IgG. Percent internalization was automatically quantified from the images using fluorescence microscopy (FIG. 20A). Similar experiments were conducted in the absence (control) or presence of amiloride, a drug that inhibits CAM-mediated endocytosis. Percent internalized anti-ICAM was automatically analyzed by fluorescence microscopy (FIG. 20B).

In previous studies describing CAM-mediated endocytosis, monomeric (a single copy of) anti-ICAM allowed binding but not internalization in the case of endothelial cells. Surprisingly, fluorescence microscopy of surface versus internalized fractions showed that anti-ICAM (non-coupled to carriers) induced endocytosis in both control and pathological models of Caco-2 cells. Moreover, the levels of endocytosed anti-ICAM at were comparable in control and TNF-α-activated Caco-2 cells, indicating similar uptake kinetics between the two conditions. The mechanism of anti-ICAM uptake was inferred by treatment with amiloride, which indicated that uptake of anti-ICAM by Caco-2 cells also operates via CAM-mediated endocytosis even in the case of non-multivalent binding to ICAM-1. (FIG. 20; Data are shown as means±S.E.M. (n≥50). *, p<0.001 by Student's t test.)

EXAMPLE 22

Peptides as Targeting Moieties for GI Delivery

Similar experiments using short peptides derived from fibrin and/or peptides identified by phage display as targeting moieties for specific targeting of ICAM-1 on GI epithelial cells are expected to demonstrate that compounds containing such peptides as targeting moieties will be similarly transported across the GI epithelial layer.

Such anticipated results are based upon the prior examples demonstrating uptake of the peptide-containing compounds by vascular endothelial cells and transport across the blood-brain barrier (Example 9; FIG. 8).

Similar uptake by GI epithelial cells and observation of transport across the GI epithelial layer are expected.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method for delivery of an agent to the surface of the gastrointestinal epithelium, comprising orally administering a composition comprising:
   a) a targeting moiety selected from SEQ ID NO: 2, SEQ ID NO:3, SEQ ID NO:14, SEQ ID NO:15, SEQ ID NO:16, SEQ ID NO:17, SEQ ID NO:18, and SEQ ID NO:19; and
   b) an agent, wherein the targeting moiety recognizes and binds to a target on a gastrointestinal epithelial cell.

2. A method for delivery of an agent across the gastrointestinal epithelium, comprising orally administering a composition comprising:
   a) a targeting moiety selected from SEQ ID NO:2, SEQ ID NO:3, SEQ ID NO:14, SEQ ID NO:15, SEQ ID NO:16, SEQ ID NO:17, SEQ ID NO:18, and SEQ ID NO:19; and
   b) an agent, wherein the targeting moiety recognizes and binds to a target on a gastrointestinal epithelial cell and the composition is transported across the gastrointestinal epithelium.

3. The method of claim 2, wherein the agent comprises any of a research probe, an analytical probe, a reporter probe, a molecular probe, a diagnostic agent, a therapeutic agent, a biologically active agent, a research agent, an analytical agent, an imaging agent, a monitoring agent, an enzyme, a protein, a peptide, a nucleic acid, a lipid, a sugar, a hormone, a lipoprotein, a chemical, a virus, a bacterium, a cell, a biosensor, a marker, an antibody and a ligand.

4. The method of claim 3, wherein the agent comprises any of the enzymes involved in Pompe Disease, GM1 gangliosidosis, Tay-Sachs disease, GM2 gangliosidosis, Sandhoff disease, Fabry disease, Gaucher disease, metachromatic leukodystrophy, Krabbe disease, Niemann-Pick disease type A, Niemann-Pick disease type B, Niemann-Pick disease type C, Niemann-Pick disease type D, Farber disease, Wolman disease, Hurler Syndrome, Scheie Syndrome, Hurler-Scheie Syndrome, Hunter Syndrome, Sanfilippo A Syndrome, Sanfilippo B Syndrome, Sanfilippo C Syndrome, Sanfilippo D Syndrome, Morquio A disease, Morquio B disease, Maroteaux-Lamy disease, Sly Syndrome, α-mannosidosis, β-mannosidosis, fucosidosis, aspartylglucosaminuria, sialidosis, mucolipidosis II, mucolipidosis III, mucolipidosis IV, Goldberg Syndrome, Schindler disease, cystinosis, Salla disease, infantile sialic acid storage disease, Batten disease, infantile neuronal ceroid lipofuscinosis, and prosaposin.

5. The method of claim 2, wherein the target comprises a cell adhesion molecule (CAM) expressed on the surface of the gastrointestinal epithelial cell.

6. The method of claim 2, wherein the target comprises intercellular adhesion molecule-1 (ICAM-1).

7. The method of claim 2, wherein the transport comprises CAM-mediated endocytosis.

8. The method of claim 2, further comprising a delivery carrier for transport of the targeting moiety and agent to the gastrointestinal epithelial cell.

9. The method of claim 2, further comprising a protective agent effective to protect the targeting moiety and agent from degradation prior to arrival at the locus of the gastrointestinal epithelial cell.

10. The method of claim 9, wherein the protective agent comprises a polymer.

11. The method of claim 2, wherein the composition further comprises a second targeting moiety, effective to target a cell, tissue or organ after transport across the gastrointestinal epithelium, wherein the second targeting moiety recognizes and binds to a target on the cell, tissue or organ, and is effective to deliver the agent to the cell, tissue or organ.

12. The method of claim 9, wherein the wherein the second targeting moiety comprises a moiety selected from SEQ ID NO:1, SEQ ID NO:2, SEQ ID NO:3, SEQ ID NO:14, SEQ ID NO:15, SEQ ID NO:16, SEQ ID NO:17, SEQ ID NO:18, SEQ ID NO:19, antibody, an aptamer, a nucleic acid, a peptide, a carbohydrate, a lipid, a vitamin, a toxin, a component of a microorganism, a hormone, and a receptor ligand.

* * * * *

UNITED STATES PATENT AND TRADEMARK OFFICE
CERTIFICATE OF CORRECTION

PATENT NO. : 8,778,307 B2  Page 1 of 1
APPLICATION NO. : 13/463796
DATED : July 15, 2014
INVENTOR(S) : Silvia Muro Galindo It is certified that error appears in the above-identified patent and that said Letters Patent is hereby corrected as shown below:

In the Specification

Column 17, line 18: "(Ser-4-Gly)$_2$" should be -- (Ser4-Gly)2 --.

Column 17, line 27: "6H is" should be -- 6His --.

Column 26, lines 16 and 18: "273/$^{125}$I-ASM" should be -- 2γ3/$^{125}$I-ASM --.

Column 27, line 3: "SpeI-Ser4Gly)-2-EcoRI" should be -- SpeI-(Ser4Gly)2-EcoRI --.

Signed and Sealed this
Fourth Day of November, 2014

Michelle K. Lee
*Deputy Director of the United States Patent and Trademark Office*